(12) United States Patent
Seville

(10) Patent No.: US 6,914,250 B2
(45) Date of Patent: Jul. 5, 2005

(54) FLUOROMETRIC DETECTION USING VISIBLE LIGHT

(75) Inventor: Mark Seville, Mancos, CO (US)

(73) Assignee: Clare Chemical Research, Inc., Dolores, CO (US)

(*) Notice: Subject to any disclaimer, the term of this patent is extended or adjusted under 35 U.S.C. 154(b) by 223 days.

(21) Appl. No.: 10/313,892

(22) Filed: Dec. 6, 2002

(65) Prior Publication Data

US 2003/0173525 A1 Sep. 18, 2003

Related U.S. Application Data

(63) Continuation-in-part of application No. 09/753,783, filed on Jan. 2, 2001, now Pat. No. 6,512,236, which is a continuation of application No. 09/036,034, filed on Mar. 6, 1998, now Pat. No. 6,198,107.

(60) Provisional application No. 60/040,124, filed on Mar. 7, 1997.

(51) Int. Cl.[7] .............................................. G01N 21/64
(52) U.S. Cl. ................................................. 250/458.1
(58) Field of Search ........................... 250/458.1, 459.1

(56) References Cited

U.S. PATENT DOCUMENTS

| | | | | |
|---|---|---|---|---|
| 2,113,973 A | * | 4/1938 | Addink | 250/487.1 |
| 3,802,102 A | | 4/1974 | Licciardi | 40/132 R |
| 4,071,883 A | | 1/1978 | Dennis | 362/97 |
| 4,117,338 A | | 9/1978 | Adrion et al. | 250/461 R |
| 4,266,535 A | * | 5/1981 | Moret | 600/249 |
| 4,906,100 A | | 3/1990 | Rice et al. | 356/417 |
| 5,108,179 A | | 4/1992 | Myers | 356/344 |
| 5,274,240 A | | 12/1993 | Mathies et al. | 250/458.1 |
| 5,306,144 A | * | 4/1994 | Hibst et al. | 433/29 |
| 5,315,375 A | | 5/1994 | Allen | 356/417 |
| 5,324,940 A | * | 6/1994 | Ekstrom | 250/302 |
| 5,327,195 A | | 7/1994 | Ehr | 355/113 |
| 5,347,342 A | | 9/1994 | Ehr | 355/113 |
| 5,363,854 A | | 11/1994 | Martens et al. | 128/665 |
| 5,387,801 A | | 2/1995 | Gonzalez et al. | 250/504 R |
| 5,543,018 A | | 8/1996 | Stevens et al. | 204/461 |
| 5,736,744 A | | 4/1998 | Johannsen et al. | 250/505.1 |
| 5,742,066 A | * | 4/1998 | Cavestri | 250/504 R |
| 5,760,407 A | * | 6/1998 | Margosiak et al. | 250/461.2 |
| 5,856,866 A | | 1/1999 | Shimizu et al. | 356/73 |
| 6,161,323 A | | 12/2000 | Kageyama | 43/4.5 |
| 6,198,107 B1 | | 3/2001 | Seville | 250/458.1 |
| 6,512,236 B2 | | 1/2003 | Seville | 250/458.1 |

FOREIGN PATENT DOCUMENTS

| | | | | |
|---|---|---|---|---|
| CA | 2117345 | 7/1993 | .......... | G01N/21/64 |
| CA | 2136209 | 11/1993 | .......... | G01N/21/64 |
| CA | 2093532 | 10/1994 | .......... | G01N/21/64 |
| CA | 2197068 | 2/1996 | .......... | G01N/21/64 |
| CA | 2207488 | 6/1996 | .......... | G01N/21/64 |

(Continued)

OTHER PUBLICATIONS

Jenkins, F.A. and White, H.E., *Fundamentals of Optics* (4th ed.) McGraw–Hill, Toronto 1976, pp. 503–504.

(Continued)

*Primary Examiner*—Constantine Hannaher
(74) *Attorney, Agent, or Firm*—Greenlee, Winner and Sullivan, P.C.

(57) ABSTRACT

Systems, devices and methods of the present invention are for viewing a pattern of fluorophors capable of fluorescing when exposed to visible light, e.g., fluorescently stained DNA, protein or other biological material. The system includes a light source emitting light in the visible spectrum, such as a fluorescent lamp used in domestic lighting, a first optical filter capable of transmitting light from the source at wavelengths capable of exciting the fluorophors and of absorbing light of other wavelengths, and a second optical filter capable of blocking substantially all the light from the source not blocked by the first filter, so that the only light reaching the viewer is light produced by fluorescence of the fluorophors.

54 Claims, 30 Drawing Sheets

FOREIGN PATENT DOCUMENTS

| CA | 2171588 | 9/1996 | .......... G01N/21/64 |
| CA | 2234950 | 5/1997 | .......... G01N/21/64 |
| CA | 2251809 | 10/1997 | .......... G01N/21/64 |
| CA | 2253403 | 11/1997 | .......... G01N/21/64 |
| EP | 0 603 783 A1 | 6/1994 | .......... G01N/33/52 |
| JP | 10-132744 | 5/1998 | .......... G01N/21/64 |
| JP | 10-274637 | 10/1998 | .......... G01N/27/447 |

OTHER PUBLICATIONS

Herolab (Apr. 1995), "Gel–Dokumentation and Analyse," pp. 1–3.

UVP (Jun. 1991), "Product Catalog", pp. 1–7 and 9–12.

UVP International Ultra–Violet Products, (Feb. 1990), "New Products," UVP International Newsletter, 4 pp.

Herolab GMBH, (Aug. 1995), "Produktkatalog," *Herolab Highlights,* 1:1–7, XP002158317.

Brunk, C.F. and Simpson, L., (Oct. 1977), "Comparison of Various Ultraviolet Sources for Fluorescent Detection of Ethidium Bromide–DNA Complexes in Polyacrylamide Gels," *Analytical Biochemistry* 82:455–462.

Golden, Gregory S., (May 1994), Use of Alternative Light Source Illumination in Bite Mark Photography, *J. Forensic Sciences,* 39:815–823.

Gründemann, D. and Schömig, E., (Nov. 1996), "Protection of DNA During Preparative Agarose Gel Electrophoresis Against Damage Induced by Ultraviolet Light," *BioTechniques* 21:898–903.

Haughland, R.P., "Hand Book of Fluorescent Probes and Research Chemicals," (1996) 6$^{th}$, Edition, Michelle T.Z. Spence, Ed., *Molecular Probes Inc., Eugene OR,* pp. 13–18, 25–28 and 29–35.

Menzel, E.R., (1991), "An Introduction to Lasers, Forensic Lights and Fluorescent Fingerprint Detection Techniques," *Lightning Powder Company, Inc., Salem OR.*

Neri et al., (Apr. 1996), "Multipurpose High Sensitivity Luminescence Analyzer (LUANA): Use in Gel Electrophoresis," *BioTechniques* 20(4):708–713.

Payton Scientific Inc. website—http://home.att.net/~payton-scientific/page6.html, pp. 1–2, date of publication unknown (downloaded Jul. 21, 1999).

Payton Scientific Inc. website—http://home.att.net/~payton-scientific/page14.html, pp. 1–2, date of publication unknown (downloaded Jul. 21, 1999.

Payton Scientific Inc. website—http://home.att.net/~payton-scientific/page7.html, pp. 1–2, date of publication unknown (downloaded Jul. 21, 1999).

Payton Scientific Inc. website—http://home.att.net/~payton-scientific/page8.html, pp. 1–2, date of publication unknown (downloaded Jul. 21, 1999).

Payton Scientific Inc. website—http://home.att.net/~payton-scientific/index.html, pp. 1–3, date of publication unknown (downloaded Jul. 21, 1999).

Rofin Forensic Product website—http://rofin.com.au/pr-f-p.htm, pp. 1–8, date of publication unknown (downloaded Jul. 6, 1999).

Sharp, P.A. et al., (1973), "Detection of Two Restriction Endonucleases Activities in *Haemophilus parainfluenzae* Using Analytical Agarose–Ethidium Bromide Electrophoresis," *Biochemistry* 12(16):3055–3063.

Stoilovic, Milutin, (1991), "Detection of Semen and Blood Stains Using Polilight as a Light Source," *Forensic Science International* 51:289–296.

Ünlü et al., (Oct. 1997), "Difference gel electrophoresis: A single gel method for detecting changes in protein extracts," *Electrophoresis* 18:2071–2077.

\* cited by examiner

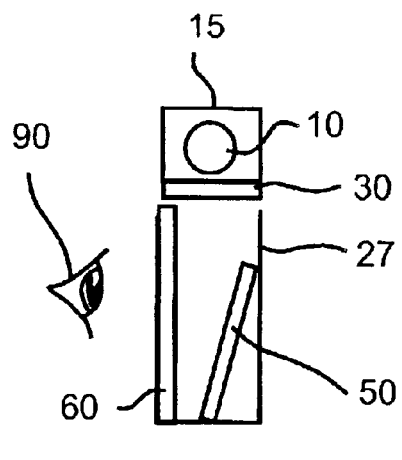
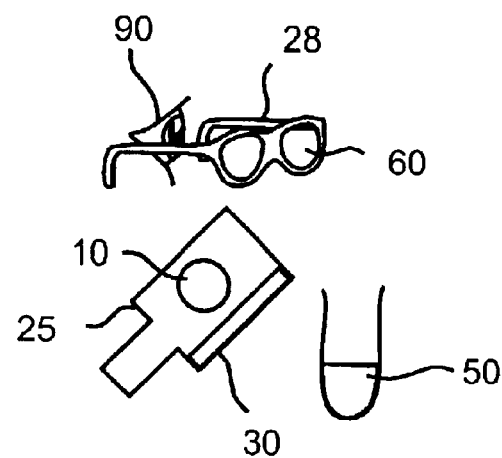
FIG. 17  FIG. 18
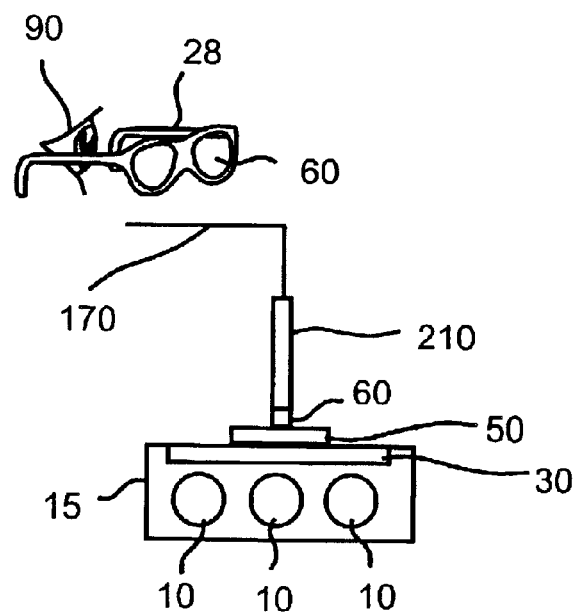
FIG. 19

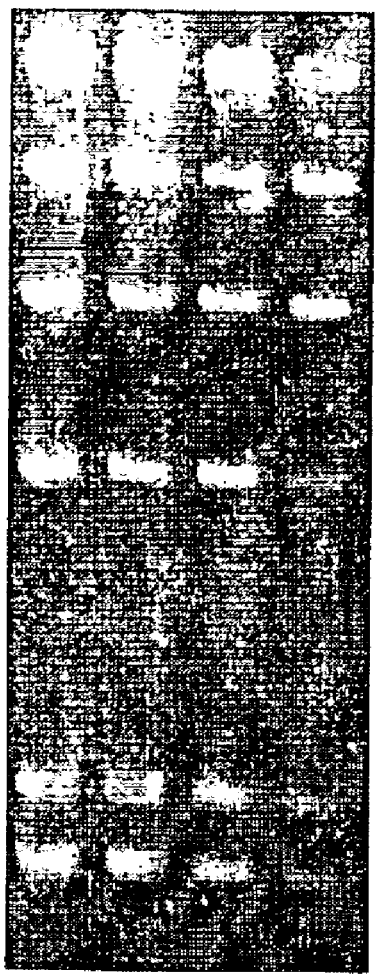 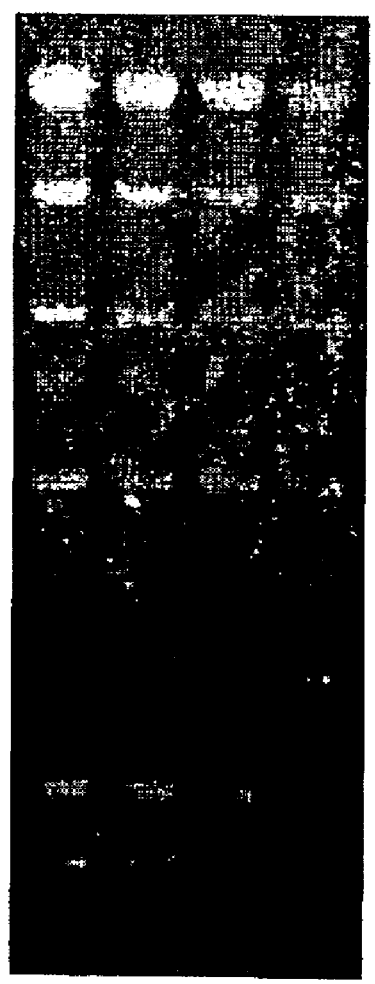
FIG. 23

32A — White

32B — Blue

32C — Blue-green

32D — Green

FIG. 32

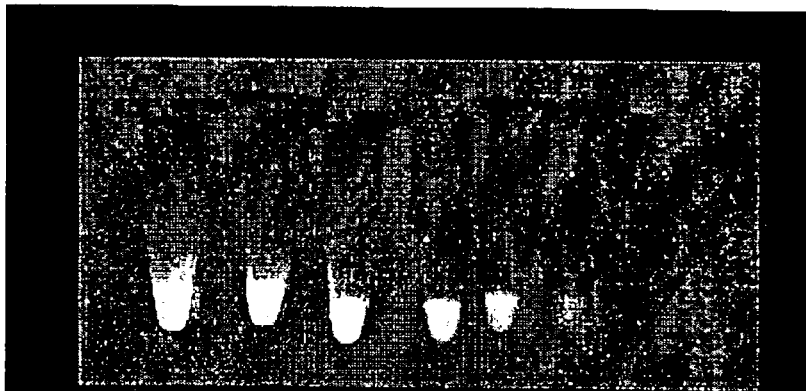 33A    white
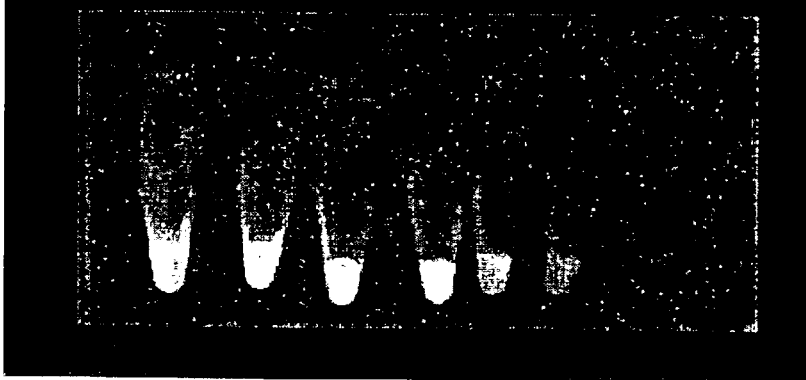 33B    blue
FIG. 33

FLUOROMETRIC DETECTION USING VISIBLE LIGHT

CROSS-REFERENCE TO RELATED APPLICATIONS

This application takes priority from U.S. Provisional Application No. 60/040,124, filed Mar. 7, 1997, and is a continuation-in-part of U.S. Ser. No. 09/753,783, filed Jan. 2, 2001, which is now U.S. Pat. No. 6,512,236, which is a continuation of U.S. Ser. No. 09/036,034, filed on Mar. 6, 1998, which is now U.S. Pat. No. 6,198,107, all of which are hereby incorporated by reference in their entireties to the extent not inconsistent herewith.

BACKGROUND OF THE INVENTION

The separation of DNA fragments by polyacrylamide or agarose gel electrophoresis is a well-established and widely used tool in molecular biology (Sharp, P. A. et al., "Detection of two restriction endonucleases activities in *Haemophilus parainfluenzae* using analytical agarose-ethidium bromide electrophoresis," (1973) Biochemistry 12:3055). The standard technique for viewing the positions of the separated fragments in a gel involves the use of an ultraviolet (UV) transilluminator (Brunk, C. F. and Simpson, L., "Comparison of various ultraviolet sources for fluorescent detection of ethidium bromide-DNA complexes in polyacrylamide gels," (1977) Analytical Biochemistry 82:455). This procedure involves first staining the gel with a fluorescent dye such as ethidium bromide or SYBR® Green I. The DNA fragments, which bind the dye, are then visualized by placing the gel on a light-box equipped with a UV lightsource. Typically the UV source, in combination with a built-in filter, provides light with an excitation maximum of around 254,300 or 360 nm. The UV light causes the DNA-bound dye to fluoresce in the red (ethidium bromide) or green (SYBR® Green I) regions of the visible light spectrum. The colored fluorescence allows visualization and localization of the DNA fragments in the gel. The visualization of DNA in a gel is used either to assess the success of a gene cloning reaction as judged by the size and number of DNA fragments present, or to identify a particular sized fragment which can be cut out from the gel and used in further reaction steps.

Transilluminators used in the art to visualize fluorophors are described in a number of patents, including U.S. Pat. Nos. 5,347,342, 5,387,801, 5,327,195, 4,657,655, and 4,071,883. Clinical examination of skin anomalies causing fluorescence have been described in U.S. Pat. No. 5,363,854 using visible light images as a control.

The use of UV light for viewing molecules in gels has two major disadvantages: (1) It is dangerous. The eyes are very sensitive to UV light and it is an absolute necessity that the viewer wear eye-protection, even for brief viewing periods, to prevent the possibility of serious damage. More prolonged exposure to UV light results in damage to the skin tissues (sunburn) and care must be taken to minimize skin exposure by wearing gloves, long-sleeved jackets and a full-face mask. (2) DNA samples are damaged by exposure to UV light. It has recently been documented by Epicentre Technologies that a 10–20 second exposure to 305 nm UV light on a transilluminator is sufficient to cause extensive damage to the DNA. This period of time is the absolute minimum required to excise a DNA band from a gel.

An alternative to UV transillumination involves the use of laser light sources. However, the use of laser light is not applicable to the simple and direct viewing of a DNA gel by the human eye. The extremely small cross-section of the laser light beam requires that a typical DNA gel be scanned by the laser, the fluorescence intensity at each point measured electronically and stored digitally before a composite picture of the DNA gel is assembled for viewing using computer software.

Visible light boxes for artists' uses are known to the art for visualizing non-fluorescing materials, e.g., as described in U.S. Pat. No. 3,802,102. The use of visible light to detect certain fluorescent dyes is suggested, e.g., in Lightools Research web page. However, no enabling disclosure for making such devices is provided. None of these references provides devices or systems for viewing fluorescence patterns using visible light.

Despite the recent development of dyes fluorescing in the visible spectrum (Haugland, R. [1996] "Handbook of Fluorescent Probes and Research Chemicals, Sixth Edition," Molecular Probes, Inc., Eugene, Oreg., pp. 13–18, 25–29, 29–35), transilluminators and other devices to take advantage of the properties of such dyes have not been made available to the public. It is an object of this invention to provide devices and methods for directly and indirectly viewing and measuring patterns of fluorescence not involving the use of UV transillumination but rather being capable of using sources of visible light such as ordinary lamps, as opposed to lasers and the focused lights used in standard fluorometers.

All publications referred to herein are incorporated by reference to the extent not inconsistent herewith.

SUMMARY

A visible light system is provided for detection of patterns of fluorescence emitted by fluorophors capable of emitting light of an emitted wavelength range (emission spectrum) when excited by light of an excitation wavelength range (excitation spectrum). In one embodiment, the excitation wavelength range must be different from the emitted wavelength range, although these ranges may overlap, and at least a portion of the non-overlapping portion of the emitted wavelength range must be within the visible spectrum. Both the exciting and emitted wavelength ranges are within the visible spectrum.

In preferred embodiments, using color filters, light of the "excitation type" for the fluorophor is light within the excitation wavelength range for the fluorophor, and light of the "emitted type" is light within the emitted wavelength range for the fluorophor. The first filter, or excitation filter, preferably transmits at least about 70% of the light from the light source in the excitation wavelength range, and the second filter, or emission filter, transmits at least about 95% of the light in the emitted wavelength range. Filters of the present invention may be constructed from any material that exhibits the necessary optical properties, namely transmittance. The first filter may be constructed from any material that substantially transmits light of the excitation type and substantially prevents transmission of light of the emitted type. The second filter may be constructed of any material that substantially transmits light of the emitted type and substantially prevents transmission of light of the excitation type. Filters of the present invention may exhibit constant transmission as a function of wavelength. Alternatively, filters of the present invention may have selectably adjustable transmission as a function of wavelength. For example, in a preferred embodiment the first filter, the second filter, or both, comprise liquid crystals having a transmission as a function of wavelength that may be changed upon the application of an electric potential. The term "filter" as used herein includes combinations of filters.

Preferred excitation filters in some applications are capable of substantially preventing transmission of light having wavelengths corresponding to a portion of or all the light emitted by the fluorophors or materials containing fluorophors. Preventing transmission of light from the excitation source having wavelength corresponding to the emission is beneficial as this light interferes with the separation and detection of light emitted from the fluorophors or material containing fluorophors. Preferred emission filters in some applications are capable of substantially preventing transmission of light having wavelengths corresponding to a portion of or all the light generated by the excitation source. Preventing transmission of light from the excitation source is beneficial as this light interferes with the separation and detection of light emitted from the fluorophors or material containing fluorophors. The phrase "substantially preventing transmission" refers to the ability of a material to prevent the transmission of some component of incident radiation. In a preferred embodiment, substantially preventing transmission refers to the ability of a material to prevent transmission of light having selected wavelengths resulting in a transmission of less than 1%. In a more preferred embodiment, substantially preventing transmission refers to the ability to prevent transmission of light having selected wavelengths resulting in a transmission of less than 0.1%.

The term "fluorophor" refers to a luminescent material that emits light upon the absorption of incident energy. Fluorophors of the present invention include materials that undergo fluorescence or phosphorescence. Fluorophors may be present in a variety of fluorophor-containing materials including tissue samples, gels, blood or other bodily fluid samples, food, beverages, organisms including genetically modified organisms, fluorescently stained or labeled DNA, and fluorescently stained or labeled proteins.

In other embodiments using polarizing filters, the first filter transmits the light from the source in a narrow range of orientations, and the second filter is oriented to exclude light from the source, i.e., transmits only light orthogonal to that passed by the first filter, so that only light emitted by the fluorophor passes through the second filter.

This invention comprises a visible light system comprising:
  a) a light source capable of producing visible light of the excitation type for the fluorophors;
  b) a first optical filter placed between said light source and said fluorophors, which is capable of transmitting light from said light source of the excitation type for said fluorophors and of preventing transmission of at least a portion of the light from said light source of said emitted type; and
  c) a second optical filter placed between said fluorophors and a light detector which second filter is capable of transmitting light of said emitted type and of preventing transmission of light from said light source of said excitation type, to form a viewable image of the pattern of fluorophors.

The fluorophors may be any fluorophors known or readily available to those skilled in the art, and are preferably used in the form of fluorophors bound to or in a biological sample. Fluorophors may be used to detect and quantify any desired substance to which they can be attached or into which they can be incorporated, e.g., organic molecules such as proteins, nucleic acids, carbohydrates, pigments, and dyes, inorganic molecules such as minerals, bacteria, eukaryotic cells, tissues and organisms. Fluorophors may also be an intrinsic part of an organism or substance to be detected, e.g., various dyes and pigments found in, for example, fungi, fish, bacteria and minerals.

The system of this invention may be incorporated into an integrated device such as a horizontal or vertical gel electrophoresis unit, scanner or other device in which detection of fluorescence is required. In a preferred embodiment comprising an enclosure for an electrophoresis gel, the filters of the present invention are integrated into a gel cassette, wherein the back plate of the cassette is the excitation filter and the front plate of the cassette is the emission filter. Alternatively, the back plate of the gel cassette may be transparent and the excitation filter is incorporated into the light source.

The devices and methods of this invention are especially useful for viewing patterns, i.e., two-dimensional and three-dimensional spatial arrangements of fluorophors. These patterns may comprise random spatial arrangements of fluorophors or spatial arrangements having reoccurring groups or series of fluorophors. Further, patterns viewable by the present invention include patterns that are substantially constant with respect to time or patterns that vary as a function of time. Patterns may comprise a single image corresponding to a single object or a plurality of images corresponding to a plurality of objects. Viewing of patterns of fluorophors in the present invention may be achieved by a detector comprising a human eye or by a detector comprising an instrument such as a charged coupled device, camera, array of photodiodes, array of photomultiplier tubes or any other equivalent detector. In an exemplary embodiment, a pattern of fluorescence is viewed by a computer or a robot operationally connected to a detector. Fluorescence detectors such as found in fluorometers are able to detect only the presence and intensity of fluorescence, and rather than generating an image generate a stream of data which must be interpreted by machine. The present invention allows direct viewing of two-dimensional (or three-dimensional) patterns of fluorophors by the human eye. Such patterns of fluorophors include the spatial arrangement of fluorophors on DNA on a gel, or of fluorophors on a TLC plate, the spatial distribution of fluorophors in test tubes in a rack, the spatial distribution of fluorophors in fungus or bacteria on skin, or on meat meant for human consumption, or the spatial arrangement of fluorescent fish in a tank. The images of patterns of fluorescence generated by the methods and devices of this invention may be viewed over time and may be photographed, digitized, stored and otherwise manipulated by machine but, in all cases, a two- or three-dimensional image is generated. The light source should not be a laser, and any mechanical detector used herein, like the human eye, preferably includes an array of photodetectors.

The term "light source" in the present invention refers to any light-emitting material that is capable of generating excitation radiation. Light sources of the present invention include but are not limited to photoluminescent light sources such as fluorescent and phosphorescent materials. For example, a light source of the present invention may comprise the combination of a light source and fluorescent material, such as a phosphor. Photoluminescent light sources of the present invention also include materials which undergo fluorescence energy transfer wherein energy is absorbed by an absorbing species and transferred to a radiating species which subsequently emits light. Light sources of the present invention also include chemiluminescent light sources and electroluminescent light sources, such as liquid crystal display sources and light emitting diodes. In a preferred embodiment, a phosphorescent light source of the present invention comprises a phosphor. Light sources of the present invention may further comprise diffusers, reflectors, light guides or other optical components well known in the art for providing excitation light having spatially uniform intensities. The light source of the present invention, however, should not be a laser.

For certain applications, light sources of the present invention are capable of generating light substantially free of ultraviolet light, particularly substantially free of light having wavelengths less than about 380 nm. In these applications, the light source should produce minimal light in the ultraviolet range, i.e., less than 1% of its light should be in the ultraviolet range, or the first filter should effectively screen out ultraviolet light, preferably to a level less than 1%, to prevent damage to DNA being viewed in the system. Even when using polarizing filters, a blue filter is preferably used as part of or in addition to the first filter to prevent DNA damage. Alternatively, the diffuser may be used to filter out residual UV light, and the diffuser and first filter can be combined into one sheet of material. (Most blue filters filter out ultraviolet light as well as visible light in wavelengths longer than blue.)

The phrase "substantially free of ultraviolet light" refers to the radiant output of a combination of a light source and excitation filter of the present invention. In a preferred embodiment, light substantially free of ultraviolet light refers to light having an intensity of ultraviolet light low enough as not to cause substantial damage to a fluorophor-containing material when illuminated for a reasonable time (e.g. less than 5 minutes).

The light detector or "viewer" used to detect the fluorescence of the fluorophor using this system may be a viewer's eye, or a device such as an optical scanner or charge coupled device camera for inputting a digitized image into a computer, or a camera. Such devices may also comprise means for quantifying the light within the emitted wavelength range reaching the viewer, and may also comprise means, such as a properly programmed computer as is known to the art, for converting such quantitative measurements to values for the amount of biological material present in the sample being measured.

The first filter is capable of filtering out light from the light source of the emitted type for the fluorophors. This means that at least some of the light from the light source of the emitted type is filtered out by the first filter. In many cases, the excitation and emission spectra for the fluorophors being used overlap. The first filter need only absorb light in a portion of the emission spectrum, usually the upper wavelength end thereof.

In some embodiments, the first filter may be an integral part of the support for the fluorophor or of the material or medium containing the fluorophor. For example, the first filter may serve as the gel support of a transilluminator device on which fluorophor-containing material in gel is placed. The gel itself, e.g., impregnated with pigment such as blue pigment, may serve as the first filter.

In some embodiments, as more fully described below, the second filter may be adapted to be placed over the human eye, e.g., as lenses for glasses to be worn by a human viewer, or may be adapted to be attached to the lens of an optical scanner or camera. The second filter may also serve as a safety lid for an electrophoresis unit or as a wall for the container for the fluorophor-containing material. The term "attached" in this context means both removably attached or built in as an integral part of a device. Also in some embodiments described below, the light source may be a handheld light source held behind the sample or preferably in front of the sample and at an angle to the viewer. The handheld unit for holding the light source also preferably comprises the first optical filter as part of the casing.

The fluorophor-containing material may be transparent or opaque, and the system may be configured to allow light from the light source to pass directly through the first filter, the fluorophor-containing material, and the second filter to reach the viewer in the case of a transparent medium, or to allow light from the light source to pass through the first filter to strike the fluorophor-containing material, allowing emitted light to "bounce" back from the medium toward the viewer, first passing through the second filter. The configuration of optical components may occupy any angle from just over 0° to 180°. The angle is that formed by lines drawn from the lamp to the sample and from the sample to the detector.

The term "transilluminator" as used herein means a device (other than a fluorometer requiring placement of fluorophor-labeled sample in a specially constructed sample holder) which allows light to shine through a surface in or on which a fluorophor-containing material has been placed, and includes horizontal electrophoresis devices and other devices in which fluorescent-containing materials are distributed on a surface.

Also provided are methods for making such systems and devices incorporating the light source and filters described above for viewing patterns of fluorescences emitted by fluorophors, said methods comprising:

(a) providing a light source capable of producing light in the visible spectrum;

(b) placing said fluorophors spaced apart from said light source;

(c) placing a first optical filter between said light source and said fluorophors, said filter being capable of transmitting light from said light source of the excitation type for said fluorophors and of preventing transmission of light from said light source of the emitted type for said fluorophors; and (d) placing a second optical filter between said fluorophors and a light detector, said second filter being capable of transmitting light of said emitted type and of preventing transmission of light from said light source of said excitation type.

Also provided are methods for viewing a pattern of fluorescence emitted by fluorophors capable of emitting light of an emitted type when excited by light of an excitation type different from said emitted type, at least a detectable portion of said emitted type being present in visible light, said method comprising:

(a) shining visible light on said fluorophors through a first optical filter which is capable of transmitting light of said excitation type and of preventing transmission of light of said emitted type, whereby said fluorophor emits light of said emitted type;

(b) passing light emitted by said fluorophor through a second optical filter which is capable of transmitting light of said emitted type and of absorbing light from the light source of said excitation type to form an image of said pattern of fluorescence; and (c) viewing said image.

Devices of this invention use visible rather than ultraviolet light for exciting and viewing fluorescence. Preferred embodiments of this invention using light sources of around 9 W emit even less dangerous UV light than standard fluorescent tubes used in most offices and laboratories. Using visible light allows the integrity of DNA being viewed to be maintained. The devices of this invention allow detection of as little as 0.1–1 ng of DNA, equal to or slightly better than a 312 nm UV transilluminator. Using a charge-coupled device (CCD) camera, it is possible to detect levels as low as tens of picograms of SYBR® Gold-stained DNA. Viewing may be done by eye or by an imaging device such as a camera or computer scanner using both conventional photography and digital imaging systems.

The optical characteristics of the present methods, devices and device components make the invention ideally suited for a wide range of applications including laboratory instrumentation, recreational goods, medical diagnostics and field sampling devices and methodologies. Particularly, the wavelengths, power and luminous flux of excitation radiation and fluorescence emission provide safe, efficient and low cost operation. Further, these optical characteristics provide design versatility allowing a great number of optical geometries and product constructs compatible to a wide variety of settings.

The optical characteristics of the excitation sources of the present invention provide substantial versatility in design and function, which make the present methods and devices compatible to a diverse range of operating conditions and commercial applications. First, use of excitation radiation substantially free of ultraviolet light, preferably having a wavelength greater than or equal to 380 nm and more preferably greater than or equal to 400 nm, avoids damage to fluorescent and phosphorescent materials induced by the absorption of high-energy ultraviolet radiation. For example, the excitation radiation of the present invention substantially reduces the occurrence of photo-bleaching, which is commonly observed upon excitation of fluorescent and phosphorescent materials with ultraviolet light. The present invention, therefore, provides efficient methods of exciting photolytically-labile and photosensitive compounds without substantially degrading or chemically modifying these materials. Reducing degradation and modification of fluorescent materials is beneficial because it increases the observed lifetime of fluorophors present in an illuminated sample and thereby provides fluorescent devices capable of repeatedly exciting a sample containing fluorescent materials for long periods of operation. Therefore, the present invention provides methods and devices for exciting fluorescence providing improved fluorophor longevity.

Second, use of fluorescence excitation radiation substantially free of ultraviolet light minimizes generation of harmful ultraviolet radiation. Ultraviolet radiation is a known hazard to most organisms and has been associated with the occurrence of erythema, degenerative and neoplastic changes in the skin, retinal damage and cataracts, and modification of the immunologic system of the skin. Ultraviolet light also is damaging to most materials including but not limited to plastics, glasses, and ceramics. As scattering occurs to some extent in almost every interaction of light waves and matter, scattered excitation radiation is unavoidable upon illumination of a sample containing fluorophors. The devices and methods of exciting fluorophors of the present invention, however, minimize scattered ultraviolet radiation by employing excitation radiation with very low intensities in the ultraviolet region. In a preferred embodiment, the intensity of light having wavelengths less than about 380 nm is less than about 1% of the total luminous intensity of the excitation source of the present invention. The methods and devices of exciting fluorescence of the present invention have the benefit, therefore, of reducing the exposure to ultraviolet light of the surroundings. Reference to "surroundings" in this context refers to all areas other than the intended illumination region. This benefit allows for embodiments of the present invention wherein scattered excitation radiation is in optical contact with the surroundings. Particularly, the present invention includes embodiments wherein scattered excitation radiation is in optical contact with the user, viewer or the user interface. This benefit also eliminates the need for costly and cumbersome light scattering sheaths and other light shielding devices employed to reduce the exposure of the surroundings to scattered excitation light.

Third, excitation with visible radiation also permits use of a wide class of materials for coupling an excitation beam to a sample containing fluorophors and for filtering light from and excitation source. Most materials efficiently absorb and scatter ultraviolet light. In contrast, a wide class of materials exhibits high transmittance throughout the visible spectrum, particularly from about 380 nm to about 800 nm. Accordingly, the devices and methods of exciting fluorophors of the present invention may employ optical components, such as filters, substrate holders and diffusion plates composed of a wide range of materials. Preferred materials for transmitting or filtering excitation radiation include ordinary glass, PYREX materials, gels, liquids and liquid crystals, and transparent plastics, such as polystyrene, polyethylene, acrylic, polymethylmethacrylate, polyimide, polycarbonate and polychlorotrifluoroethylene. Although these materials efficiently absorb and scatter ultraviolet radiation, they efficiently transmit light in the visible region of the electromagnetic spectrum. Further, these materials may be easily modified by the incorporation of pigments or other visible light-absorbing compounds to provide transmission of only selected wavelengths of light in the visible spectrum. Therefore, the methods, devices, and device components of the present invention are highly compatible with a wide range of optical materials. Particularly useful for the present invention are optical components constructed from transparent plastics, which may assume a great variety of shapes. The ability to use transparent plastics in the fabrication of devices of the present invention provides compatibility with a large number of product designs and allows for easy integration into a variety of instrumentation. Further, these materials are inexpensive and widely available, which substantially reduces fabrication costs. Moreover, the compatibility of the present invention with a wide range of optical materials avoids the need for optical components made of very costly UV-transparent materials.

Fourth, the present invention is capable of efficient excitation with very low power consumption. In this context, power consumption refers to the amount of power required to provide sufficient excitation of a fluorophor-containing material such that measurable fluorescence is observed. In an exemplary embodiment having a reflector operationally connected to the excitation source, the power consumption of an excitation source having an illumination surface area of about 550 $cm^2$ is about 9 W. In another exemplary embodiment having a reflector and diffuser operationally connected to the excitation source, the power consumption of an excitation source having an illumination surface area of about 1180 $cm^2$ is about 9 W. This is a significant improvement in power requirement over conventional ultraviolet fluorescence excitation sources, which have a power consumption of 60 W or more for comparable illumination surface areas. The low power consumption of exemplary fluorescence excitation sources of the present invention allows for inexpensive fabrication and low-cost operation of the devices and device components of the present invention. Further, the lower power consumption requirements of the present invention provide optical arrangements ideally suited for detection of fluorophor-containing materials in the field and other remote locations where the availability of power is limited. For example, the present invention provides effective methods and devices for field sampling in a variety of settings including but not limited to the detection of green fluorescent proteins in genetically modified crops, forensic detection of blood and other bodily fluids, the detection of bacterial and fungal contamination in meat and agricultural products, and the detection of environmental contaminants such as petrochemicals, pesticides and halogenated organic compounds.

Fifth, the present invention is capable of efficient excitation employing excitation sources having very low luminous fluxes. Use of excitation sources having low luminous fluxes is beneficial because it reduces the generation of scattered excitation radiation which substantially interferes with the separation and detection of emission. In addition, use of a low luminous flux substantially prevents problems associated with detector saturation. Further, employing low luminous fluxes for excitation substantially decreases exposure of the surrounding to scattered excitation radiation, particularly harmful ultraviolet radiation. In an exemplary embodiment, a measurable fluorescence signal is generated by employing an excitation source having a luminous flux less than or equal to about 0.072 W cm$^{-2}$.

The optical characteristics of the emission generated in the methods, devices and device components of the present invention also provide substantial versatility, which makes the invention highly compatible to a wide range of applications in diverse settings. The fluorescence generated in the present invention includes fluorescence having wavelengths in the visible spectrum, preferably ranging from about 380 nm to about 800 nm. Such emission is effectively detected by a wide range of detectors including but not limited to photomultiplier tubes, photodiodes, diode arrays, and photoconductive detectors. In addition, as light having a wavelength from about 380 nm to about 800 nm is detectable by the human eye, the present invention is capable of providing a variety of device constructs wherein the emitting fluorophor is directly interfaced with the user. Further, visible fluorescence is effectively transmitted and optically filtered by a variety of materials including but not limited to ordinary glass, gels, liquids, liquid crystals, PYREX materials, and transparent plastics, such as polystyrene, polyethylene, acrylic, polymethylmethacrylate, polyimide, polycarbonate and polychlorotrifluoroethylene. Therefore, the devices and methods of the present invention are compatible with a wide range of optical materials. In the present invention, optical components for filtering fluorescence may be constructed from transparent and semitransparent plastics, which may assume a great variety of shapes and may be easily integrated into a variety of instrumentation. For example, emission filters of the present invention are easily integrated into laboratory instrumentation, fish tanks, eyeglasses, scuba diving masks, drinking glasses and contact lenses. The versatility of materials and design constructs of the present invention substantially reduces fabrication costs of devices of the present invention.

BRIEF DESCRIPTION OF THE FIGURES

FIG. 17 shows a thin-layer chromatography apparatus in which the filters are an integral part of the apparatus, allowing fluorescent materials to be viewed during thin-layer chromatography.

FIG. 18 shows a handheld unit in combination with glasses worn by the viewer having as lenses the second optical filter.

FIG. 19 shows a transilluminator of this invention comprising a handheld second filter useful to manually scan fluorescent materials and quantitate amounts present.

FIG. 23 compares ethidium bromide-stained DNA gels on an ultraviolet transilluminator (left side) and on a transilluminator of this invention (right side).

FIG. 30A shows a spectrum for a white color setting. FIG. 30B shows a spectrum for a blue color setting. FIG. 30C shows a spectrum for a blue-green color setting. FIG. 30D shows a spectrum for a green color setting.

FIGS. 32A–D show images of fluorescent tetramethylrhodamine (TMR) samples obtained using LCD light sources for a variety of color settings. FIG. 32A shows the image obtained for a white color setting. FIG. 32B shows the image obtained using a blue color setting. FIG. 32C shows the image obtained using a blue-green color setting. FIG. 32D shows the image obtained using a green color setting. Each image shows six tubes containing a 2-fold dilution series of TMR. The tube on the far left contains 2.9 micromole/L solution and the sixth tube from the left contains 0.09 micromole/L solution. The tube on the far right contains buffer solution without TMR.

FIGS. 33A and 33B show images of fluorescent fluorescein (FL) samples obtained using LCD light sources for a two of color settings. FIG. 33A shows the image obtained for a white color setting. FIG. 33B shows the image obtained using a blue color setting. Each image shows six tubes containing a 2-fold dilution series of FL. The tube on the far left contains 6.0 micromole/L solution and the sixth tube from the left contains 0.19 micromole/L solution. The tube on the far right contains buffer solution without FL.

FIGS. 34A and 34B show spectra of LCD light sources having blue and white color settings, respectively. FIGS. 34C and 34D show background spectra corresponding to light detected upon positioning of excitation and emission filters without the presence of the fluorescein sample. FIG. 34C shows the background spectrum resulting from a LCD light source having a blue color setting and FIG. 34D shows the background spectrum resulting from a LCD light source having a white color setting. FIGS. 34E and 34F are spectra corresponding to the spectra of a 6 micromole/L fluorescein sample without any correction for the observed background. FIG. 34E shows the spectrum corresponding to a LCD detector having a blue color setting and FIG. 34F shows the spectrum corresponding to a LCD detector having a white color setting. Substantial infrared radiation is observed in the spectra in FIGS. 34C, 34D, 34E and 34F. FIGS. 34A and 34B correspond to detector collection times of 5 milliseconds and FIGS. 34C–F correspond to detector collection times of 5000 milliseconds.

FIG. 35A shows spectra of a bare halogen lamp (A) and an assembled halogen lamp (B). FIG. 35B shows the spectrum of a ultraviolet lamp. FIG. 35C shows the spectrum of an office lamp. FIG. 35D shows the spectrum of a blue fluorescent lamp light source of the present invention. Also shown in FIGS. 35A–D are the background spectra corresponding to each measurement.

As shown in FIG. 36, the blue fluorescent lamp generates the least amount of ultraviolet radiation.

FIG. 37A shows the fluorescence intensities of a protein lane not exposed to exciting radiation prior to analysis. FIG. 37B shows the fluorescence intensities of a protein lane exposed for eight minutes to exciting radiation generated by the methods of the present invention. FIG. 37C shows the fluorescence intensities of a protein lane exposed for eight minutes to exciting radiation generated by a 312 nm ultraviolet light transilluminator.

DETAILED DESCRIPTION

Figure 1:
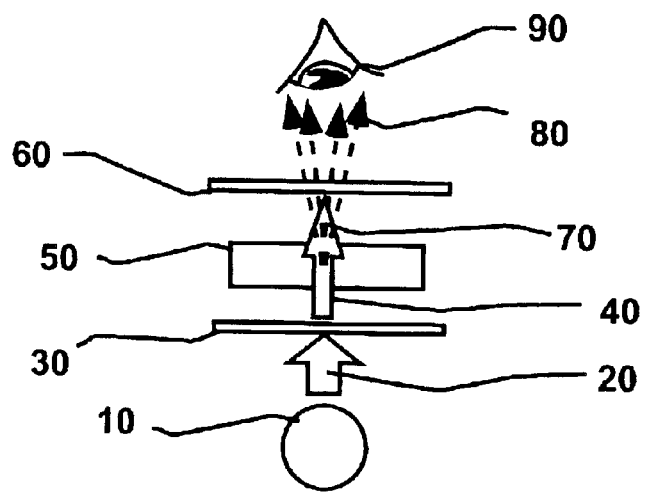
FIG. 1 is a scheme illustrating the operational principles of a device of this invention.

What the human eye perceives as "white light" consists of all the electromagnetic radiation with wavelengths between approximately 400 and 750 nm (the "visible spectrum"). (Light from 200–400 nm is called ultraviolet or UV.) Different wavelengths of light, when isolated, are seen by the human eye as being colored: light of wavelengths between 400–500 nm is generally seen as violet blue hues; 500–550 nm is seen as green/yellow hues; and 550–750 nm is seen as orange/red hues. The term "visible light" as used herein refers to light having wavelength(s) between about 400 nm and about 750 nm. Not all wavelengths in this range need to be present in the "visible light" for purposes of this invention.

Many dyes are excited to fluoresce by light within the visible spectrum. However, prior to the present invention, this fluorescence has not been used in transilluminators or in hand lamps because when white or broad-band visible light is used for excitation of the dye, the fluorescence is not detectable due to the large amount of incident light from the light source itself that reaches the observer or detecting instrument. This problem is overcome in the present invention by placing suitable optical filters on either side of the material to which the fluorophor is bound to prevent the totality of the lamp light from reaching the observer and allow the fluorescent light from the fluorophor to be seen.

"Optical filters" remove or "absorb," i.e., prevent transmission of, light of a certain type while allowing the passage or "transmittance" of light of another type. For example, a color filter that appears blue is absorbing most of the green and red light and transmitting the blue light. A color filter that appears amber is absorbing blue light and transmitting green and red light. The combination of green and red light appears yellow-orange to the eye, giving the filter a yellow-orange or amber color.

The exact optical properties of a color filter are due to the light absorption properties of the particular pigments embedded in its matrix. The filter matrix itself may be made from a wide range of materials known to the art and available to the skilled worker including plastics, such as acrylics, gelatin and glass.

Another type of optical filter is a polarizing filter. A polarizing filter transmits light of only a narrow range of orientations and prevents transmission of light of other orientations.

The optical properties of filters are measured in terms of either the "absorbance" or "percent transmittance." The terms are related as shown below:

$$A = -\log(\%T/100)$$

where A is the absorbance of the filter and % T is the percent transmittance.

"Fluorescence" is the phenomenon in which light energy ("exciting light") is absorbed by a molecule resulting in the molecule becoming "excited." (Lakowicz, J. R. (1983) "Principles of Fluorescence Spectroscopy," Plenum Press, New York.) After a very brief interval, the absorbed light energy is emitted by the excited molecule, usually at a longer wavelength than the exciting light. This emitted light is referred to as fluorescent light. A molecule that exhibits fluorescence or phosphorescence is referred to as a "fluorophor." Any given fluorophor will be excited to fluoresce more by some wavelengths of light than other wavelengths. The relationship between wavelengths of light and degree of excitation of a given fluorophor at that wavelength is described by the "excitation spectrum" of the fluorophor. The excitation spectrum is also called the "excitation wavelength range" herein.

Figure 2:
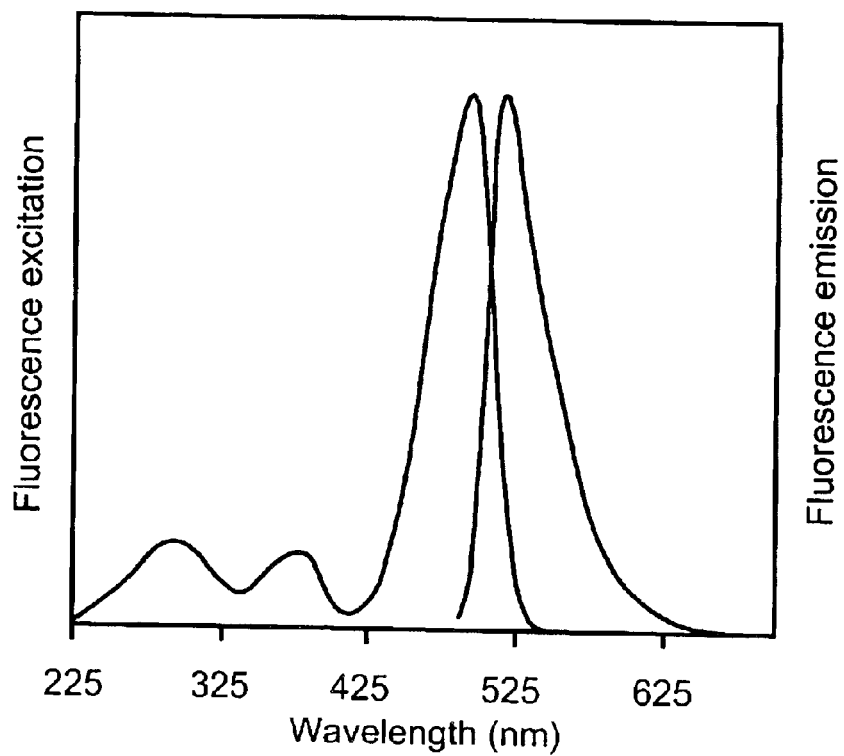
FIG. 2 is a graph showing the fluorescence excitation and emission spectra of a double-stranded DNA-bound SYBR® Green I nucleic acid gel stain.

Likewise, any given fluorophor will produce more intense fluorescence at particular wavelengths than others. The exact relationship between the wavelength of light and the intensity of the fluorescence emission at that wavelength is described by the "emission spectrum" or "fluorescence spectrum" of the fluorophor. The emission spectrum is also called the "emitted wavelength range" herein. FIG. 2 graphs the fluorescence excitation and emission spectra of a double-stranded DNA-bound SYBR® Green I nucleic acid gel stain as taken from R. Haugland (1996) "Handbook of Fluorescent Probes and Research Chemicals."

The excitation maximum is the wavelength of exciting light at which fluorescence of the fluorophor reaches maximum intensity. The emission maximum is the wavelength of light emitted by the excited fluorophor when its fluorescence is at maximum intensity.

Most fluorophors excited by and emitting visible light have an emission spectrum overlapping their excitation spectrum, although the maximum for each is different. The distance in nanometers between the excitation spectrum maximum and the emission spectrum maximum is known as the "Stokes' shift." Fluorophors with large Stokes' shifts in the visible range work best in this invention. For example, a fluorophor with an excitation maximum of 450 nm and an emission maximum of 600 nm with no overlapping between the spectra would be ideal; however most fluorophors have smaller Stokes' shifts. For example, SYBR® Orange has a Stokes' shift of 105 nm and SYBR® Gold has a Stokes' shift of 42 nm, while fluorescein has a Stokes' shift of 25 nm.

Figure 3:
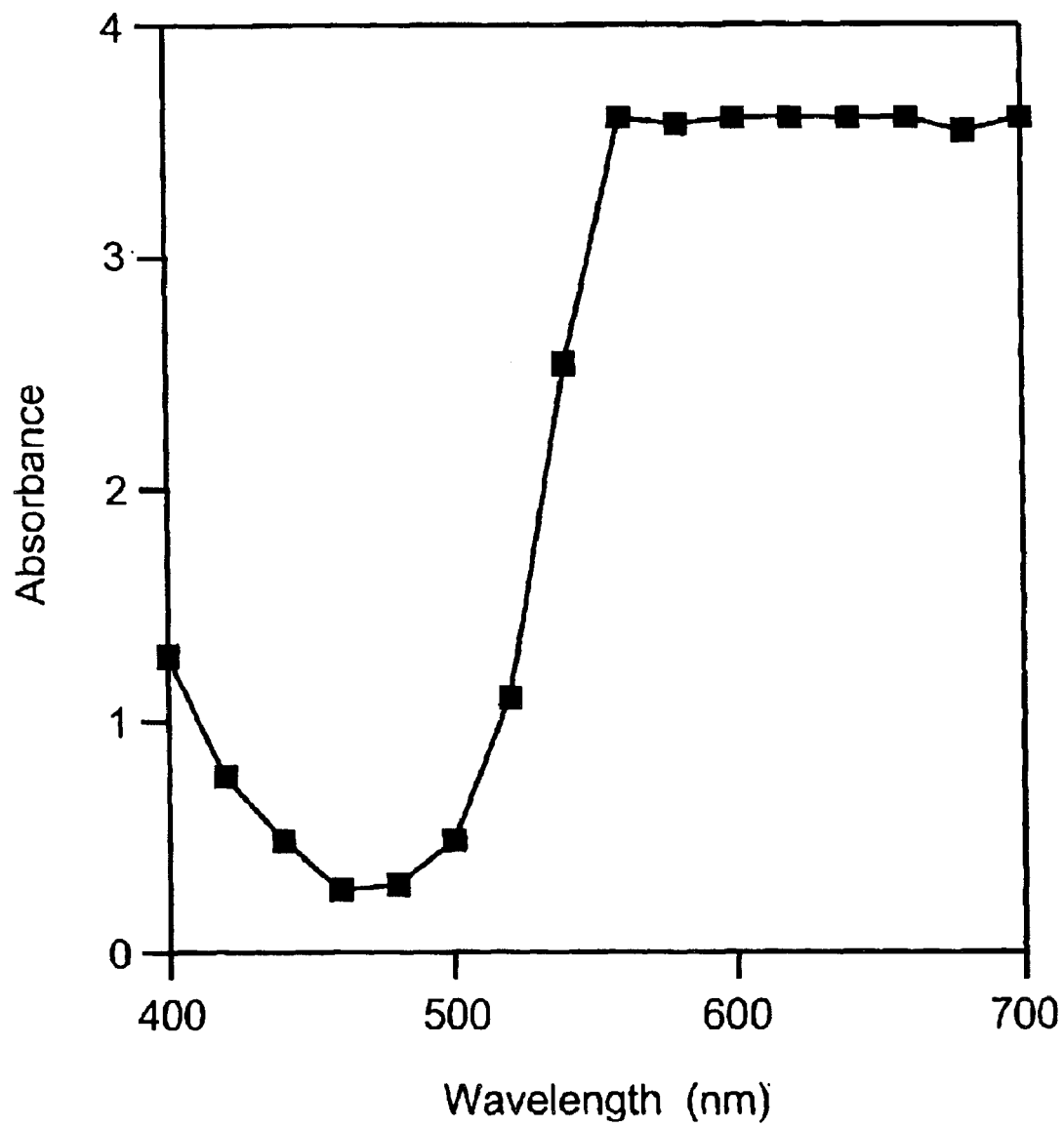
FIG. 3 shows the absorbance spectrum of the Acrylite #668-0GP optical filter used as a first optical filter in a preferred embodiment of this invention.
Figure 4:
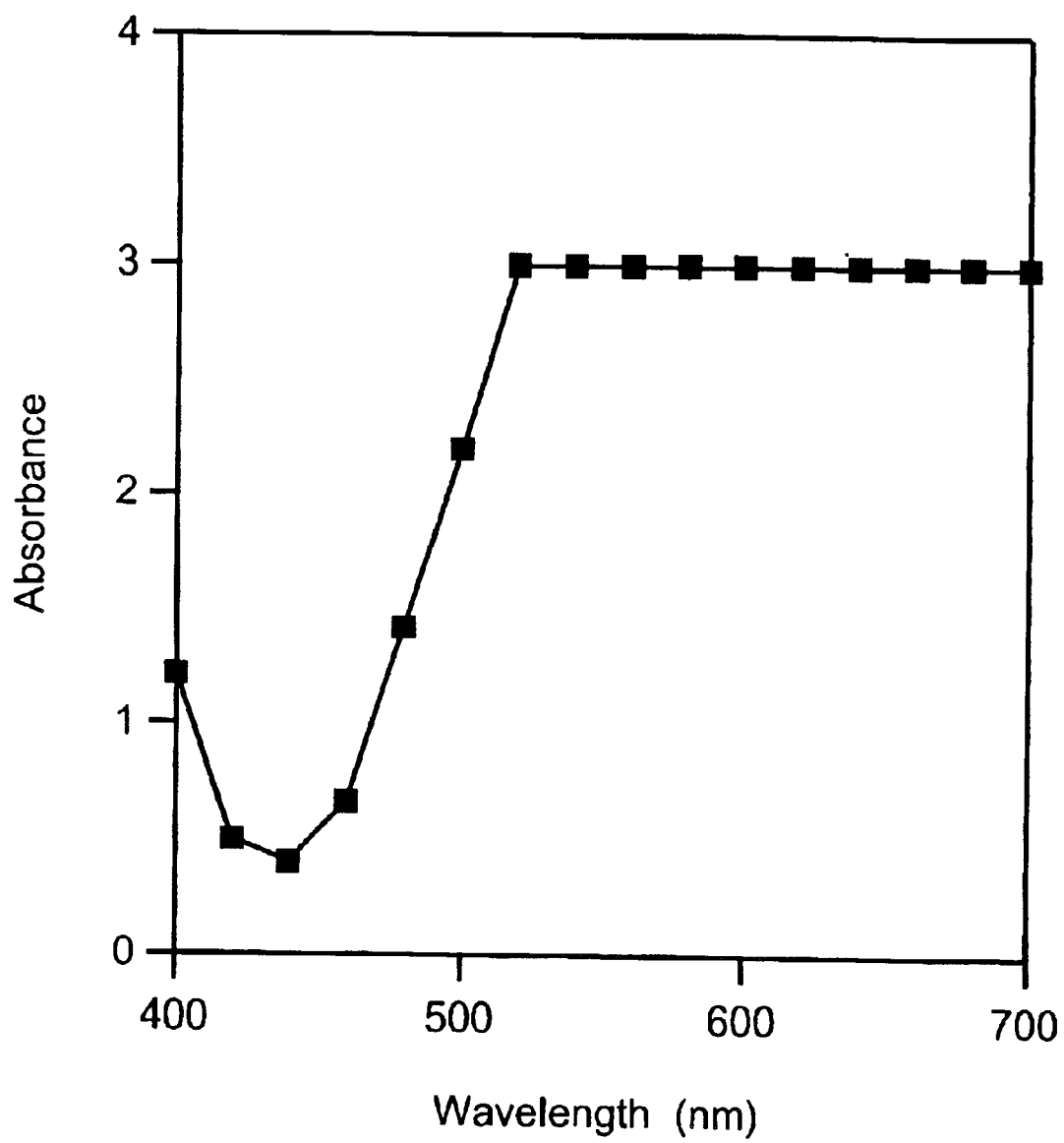
FIG. 4 shows the absorbance spectrum of the Wratten #98 optical filter used as a first optical filter in a preferred embodiment of this invention.

Visible light sources of this invention typically emit light which includes or overlaps both spectra. Most color filters do not sharply transmit light only within a certain wavelength, and sharply prevent transmission of all light outside this wavelength. Instead, as shown in FIGS. 3 and 4, most filters allow passage of a small quantity of light even at wavelengths where they are most effective as filters, and they prevent transmittance of a small quantity of light at wavelengths where they are least effective as filters for absorbing light. In a "crossover" wavelength range, the capability of such color filters to absorb light changes (gradually or sharply) along the wavelength scale from a region where maximum light is being absorbed, known as the "cut-off region," to a region where most of the light is being transmitted and only a small amount is being absorbed. As a practical matter, the light source will produce light in wavelengths overlapping those emitted by the fluorophor, and the filter between the fluorophor and the viewer used to transmit light in the emission spectrum will also allow enough light from the source to pass through to overwhelm the fluorescence (emitted spectrum). Thus a filter placed between the light source and the fluorophor to remove light from the source not removed by the filter between the fluorophor and the viewer must be used. To optimize the sensitivity of the system, filter pairs should be chosen so as to allow viewing of (a) the maximum fluorescence intensity and (b) minimum lamp light intensity. For typical fluorophors this involves a tradeoff between (a) and (b). The system can be adjusted to minimize lamp light intensity so that the lamp light does not overpower the fluorescence.

A first consideration is to choose the filter pairs so that in combination they prevent transmission of essentially all the exciting light to the viewer. To achieve this, assuming the lamp produces light as close to the excitation maximum of the fluorophor as possible: (a) the first filter must absorb as much light as possible in the emission spectrum of the fluorophor, i.e., in general the cut-off region must extend as far into the blue (shorter wavelengths) as practicable; and (b) the second filter must absorb as much light as possible in the excitation spectrum of the fluorophor, i.e., the cut-off region must extend as far into the red (longer wavelengths) as practicable. This tends to result in the use of filters whose crossover regions are far apart and not overlapping.

A second consideration for choosing the filter pairs is to maximize the amount of light in the emission spectrum for the fluorophor that reaches the viewer: (a) the first filter should be selected to transmit as much light as possible in the region of excitation maximum of the fluorophor; and (b) the second filter should be selected to transmit as much light as possible in the region of the emission maximum of the fluorophor. This tends to result in the use of filters whose crossover regions overlap. The point along the wavelength range where the absorbencies of the two filters coincide should be at as high an absorbency as practicable.

If the maximum of the emission spectrum for a fluorophor is greater than 500 nm, the absorbance of the filter selected to be placed between the fluorophor and the light source may rise to near 4 from less than 1 in a crossover region, e.g., from about 450 nm to about 500 nm. (Good filters have a crossover region of less than about 50 nm.) The absorbance of the second filter between the fluorophor and the viewer should then drop from near 4 to less than 1 in the same crossover region such that the sum of the absorbencies of the filters at wavelengths in the crossover region is near 4 to filter out most of the wavelengths in this region so that light below about 525 nm is effectively prevented from reaching the viewer. Thus the viewer sees substantially only light emitted by the fluorophor.

As discussed above, the excitation and emitted wavelength ranges of the fluorophor can overlap. The only requirement is that light of sufficient intensity to be detectable in a darkened space (preferably by the viewer's unaided eye but alternatively by an optical instrument such as a camera or optical scanner) be emitted by the fluorophor outside the excitation wavelength range so that it can be detected after light in the excitation wavelength range has been filtered out.

Typical fluorophors include many organic dyes. However, most molecules of biological origin such as nucleic acids, proteins, lipids and coenzymes are not strongly fluorescent. (Notable exceptions include Green Fluorescent Protein and its derivatives and various pigments such as chlorophyll and others used for coloration of plants and animals.) Therefore, to detect biological molecules it is usually necessary to either stain or react a biological sample with a fluorophor. "Staining" usually refers to the process in which a fluorescent dye binds relatively weakly to a target molecule without the formation of covalent bonds. If a fluorophor is "reacted" with a target molecule, this usually implies that the complex between the two species involves a relatively robust covalent bond.

The fluorescence intensity of a sample can be used either qualitatively to determine the presence or location of a fluorophor or quantitatively to determine the amount of fluorophor present. Variants on measuring the intensity of fluorescence include fluorescence resonance energy transfer and fluorescence polarization.

Alternatively, a fluorophor may be used indirectly to reveal the presence of a particular species. For example, the Vistra ECF Substrate system (Amersham Life Science Inc., Arlington Heights, Ill.) involves the use of the enzyme alkaline phosphatase, conjugated to an antibody that can bind specially prepared DNA oligonucleotide probes, to generate a fluorescent species. The enzymatic reaction generates multiple fluorophors, effectively providing an "amplified" fluorescence signal from the target DNA. Some examples of fluorophors used with biological samples are given in Table 1.

TABLE 1

| Dye | Excitation Maximum (nm) | Emission Maximum (nm) | Uses |
|---|---|---|---|
| ethidium bromide (EB)[1] | 518 | 605 | stain for nucleic acids |
| SYBR ® Green[2] | 494 | 521 | stain for nucleic acids |
| SYBR ® Orange[5] | 485 | 590 | stain for proteins |
| SYBR ® Gold[2] | 495 | 537 | stain for nucleic acids |
| GelStar ® 3 | 493 | 527 | stain for nucleic acids |
| Vistra ™ Green[4] | 497 | 520 | stain for nucleic acids |
| Vistra ™ ECF Substrate[4] | 440 | 560 | indirect detection |
| 4-chloro-7-nitrobenz-2-oxa-1,3-diazol[1] | 467 | 539 | covalent label |
| fluorescein[1] | 495 | 520 | covalent label |
| Texas Red ®[2] | 587 | 602 | covalent label |

[1]Available from Sigma Chemical Co., St. Louis, MO.
[2]Trademark of Molecular Probes, Inc. of Eugene, OR.
[3]Available from FMC Bioproducts, Rockland, ME.
[4]Available from Amersham Life Science Inc., Arlington Heights, IL.
[5]SYBR ® is a trademark of Molecular Probes, Inc. of Eugene, OR.

The removal of lamp light by filters so that the viewer sees substantially only the light emitted by the fluorophor is accomplished in two steps (see FIG. 1). In a preferred embodiment, a filter pair comprising a blue first filter and an amber second filter is used with a fluorophor such as SYBR® Green I or ethidium bromide that is maximally excited at around 500 nm or less (i.e., by blue light) and emits its maximum fluorescence at 500 nm or more (i.e., the fluorescence is green or red).

The first filter, which is blue, is placed between the light source and the fluorophor and absorbs the green and red components of the visible light and transmits only blue light through to the fluorophor. The blue light excites the fluorophor to fluoresce. Between the fluorophor and observer is placed a second filter, which is amber, that absorbs the blue light from the lamp but transmits the green or red fluorescent light from the fluorophor to the light detector, e.g., a human viewer or detection equipment.

Another embodiment uses polarizing filters. For a typical light source the light is polarized equally around all possible orientations. By placing a polarizing filter in front of a lamp it is possible to select light with a narrow range of orientations. If a second polarizing filter is placed on top of the first filter but orthogonal to the first, then this second filter will remove essentially all of the polarized light that has passed through the first filter. The net result is that no light reaches the viewer. When a fluorescent sample is placed on top of the first filter, the some of the sample will be excited by the polarized light that passes through the first filter. The sample will emit fluorescence. This fluorescence is also polarized. However, the emitted light will have a fairly broad distribution of orientations. Some of these orientations will be able to pass through the second filter and reach the viewer. The net result is that the fluorescence can be seen by the viewer against a dark background.

The "light source" used in this invention is any device capable of emitting visible light e.g., a typical household light such as a low-powered fluorescent tube or incandescent bulb that produces visible light including wavelengths within the excitation spectrum of the fluorophor. Different lamps produce different intensities of light at different wavelengths. Thus, for example, by altering the phosphor in a fluorescent tube, a lamp that will have maximum light output at wavelengths where excitation of the fluorophor is maximal may be manufactured. Some examples are given in Table 2.

TABLE 2

| Lamp | Maximum Output (nm) | Half width of Output (nm) | Relative Output at Maximum |
|---|---|---|---|
| Phillips F40B[1] | 460 | 160 | 0.19 |
| Interlectric F40T12/BBY[2] | 445 | 33 | 1.00 |
| Nichia NP-160[3] | 480 | 120 | 0.35 |
| Panasonic FPL28EB[4] | blue | | |
| Panasonic FML27EB[4] | blue | | |
| Sylvania CF9DS/blue[5] | 457 | 46 | |
| Dulux S9W Green[5] | 550* | 25 | |
| Dulux S9W Red[5] | red | | |

[1]Available from Phillips Lighting Co. of Somerset, NJ.
[2]Available from Interlectric Corporation, Warren, NJ.
[3]Available from Nichia America Corporation of Mountville, PA.
[4]Available from Matsushita Home and Commercial Products Company, Secaucus, NJ.
[5]Available from Osram Sylvania, Inc., Maybrook, NY.
*Main peak.

In an exemplary embodiment of the present invention, the light source comprises one or more light emitting diodes (LEDs). In some applications, use of light emitting diode light sources are preferred because of their low cost, low power consumption, small size and highly stable radiant output. Exemplary light emitting diode light sources of the present invention include but are not limited to LEDs manufactured by Agilent, such as HLMPCB15 (blue), HLMPCM15 (green), HLMPCE15 (blue-green), HLMPDB15 (deep blue), HLMAQL00T00 (orange), HLMTQG00T00 (red) and SSLLX5093XUWC (white).

The first optical filter is placed between the fluorophor and the light source and transmits light from the light source in the wavelength range of the excitation spectrum of the fluorophor. As most fluorophors useful with the invention are maximally excited between about 450 nm and 550 nm, the first optical filter will typically appear blue or 30 green to the eye.

It is essential the first optical filter also prevent the transmittance of (absorb) as much light as possible from the light source that is of similar wavelengths to the fluorescence emission of the fluorophor. A filter with a percent transmittance of around 0.01% at wavelengths in the emission spectrum of the fluorophor is desirable.

Examples of filters with these properties include Acrylite® #668-0GP, available from Cyro Industries of Rockaway, N.J. and Wratten #98, made by Eastman Kodak Company of Rochester, N.Y. FIG. 3 shows the absorbance spectrum of this Acrylite #668-0GP filter measured by an instrument capable of measuring absorbencies up to 3.5. FIG. 4 shows the absorbance spectrum of the Wratten #98 filter from the Kodak Photographic Filters Handbook. The data set does not extend above absorbencies of 3.0.

The second optical filter should transmit only light with wavelengths in the region of the fluorescence emission spectrum of the fluorophor. As most fluorophors useful with the invention have emission spectra between about 500 nm and about 650 nm, the second filter will typically appear yellow, amber or red to the eye.

Figure 5:
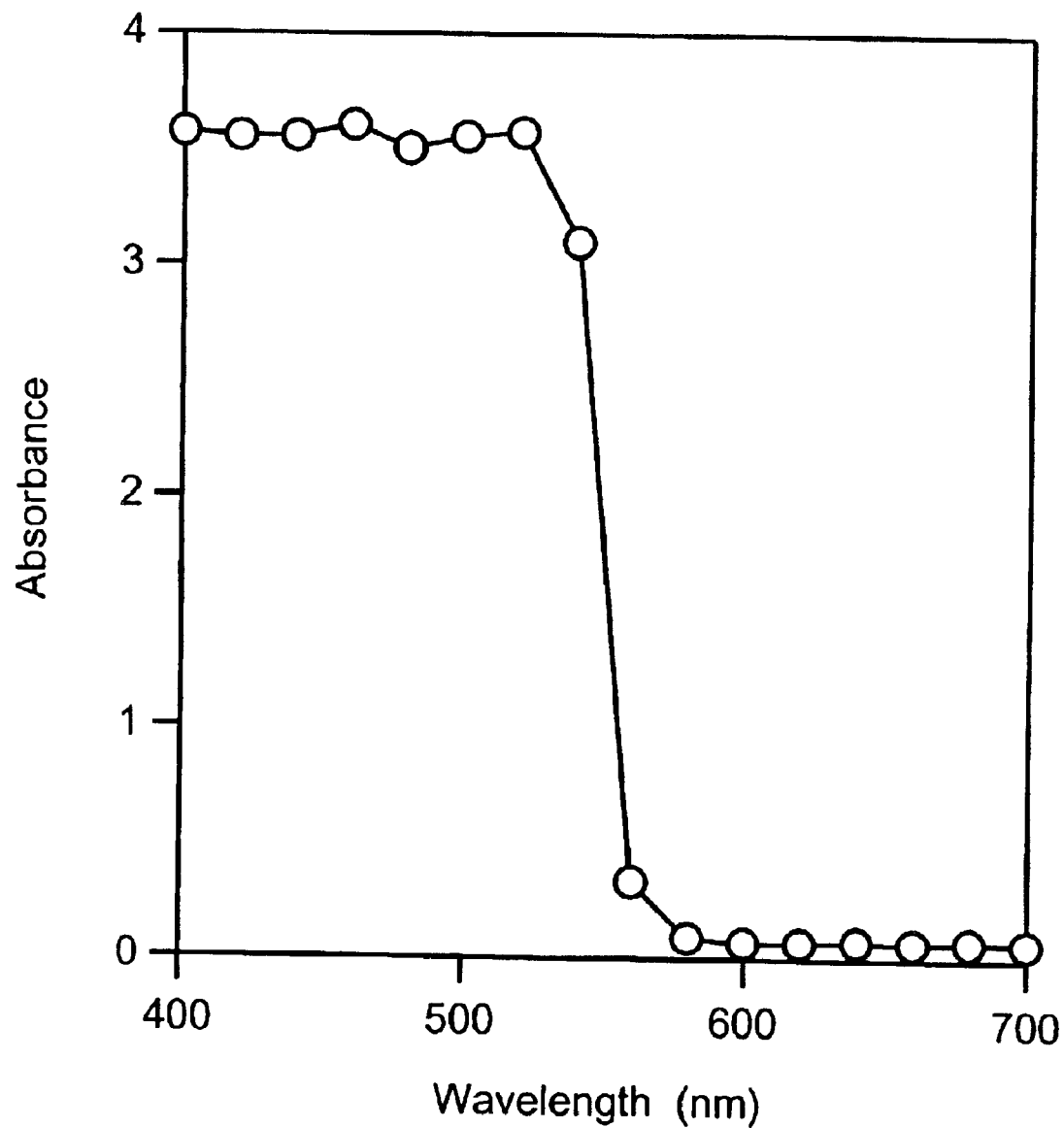
FIG. 5 shows the absorbance spectrum of the Perspex® #300 optical filter used as a second optical filter in a preferred embodiment of this invention.
Figure 6:
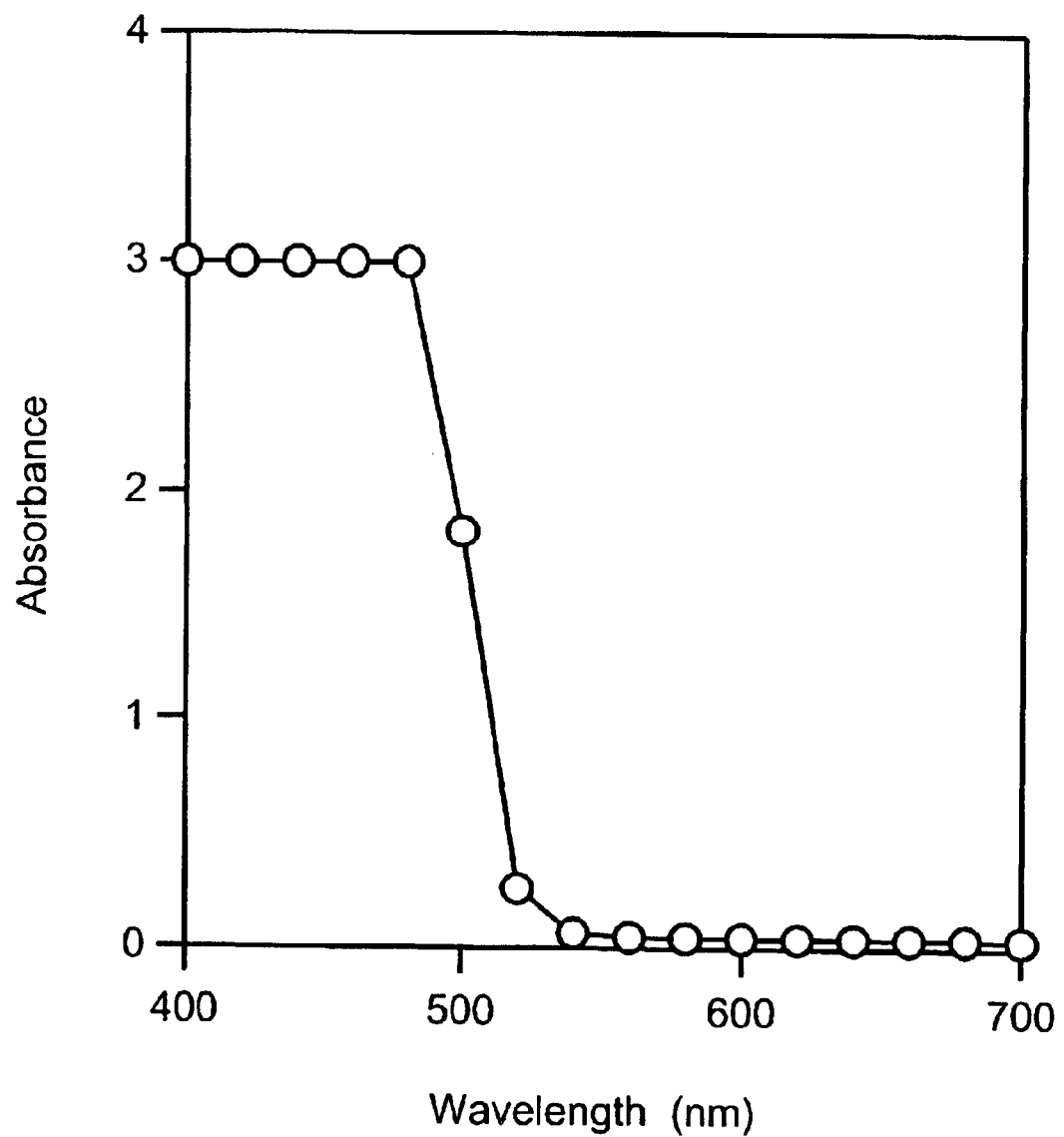
FIG. 6 shows the absorbance spectrum of the Wratten #12 optical filter used as a second optical filter in a preferred embodiment of this invention.

It is essential the second filter effectively prevent the transmittance of as much light as possible from the lamp that is transmitted by the first filter. For most fluorophors described herein, this means the second filter must absorb blue light. A filter with a percent transmittance of less than 0.1% in the blue region is desirable. Filters with these properties include Perspex® #300 made by ICI Chemicals and Polymers Limited of Darwen, Lancs., U.K. and Wratten #12 made by Eastman Kodak Company of Rochester, N.Y. FIG. 5 shows the absorbance spectrum of the Perspex® #300 filter measured by an instrument capable of measuring absorbencies up to 3.5. FIG. 6 shows the absorbance spectrum of the Wratten #12 filter from the Kodak Photographic Filters Handbook. The data set does not extend above absorbencies of 3.0. The Acrylite #408-5GP filter made by Cyro Industries of Rockaway, N.J., even though it has acceptable transmittance properties, should not be used alone due to intrinsic fluorescence.

In some cases, the use of two amber filters together may be desirable. For example, the combination of Wratten #12 with Lee #15, made by Lee Filters, Ltd. of Andover, Hampshire, U.K. can result in enhanced levels of fluorescence detection due to a decrease of the background light transmitted. In a somewhat different situation, the Acrylite #408-5GP filter, which possesses intrinsic fluorescence, can be used if a Lee #21 filter is placed between the #408 filter and the specimen. This effectively reduces the intrinsic fluorescence. Problems caused by intrinsic fluorescence of the filter may be alleviated by moving the filter farther away from the light source.

The transmittance properties of the two filters should cross over from high to low transmittance in the case of the blue filter and low to high in the case of the amber filter, as discussed above, in such a fashion that, in combination, the two filters prevent the transmittance of lamp light to the viewer.

Figure 7:
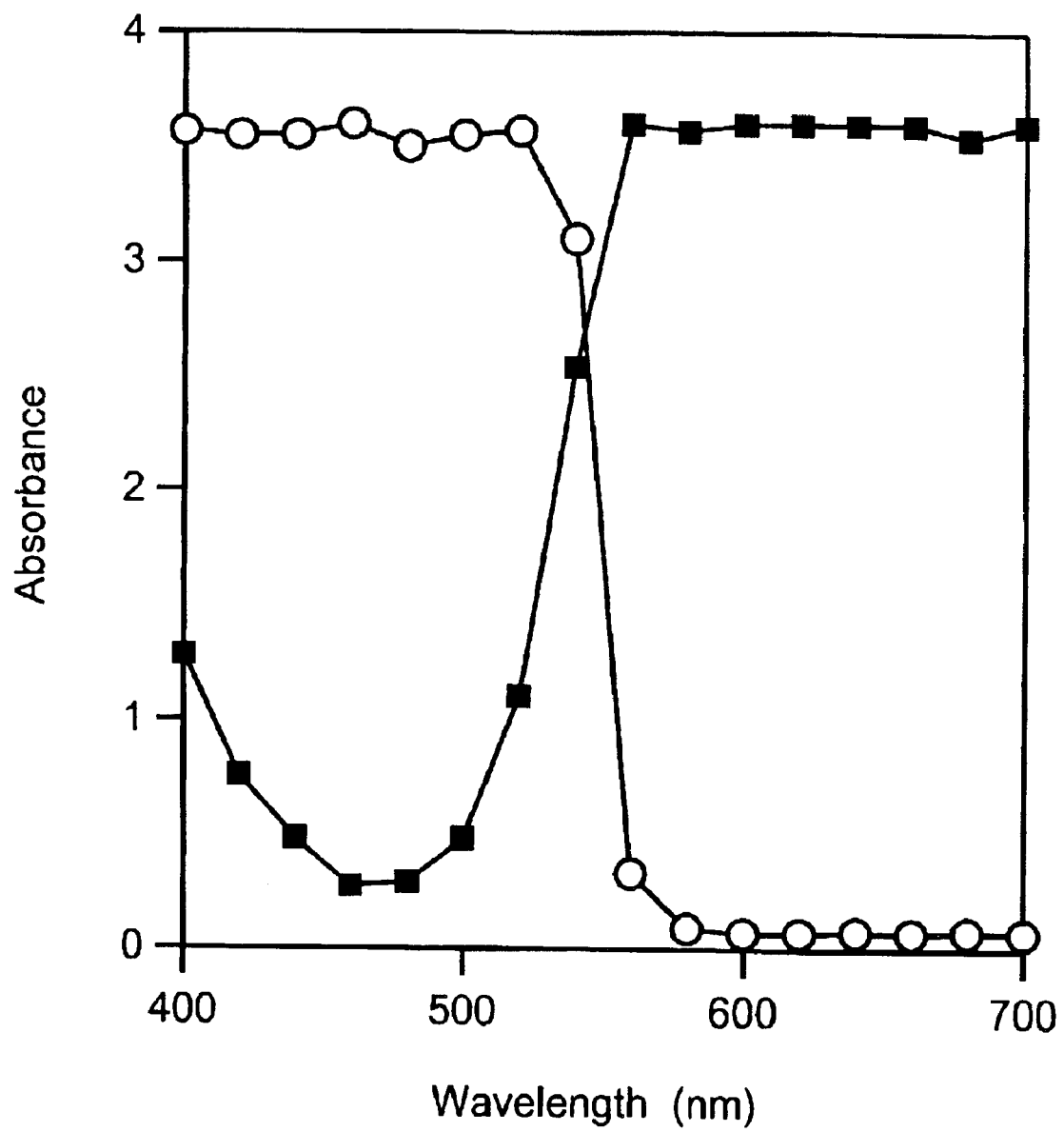
FIG. 7 shows absorbance spectra of the Acrylite #668-0GP and Perspex® #300 optical filters used as a combination of first and second filters in a preferred embodiment of this invention.
Figure 8:
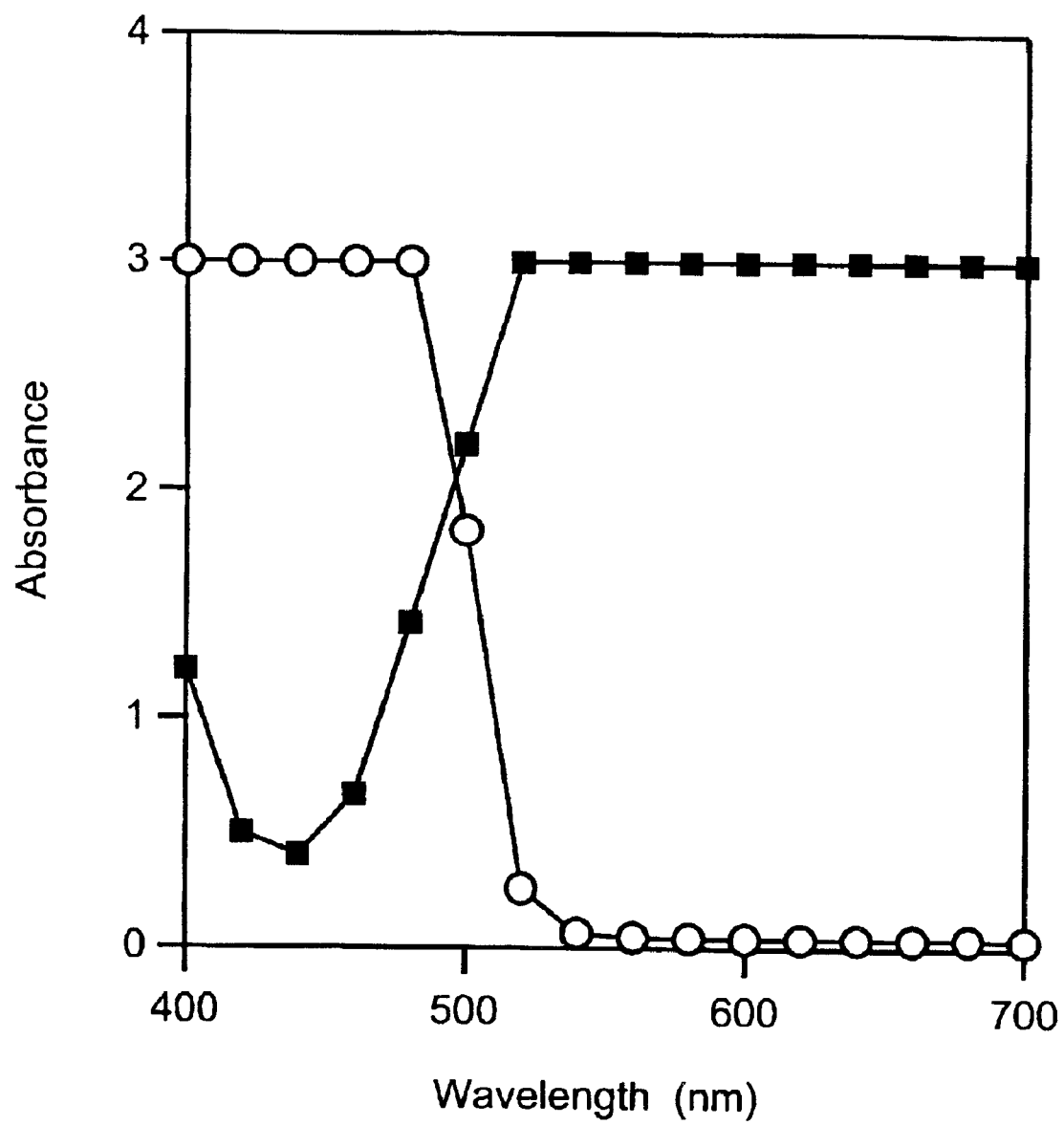
FIG. 8 shows absorbance spectra of the Wratten #98 and Wratten #12 optical filters used as a combination of first and second filters in a preferred embodiment of this invention.

Examples of useful filter combinations for this invention include Acrylite #668-0GP with Perspex® #300 (FIG. 7) and Wratten #98 with Wratten #12 (FIG. 8).

FIG. 1 is a scheme illustrating the operational principles of devices of this invention and is described with respect to preferred embodiments. A light source 10 such as a fluorescent lamp, shines broad-band visible light 20 indicated by the broad arrow onto a first optical filter 30 which removes wavelengths which do not activate fluorescent emission of the fluorophor contained on the fluorophor-containing material 50, which is typically a gel containing stained biological material. In a preferred embodiment, first filter 30 removes red and green light. After passing through filter 30, broad-band visible light 20 becomes light almost exclusively in the exciting wavelength range 40, in the preferred embodiment, blue light, indicated by the long, narrow arrow, some of which light passes through the fluorophor-containing material 50 and some of which strikes the fluorophor thereon causing it to emit light in the emission wavelength range which is mixed with a large excess of light in the exciting wavelength range to form mixed light 70, in the preferred embodiment, red or green light mixed with blue light. Mixed light 70 passes through second optical filter 60 where light in the exciting wavelength range (blue light) is removed leaving light in the emitting wavelength 80, in the preferred embodiment, red or green light, remaining to strike the light detector 90 which may be a human eye or a device such as an optical scanner or camera. In a preferred embodiment, light source 10 is contained within a light box 15 (see FIGS. 9–12), such as a conventional, commercially available visible light transilluminator. The light source 10 is preferably a fluorescent tube lamp or lamps of standard design, for example FPL28EB available from Matsushita Home and Commercial Products Company of Secaucus, N.J. or CF9DS/blue available from Osram Sylvania, Inc., Maybrook, N.Y. The sensitivity of the device may be enhanced by using lamps that provide the maximum light output in the region of the exciting light spectrum (between 450 and 500 nm in the preferred embodiment). First filter 30 is preferably a piece of semi-transparent material attached to the top of the light box 15 of sufficient size to cover the entire surface of the transilluminator. The optical properties of the sheet in the preferred embodiment are such as to allow through light of less than about 500–550 nm and cut off light of longer wavelengths. Any type of film or screen with these optical properties may be used. A preferred embodiment uses an Acrylite #668-0GP filter. The fluorophor-containing material 50 is preferably a fluorescently stained DNA gel. Second optical filter 60 may be in the form of a sheet directly over the gel or attached to an imaging device or in the form of lenses for glasses 28 (shown in FIG. 14). This filter 60 is a semi-transparent film or sheet that cuts off light of wavelengths less than the emitting wavelength range, or at least the emitting wavelength maximum, i.e., less than about 500–550 nm in the preferred embodiment, and allows through light of longer wavelengths. Any type of film or screen with these optical properties may be used. A preferred embodiment uses the Perspex® #300 filter. In an alternate embodiment, filter 60 is a narrow band pass filter or optical interference filter configured to efficiently pass emission from fluorophor-containing material 50. When the second filter 60 is a sheet, it is placed on top of the gel in the preferred embodiment, and is supported along the edges to avoid contact with the gel. This filter 60 may be attached to the light box by a hinge or other device known to the art if desired.

The light source can be of many types and incorporated into many structures. Any suitable source of light capable of illuminating the entire sample in the exciting wavelength range for the fluorophor being used may be employed as light source 10, for example a TV screen, photocopier, overhead projector, slide projector, camera flash, street light, strobe light, car headlight, computer scanner, light emitting material, or light-emitting diode may be used.

The systems of this invention may be used for both quantitative and qualitative analysis, detection, imaging, spectroscopy, chromatography, microscopy, DNA sequencing, cloning, polymerase chain reaction (PCR) processes, cell sorting, repair of DNA damage or mutation, e.g., due to aging or cancer, live animal studies, e.g., genetically altered mice containing the gene for green fluorescent protein, and the like, bacterial identification, detection and growth monitoring, medical diagnosis, e.g., detection of fungal infections on skin, industrial and environmental studies, mineral studies, and hobbies, e.g., the enjoyment of tropical fish and other tropical marine species that naturally contain fluorescent pigments.

In a preferred embodiment, an agarose or polyacrylamide gel in which DNA fragments have been previously separated by electrophoresis is stained with a suitable fluorescent dye such as ethidium bromide as described in a standard manual of laboratory techniques in molecular biology, or in the case of SYBR® Green I and SYBR® Gold, as described in the literature provided by Molecular Probes, Inc. of Eugene, Oreg.

The stained gel, referred to herein as the fluorophor-containing material 50, is placed on top of (in front of with respect to the viewer) first optical filter 30. The lamps or light sources 10 in the transilluminator are switched on. Either second optical filter 60 is placed over (in front of as defined by the viewer) the fluorophor-containing material 50, i.e., the gel, or glasses 28 as shown in FIG. 18, are put on by the human viewer.

Alternatively lenses designed to attach to an optical scanner or camera used as a viewer may embody second optical filter 60.

Figure 9:
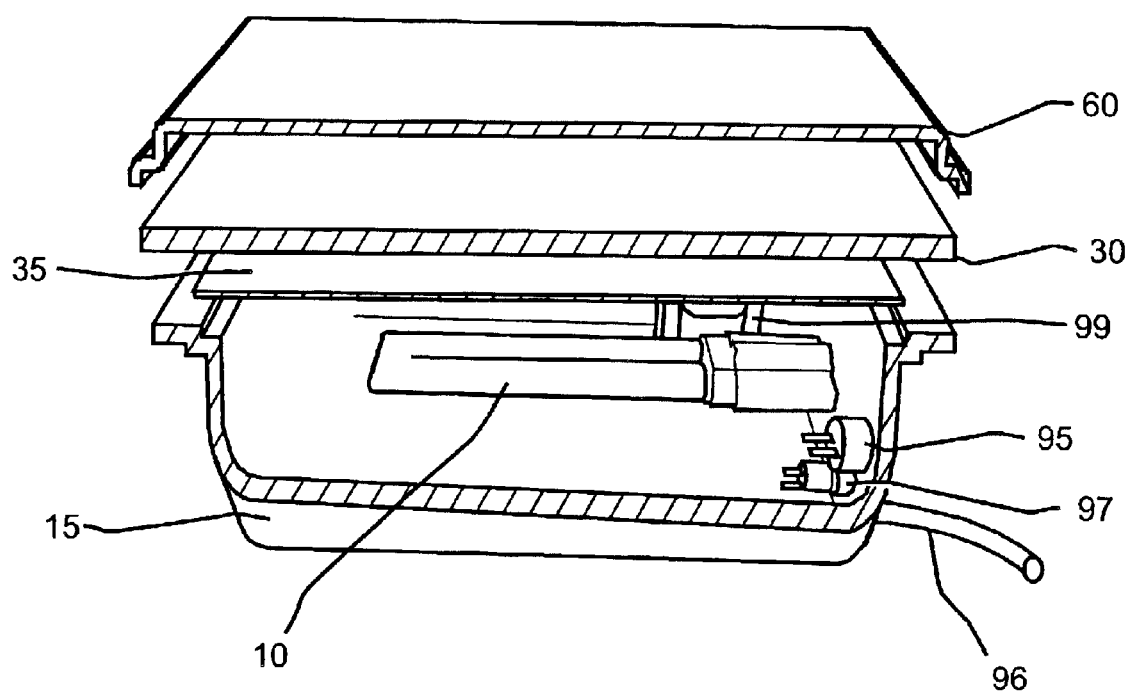
FIG. 9 is a cutaway and exploded view of a transilluminator device of this invention.

FIG. 9 is a cutaway view of a transilluminator device of this invention. Light box 15 contains electrical components, supports acrylic sheets and directs light as evenly and intensely out of the top as possible. The inside of the box is preferably made of a white plastic to reflect as much light as possible. The box preferably has curved edges and a reflector under the lamp to aid reflection. The sides are angled to aid light reflection. It is also substantially watertight and light-tight. Second optical filter 60 is preferably an amber screen comprised of Perspex® #300 acrylic which is designed to fit snugly over the top of the box and to drop down over the edge of first optical filter 30, which is preferably a blue screen. The overlap of second optical filter 60 over the edges of first optical filter 30 prevents light leakage and prevents second optical filter 60 from slipping off. For viewing by eye, the amber screen can be replaced by a pair of glasses with amber lenses. For viewing by instrument, the amber screen can be replaced by a small filter over the viewing instrument aperture. Other materials useful for the amber screen include 0.76 cm (0.3 in.) VSA orange vinyl from Northwest Laminating Company, Inc., of Seattle, Wash. and Wratten filter #21 from Eastman Kodak Co., Rochester, N.Y. The blue screen is preferably constructed from 0.635 cm (¼ in.) Cyro Industries 668-0GP acrylic, Rockaway, N.J. It is preferably attached to light box 15 in such a way that its top surface is free of joins, holes, screws, and the like to prevent corrosion by liquids. The screen may additionally be hardened to prevent scratching. It may also be hinged so that the transilluminator can be used as a white light transilluminator if desired. To be used in daylight or lit space, the transilluminator is equipped with a viewing box, i.e., a cover over the transilluminator through the top of which the samples can be viewed.

In a preferred embodiment, beneath the first optical filter, resting on a lip provided by flaring the vertical sides of the light box, is a diffuser screen 35 to provide as intense and even a light as possible across the surface area of first optical filter 30. Preferably, the diffuser screen 35 is made of 0.16 cm (¹⁄₁₆ in.) white acrylic, such as Acrylite #020-4 of Cyro Industries. Within light box 15 is disposed on/off switch 95, mains cable 96, and fuse 97. The device may be designed for AC or DC current. AC Ballast 99 is a magnetic ballast for the AC version of the lamp. Light source 10 may be a single 9 W 16.5 cm (6½ in.) blue compact fluorescent lamp CF9DS/blue from Osram/Sylvania, Inc., Maybrook, N.Y., attached to a vertical area of the back wall and centrally located to ensure even light distribution. A larger version of the transilluminator contains two 28 W fluorescent lamps (FDL28EB) available from Matsushita Home and Commercial Company, Secaucus, N.J. Alternatively, a 32 W blue fluorescent lamp may be employed.

Figure 10:
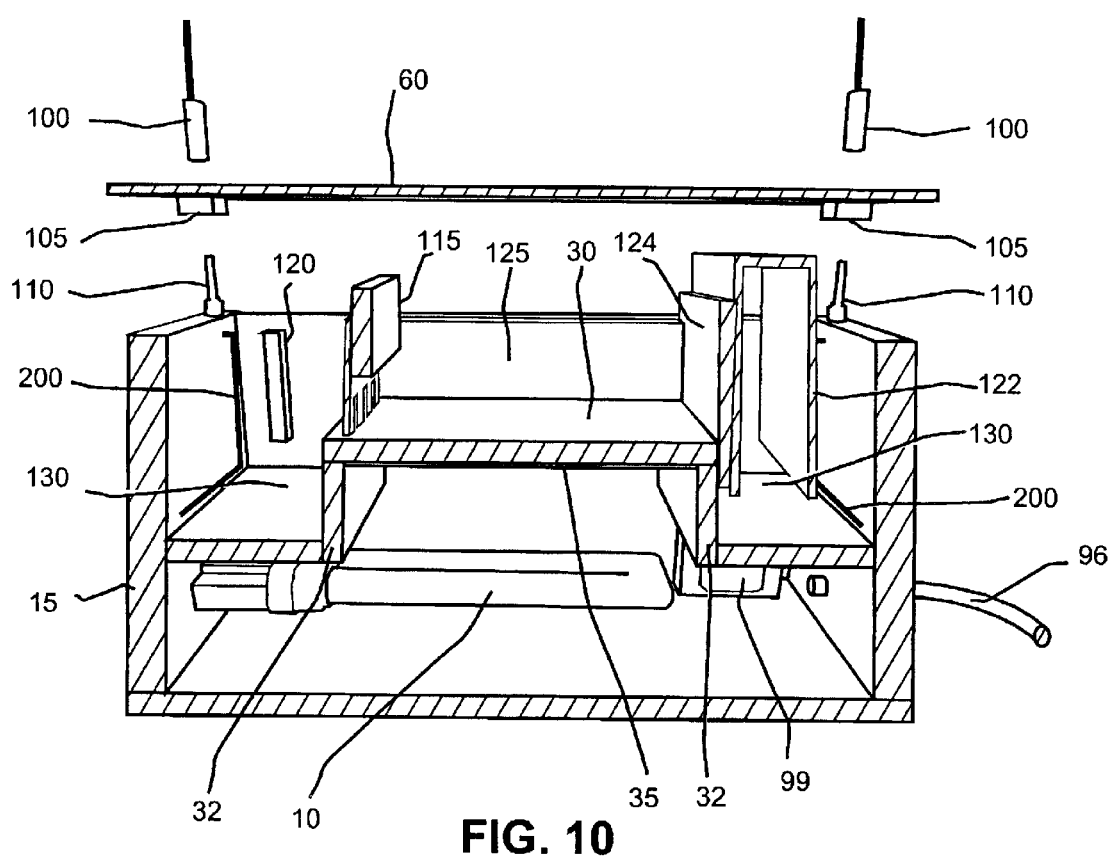
FIG. 10 is a cutaway view of an integrated transilluminator and horizontal electrophoresis unit of this invention.

FIG. 10 is a cutaway view of an integrated transilluminator and horizontal electrophoresis unit of this invention. The unit comprises female connectors 100 from a DC power supply (not shown), designed to mate with male connectors 110 placed behind or through second filter 60 which is separated from the main portion of light box 15 by blocks 105. The DC power supply via platinum electrode 200 supplies voltage across a gel to fractionate a DNA sample. The second filter also serves as a safety lid. First filter 30 also serves as a bed for the agarose gel which acts as fluorophor-containing material. Dam support strips 120 and dam support panel 125 support dam spring 122 which is made of plastic and squeezed to fit between dam support 120 and first filter support 32. TEFLON-coated foam 124 is attached to dam spring 122 so that it is forced against the first filter support 32 to form a water-tight seal. A similar dam (not shown) is placed on the left side of the device. The dams are used to contain the liquid agarose as it gels. Comb 115 functions to provide wells in the agarose gel into which samples may be loaded. Diffuser 35 is disposed between first filter 30 and light source 10 to spread the light evenly. Reservoirs 130 hold buffer. AC Ballast 99 for the light source is disposed beneath one of the reservoirs 130, connectable to an AC power supply via mains cable 96. Alternatively, the light source may be powered from a DC source.

In operation, a DNA sample is incubated with SYBR® Green I diluted 100- or 1000-fold in TAE, loading buffer is added and then the sample is loaded into a well in the agarose gel. The sample is then electrophoresed at around 100 V 50 mA. The light source is switched on. DNA fragments are viewed as they separate. Once a DNA band of interest is separated from the rest of the mixture, the electrophoresis can be stopped and the gel photographed and the band cut out if desired. For simple mixtures, different DNA bands become separated in minutes. Thus the device dramatically reduces standard "blind" UV electrophoresis time of about two hours. DNA samples can also be prestained, such as with ethidium bromide, and viewed as they fractionate.

Figure 11:
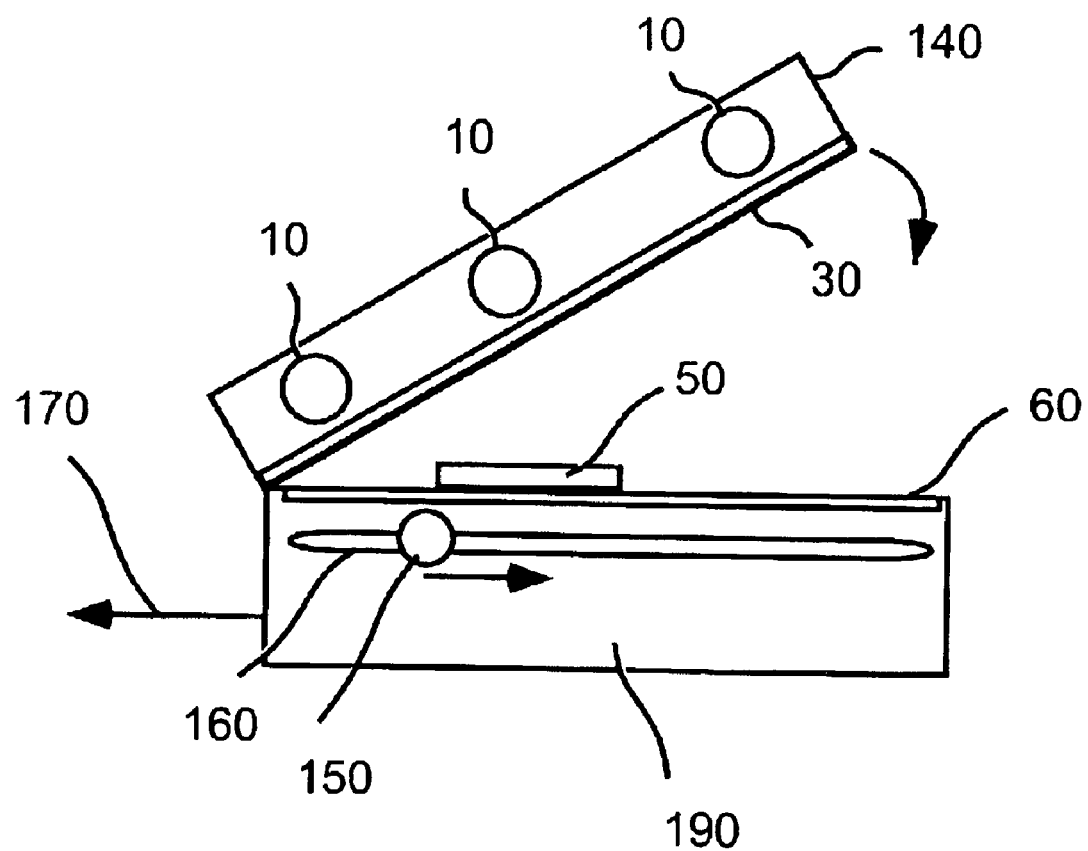
FIG. 11 is a side view of an integrated scanner-transilluminator device of this invention.

FIG. 11 shows a side view of an integrated scanner-transilluminator device of this invention using a modified commercially available scanner. Light sources 10 are contained within lid 140, as is first filter 30. This lid may be used to replace the standard transparency attachment on many scanners. Lid 140 is preferably rotatably connected, e.g., by means of hinges (not shown) to the photodetector container 190, the top surface of which comprises second filter 60 designed so the gel is not squashed when the lid 140 is lowered. Photodetectors 150 disposed within container 190 move on a track 160 or are moved by other means known to the art to scan a fluorophor-containing material 50 placed atop second filter 60. Photodetector container 190 also comprises means for detecting the fluorescent light and digitizing the scanned image (not shown) such as a processor comprising scanner software (not shown) known to the art, and digitalized image data 170 is sent to a computer (not shown) for analysis. Sensitivity of most commercially available scanners should be improved about 40-fold, e.g., by slowing the scan speed of the photodetectors 150, or by replacing the photo diode array with more sensitive means such as a charge-coupled device, for use in this invention.

Figure 12:
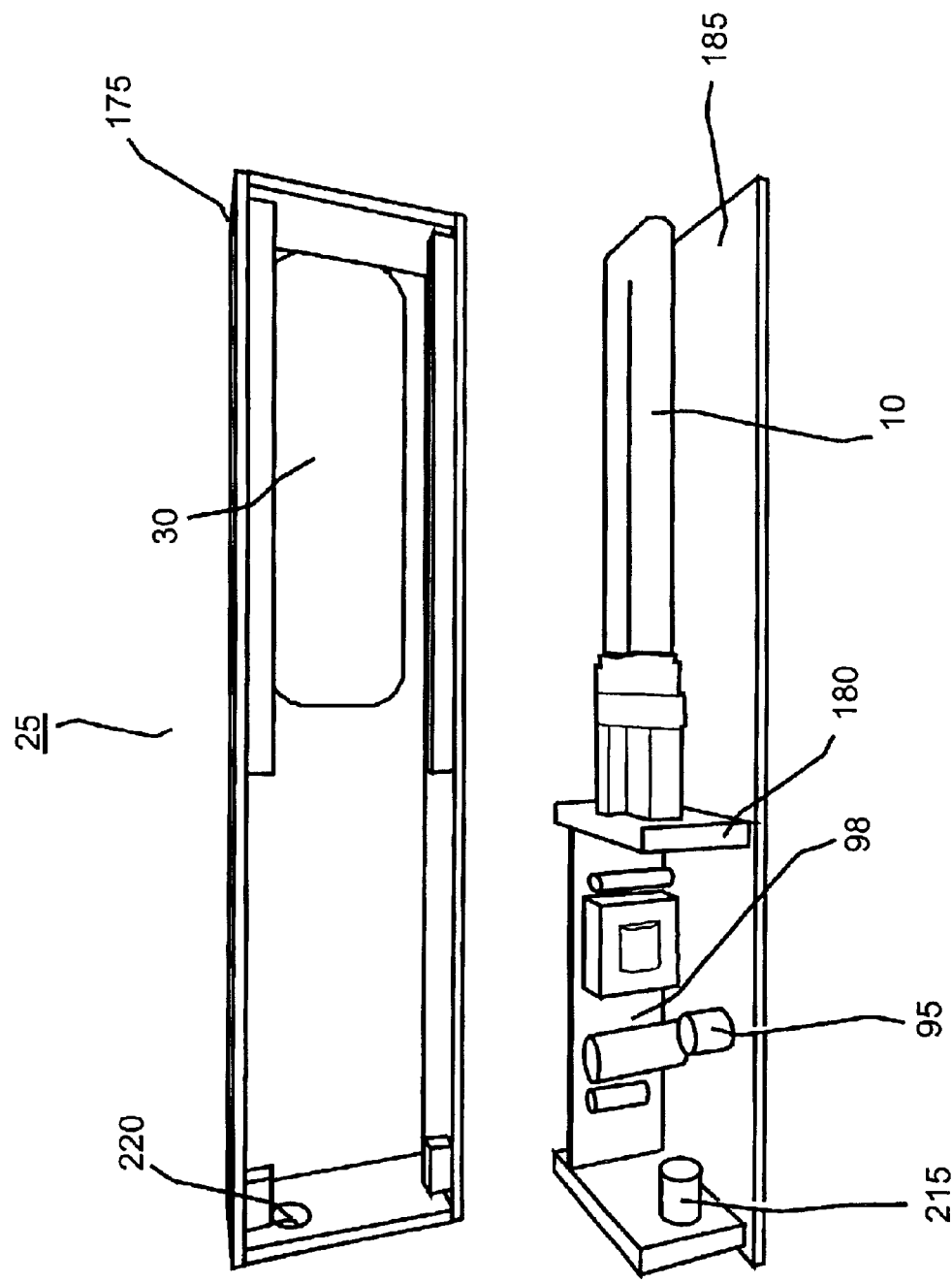
FIG. 12 is a perspective view of a handheld unit of this invention.

FIG. 12 is a perspective view of a handheld unit 25 of this invention designed for compactness so that the unit can be easily hand held. Preferably, the unit uses replaceable components, and in a preferred embodiment has dimensions of approximately (L×W×H): 27.9×6.35×3.8 cm (11×2.5×1.5 in). The unit comprises upper casing 175, containing first filter 30 and diffuser (not separately shown), on/off switch 95, DC ballast 98 and DC input socket 215. The light source 10 is removably mounted in lamp ballast mounting panel 180 in lower casing 185 designed to fit and be held by screws or latching means (not shown) into upper casing 175 so that first filter 30 is positioned directly over light source 10 when the unit is assembled. The unit also includes a DC input jack holder 220 to allow connection to a plug-in wall transformer to transform AC to DC.

The devices of this invention may be powered by AC or DC power using either a magnetic, electronic or DC ballast to drive the light sources. A 12-Volt DC power supply is preferred, as 12 V is significantly safer than 120 V. By connecting the unit to an AC power source through a plug-in wall transformer or the like capable of converting AC to DC, the unit can be made adaptable to differing types of AC power available anywhere in the world. Consequently, each assembled unit is internally identical. In addition, the unit may be powered by rechargeable batteries. Such a feature is particularly useful for a hand lamp, e.g., for use in hospitals and investigations of environmental features, e.g., at crime scenes and on or from other planets.

For increased sensitivity, lamps backed by reflective silver metallic linings to reflect light may be used. Lamps using different phosphors and shapes, and different wavelengths to optimize viewing of fluorescence may also be used, for example custom-manufactured lamps. The first optical filter may comprise separate regions for different viewing activities, e.g., viewing dyes with different fluorescent properties, and the second filter may comprise corresponding separate regions for viewing fluorescent species and colored stains as ordinarily viewed with a standard light box. The first filter may comprise slots or other means for assuring placement with respect to a light box or may comprise other holders for the light source. The first filter may also be rotatable in order to economize on the footprint of the unit. The second filter may be attached to the light box by a hinged top panel with slots for different filters if desired.

SYBR® Green and SYBR® Gold of Molecular Probes, Inc., of Eugene, Oreg. are preferred stains for DNA. They are more sensitive for detection of DNA than ethidium bromide and less mutagenic. In addition, if SYBR® Green is used as a pre-stain, the cost per gel is comparable to that of using ethidium bromide. This stain does not interfere with post-gel manipulations of stained DNA, and if necessary, can be removed by ethanol precipitation.

A preferred embodiment of the transilluminator of this invention comprises a 14×21 cm viewing surface convenient for viewing smaller size gels. Larger viewing surfaces, such as 28×42 cm may be used for multiple and extra large gels. It is economically feasible using this invention to make transilluminators that are far larger than known UV boxes, i.e., over four feet long.

An optimum configuration of the device can be defined as the configuration of lamp and filters that results, for any given fluorophor, in the maximum amount of fluorescence and the minimum amount of lamp light reaching the human viewer or detector.

The process of optimization begins with a consideration of the optical properties of the particular fluorophor to be detected:

(a) The lamp should produce its maximum light intensity at wavelengths within the excitation spectrum of the fluorophor.

(b) The first filter should transmit the maximum amount of light at wavelengths within the excitation spectrum of the fluorophor. Filters of the preferred embodiments hereof transmit over 70% light in this region.

(c) The second filter should transmit the maximum amount of light at wavelengths within the emission spectrum of the fluorophor. In practice, filters of the preferred embodiments hereof transmit over 95% of the light in this region.

At the same time that excitation light to, and emitted light from, the fluorophors are maximized, it is essential to keep the light from the lamp that reaches the viewer to a minimum. This involves the following considerations:

(a) A lamp that produces minimal light intensity outside the excitation region of the fluorophor.

(b) The first filter should absorb as much as possible of the lamp light with wavelengths outside the excitation spectrum of the fluorophor. Filters of the preferred embodiments hereof absorb about 99.99% of the light in this region.

(c) The second filter should absorb as much as possible of the lamp light with wavelengths outside of the emission spectrum of the fluorophor. Filters of the preferred embodiments hereof absorb about 99.9% of the light in this region.

(d) The absorbing wavelength regions of the two filters must cross over such that the sum of the absorbencies of the two filters in the crossover region results in as much as possible of the lamp light in this region being absorbed. In practice, the best filter combinations found so far absorb about 99.9% of the light in this region.

(e) If the first filter transmits lamp light in a region outside the excitation or emission regions of the fluorophor, then the second filter must absorb this light.

(f) If the second filter possesses intrinsic fluorescence, it should also comprise an auxiliary second filter placed between it and the light source to filter out light which excites it to fluoresce.

In optimizing the system for the detection of a particular fluorophor, a lamp containing a specially designed phosphor may be used, or filters containing specially designed pigments may be used, as may be readily made and assembled by one skilled in the art without undue experimentation.

Using readily available components, the following optimal configuration has been established for a light box to detect DNA fragments separated by gel electrophoresis and subsequently stained with SYBR® Green I or ethidium bromide:

(a) lamp: Panasonic FPL28EB (available from Matsushita Home and Commercial Products Company, Secaucus, N.J.) or Sylvania CF 9 DS/blue
(b) first filter: Acrylite #668-0GP
(c) second filter: Perspex® #300

With these components it is possible to construct a transilluminator that provides a comparable level of sensitivity for the detection of stained DNA to that of a conventional UV transilluminator, as described in the Example below (see Table 8). This configuration of lamp and filters is also appropriate for detecting other fluorophors with similar excitation and emission properties to SYBR® Green I and ethidium bromide, such as SYBR® Orange, Vistra Green, Vistra ECF substrate, GelStar, fluorescein and derivatives, and eosin and derivatives, and rhodamine and derivatives.

The principles described herein can be used to make a large number of different devices using various arrangements of the components.

Figure 13:
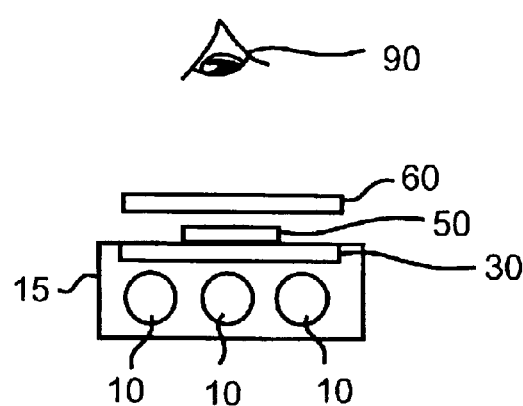
FIG. 13 shows a scheme for a transilluminator for viewing fluorescent materials in gels and other transparent media.

For example, FIG. 13 shows a scheme for a transilluminator for viewing fluorescent materials in gels and other transparent media. In this embodiment, light sources 10 and first optical filter 30 are contained in a holder or light box 15, atop which the fluorophor-containing material 50 is placed. Second optical filter 60 is placed over the fluorophor-containing material 50. Light in the exciting wavelength range hits first filter 30 to filter out other wavelengths, and passes into medium 50 causing fluorophors therein to fluoresce, emitting light in the emitted wavelength range which, mixed with light in the exciting wavelength range, passes through second optical filter 60 where light in the exciting wavelength range is filtered out, leaving substantially only light in the emitted wavelength range to strike the light detector 90.

Figure 14:
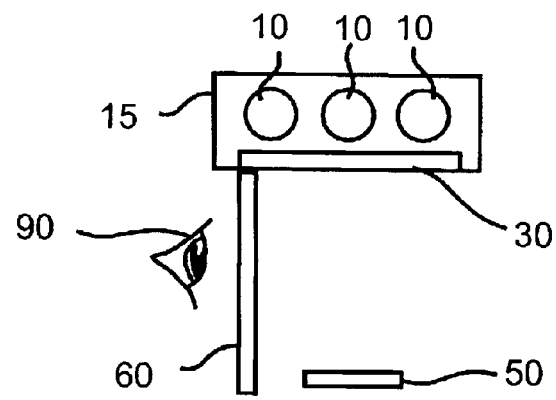
FIG. 14 shows a scheme for a top-illuminator for viewing fluorescent materials in opaque media such as thin-layer chromatography plates.

FIG. 14 shows a scheme for an epi-illuminator for top illumination for viewing fluorescent materials in opaque media such as thin-layer chromatography plates. In this instance, light from the light sources 10 held in light box 15 passes through first optical filter 30, to excite fluorophors in medium 50 to emit light in the emitted wavelength range which passes through second filter 60 placed at an angle (preferably, but not necessarily 90°) to first filter 30 for filtering out wavelengths other than those in the emitted wavelength range, after which the light in the emitted wavelength range strikes the light detector 90.

Figure 15:
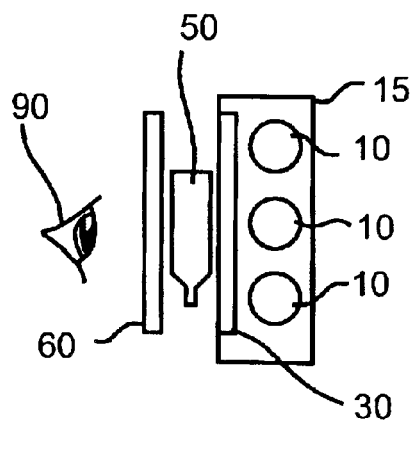
FIG. 15 shows a scheme for viewing the position of fluorescent materials during column chromatography.

FIG. 15 shows a scheme for viewing the position of fluorescent materials during column chromatography. In this case, a light box 15 containing light sources 10 and first filter 30 is placed next to the fluorophor-containing material 50, a column chromatograph. Second filter 60 is placed on the opposite side of the column. Light passes through the first filter 30, hits the column 50, and passes through second filter 60 to the light detector 90.

Figure 16:
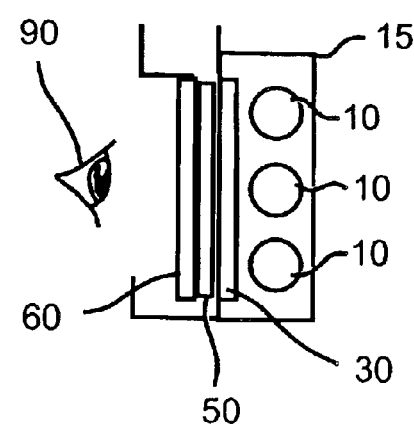
FIG. 16 shows a gel electrophoresis apparatus in which the two plates containing the gel also act as the two filters, allowing fluorescent materials to be viewed during electrophoresis.

FIG. 16 shows a gel electrophoresis apparatus in which the two plates containing the gel also act as the two filters, allowing fluorescent materials to be viewed continuously during electrophoresis. Light box 15 containing light sources 10 holds first filter 30 in place. First filter 30 and second filter 60 act as the two plates holding the gel, i.e., the fluorophor-containing material 50. The light detector 90 is placed so as to receive light passing from the light sources 10 through first filter 30, the fluorophor-containing material 50 and second filter 60. Preferably, the horizontal electrophoresis transilluminator of this invention has a footprint of about 25×10 cm and is the same size as an ordinary gel box. Since the viewer can continuously monitor the progress of a DNA fractionation, a gel only needs to be run until the DNA band(s) of interest are separated, thus in many cases, gel running times can be cut to fifteen to twenty minutes. In addition, DNA bands can be excised out of the gel in the electrophoresis unit, avoiding the danger of damaging the gel during transfer to a separate transilluminator.

FIG. 17 shows a thin-layer chromatography apparatus in which the filters are an integral part of the apparatus, allowing fluorescent materials to be viewed during thin-layer chromatography. In this case, first filter 30 is an integral part of light box 15 containing light source 10, which is detachably connected to container 27 into which the fluorophor-containing material 50 is placed. One side of container 27 comprises second filter 60. As in FIG. 11, light from light source 10 passes through first filter 30 to strike the fluorophor-containing material 50, and the fluorescence passes through second filter 60 and reaches the light detector 90.

FIG. 18 shows a handheld unit in combination with glasses 28 containing the second filter 60 worn by a human viewer. The eye of the viewer, or a mechanical light detector 90, is covered by a lens or lenses, shown as part of glasses 28 containing second filter 60. Light from light source 10 in handheld unit 25 passes through first filter 30 also comprised in handheld unit 25, then passes through the fluorophor-containing material 50 and second filter 60 comprised in glasses 28 to reach the viewer's eye or light detector 90. This embodiment is useful for a transparent medium. In alternative embodiments involving an opaque medium, the handheld unit 25 may be placed with respect to the fluorophor-containing material 50 so that light from light source 10 hits medium 50 and fluorescence emitted passes through to second filter 60 and light detector 90. The light source 10 may operate on DC or AC current. As a DC unit, handheld unit 25 may be powered by rechargeable batteries and thus run in remote locations if desired.

The handheld unit provides versatility for viewing fluorophors in both "open" systems such as agarose gels, nitrocellulose and polyvinyl difluoride (PVDF) membranes and thin layer chromatography (TLC) plates, as well as "closed" systems such as plastic and glass tubes, 96-well plates, chromatography columns, and sodium dodecyl sulfate polyacrylamide gel electrophoresis (SDS PAGE) gels and any kind of gel during electrophoresis. Using visible light, fluorophors can be viewed through a wide range of transparent or semi-transparent materials such as glass, polystyrene, polyethylene, polypropylene or acrylic. For example, in 1.5 mL polypropylene centrifuge tubes, using a handheld embodiment as described herein, fluorescein can be detected with eight times more sensitivity than using a UV lamp such that concentrations as low as 25 nmol/L may be detected, whereas using UV light at 360 and 312 nm, about 200 nmol/L is the lowest detectable concentration of fluorescein, and using UV light at 254 nm, over 1000 nmol/L of fluorescein must be present to be detected.

In "open" systems such as agarose gels, nitrocellulose membranes and TLC plates, fluorescein has been found to be detectable at very low concentrations. For example, on PVDF membranes, the visual detection limit is around 12 femtomoles of fluorescein, about twice the sensitivity achieved using UV light.

FIG. 19 shows a transilluminator of this invention comprising a light box 15 containing light sources 10 and first filter 30 atop which is placed the fluorophor-containing material 50. Handheld wand 210 comprising second filter 60 may be manually passed over the fluorophor-containing material 50 and sends image data 170 to a detector (not shown). The viewer 90, shown as a human eye wearing glasses also containing second filters 60, is able to directly view the fluorescence to aid in directing the wand over the fluorophor-containing material.

Figure 20:
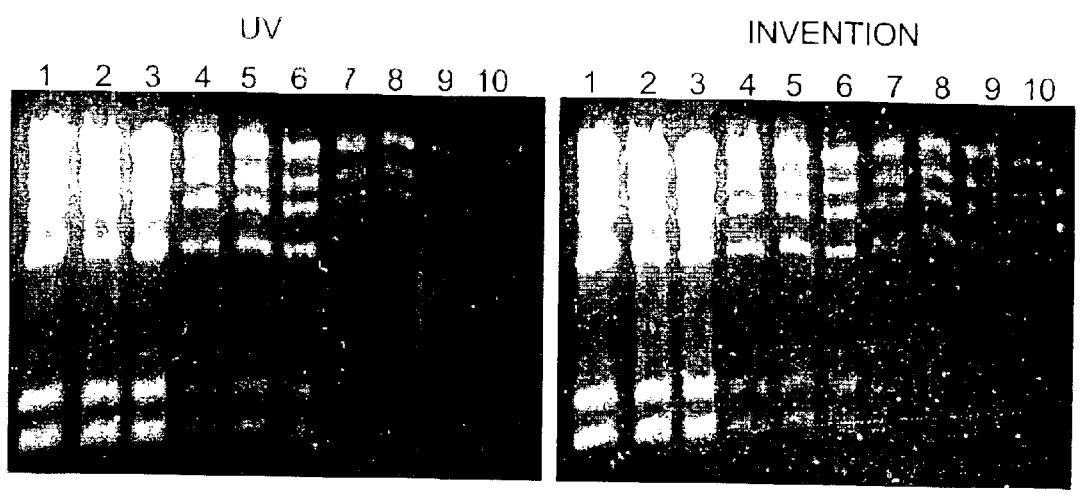
FIG. 20 compares SYBR® Gold-stained DNA gels on a 312 nm UV transilluminator and on a transilluminator of this invention.

FIG. 20 shows a gel comparing SYBR® Gold-stained DNA on a 312 nm UV transilluminator (left panel) and a transilluminator of this invention. Various amounts of λ DNA cut with HindIII were separated by gel electrophoresis and the gel stained with SYBR® Gold. The gels were then photographed on a 312 nm UV transilluminator (left) or a transilluminator of this invention (right). As can be seen, the transilluminator of this invention provides greater sensitivity.

Figure 21:
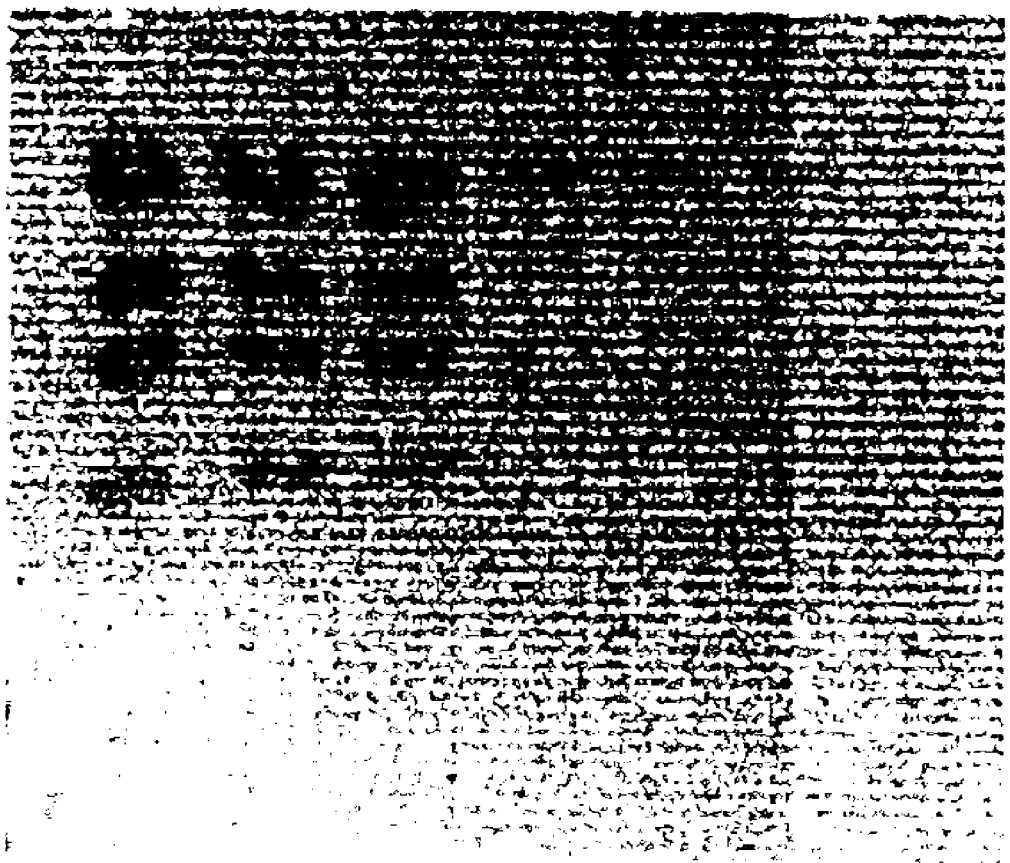
FIG. 21 shows a SYBR® Gold-stained DNA gel image captured by computer scanning.

FIG. 21 shows the SYBR® Gold gel of image shown in FIG. 20 (right side) made using a transilluminator of this invention and captured using a computer scanner. The original colored image was converted to grayscale and reversed.

Figure 22:
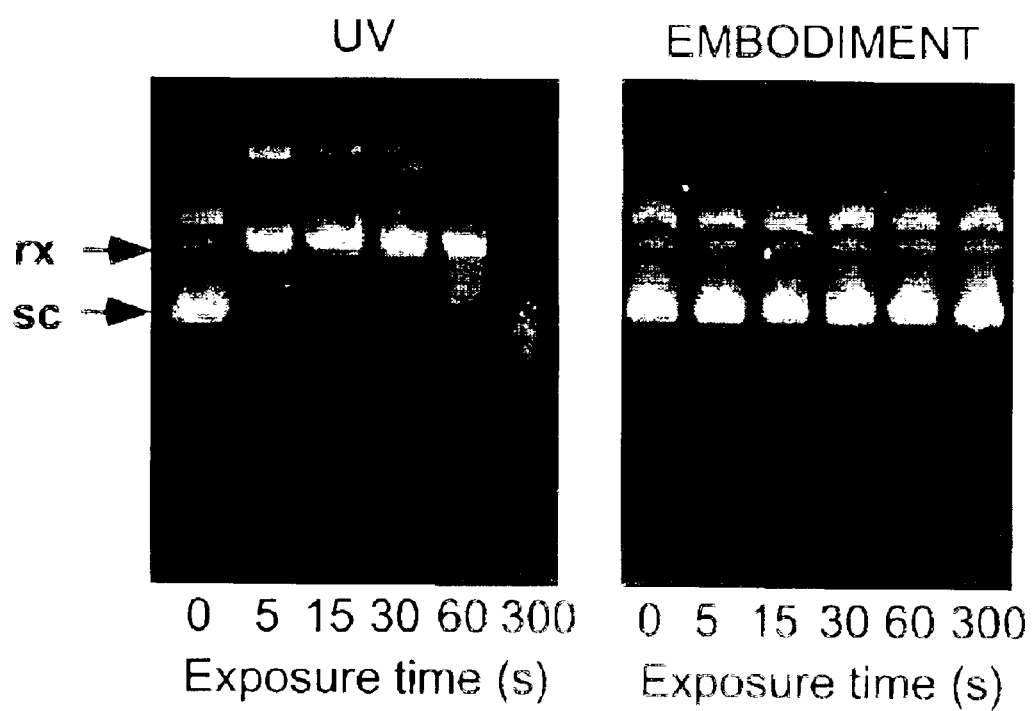
FIG. 22 shows gels comparing DNA degradation using a 312 nm UV transilluminator with DNA degradation using a transilluminator of this invention.

FIG. 22 shows gels comparing DNA degradation using a 312 nm UV transilluminator (right side) with that using a transilluminator of this invention. 100 ng of supercoiled (sc) plasmid pBR322 containing SYBR® Green I was placed on either an embodiment (F40T12/BBY+#668 filter) or a 312 nm UV transilluminator (UV) for various times. The DNA was then digested with T4 endonuclease V which excises T:T dimers. The DNA was then run on a 0.7% agarose gel and photographed. It is clear that as little as a 5 second exposure to UV light is sufficient to convert almost 100% of the plasmid into the relaxed (rx) form, and after 300 seconds, the DNA is completely fragmented. In contrast, a 300 second exposure on the embodiment of this invention resulted in no detectable alteration to the plasmid.

FIG. 23 shows gels comparing DNA stained with ethidium bromide using a standard UV transilluminator (left side) and a transilluminator of this invention (right side).

The power, luminous flux and wavelengths of excitation radiation and emission of the present methods, devices and device components make the present invention well suited for a wide range of applications outside of the area of biotechnology and laboratory instrumentation. Important applications of the present invention include but are not limited to field monitoring devices and methodologies, medical diagnostics and recreational goods.

Figure 24:
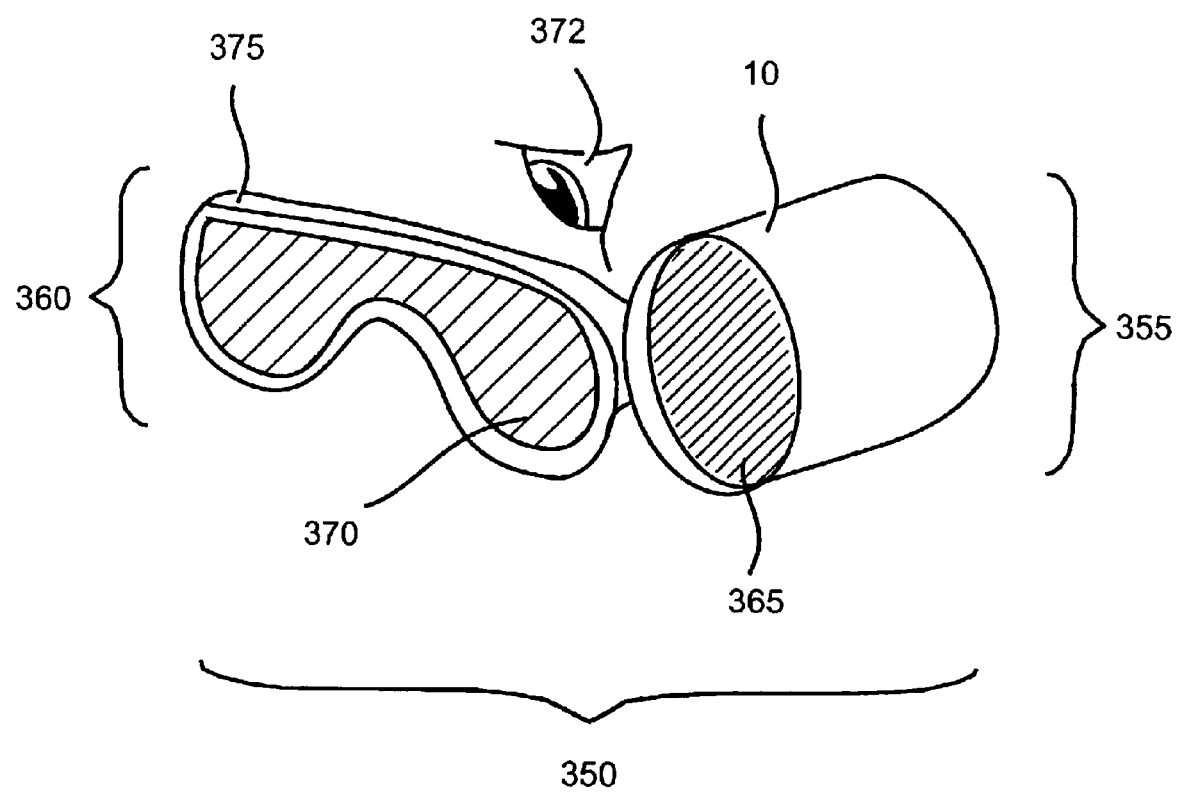
FIG. 24 shows a schematic drawing of a field-monitoring apparatus of the present invention capable of detecting the presence of fluorophors in a sample and generating radiant images and patterns corresponding to emission from fluorophors.

FIG. 24 shows a schematic diagram of a monitoring apparatus of the present invention, particularly well suited for field monitoring applications. The monitoring apparatus shown in FIG. 24 is capable of detecting the presence of fluorophors in a sample and generating radiant images and patterns corresponding to emission from fluorophors. Monitoring apparatus 350 comprises excitation source 355 and filtering element 360. In the exemplary embodiment shown in FIG. 24, excitation source 335 comprises at least one light source 10 and at least one first filter 365. Filtering element 360 comprises at least one second filter 370, which may be held in position in front of a detector 372 by support element 375. In the exemplary embodiment shown in FIG. 24, second filter 370 is integrated into eyeglasses, contact lens (es) or a mask positioned in front of a human eye.

Excitation source 355 generates radiation capable of exciting a fluorophor present in a fluorophor-containing material, preferable light having wavelengths selected over the range of about 380 nm to about 800 nm. In a preferred embodiment, excitation source 355 generates radiation that is substantially free of ultraviolet light. In certain applications, excitation source 355 has a low power consumption, preferably about 9 W or less. Excitation sources having low power consumption are preferred for field monitoring applications in remote locations where power is scarce. Such remote locations include under water, in remote agricultural sites and on other planets. Excitation source 355 may be handheld, stationary or mounted on a moveable support.

First filter 365 substantially transmits light capable of exciting emission in at least one fluorophor present in a fluorophor-containing material and, preferably, is also is capable of substantially preventing transmission of light having a wavelength corresponding to the emission of the fluorophor present in the fluorophor-containing material. Second filter 370 transmits emission generated from fluorophors in a fluorophor-containing material and is capable of substantially preventing transmission of light from excitation source 355. In an exemplary embodiment, first filter 365 is a blue filter capable of transmitting light having wavelengths selected over the range of about 440 nm to about 500 nm and second filter 370 is an amber filter capable of transmitting light having wavelengths selected over the range of about 550 nm to about 620 nm.

The apparatus shown in FIG. 24 operates by epi-illumination of field samples containing fluorophors and subsequent detection of emission. Light capable of exciting fluorophors is generated from excitation source 355, passes through first filter 365 and impinges on a sample containing fluorophors. The excited fluorophors radiate in all directions and a portion of this emission passes through second filter 370 and is detected by detector 372. Importantly, first filter 365 substantially prevents light from light source 10 having a wavelength corresponding to the fluorophor emission spectrum from scattering off or transmitting through the fluorophor-containing sample and being detected by detector 372. Further, second filter 370 substantially prevents transmission of excitation radiation from excitation source 355 and, thereby, functions to separate fluorophor emission from scattered or reflected excitation radiation from excitation source 355.

The field monitoring apparatus 350 shown in FIG. 24 may comprise a field monitoring device for detecting trace contaminants in field samples. In a preferred embodiment, field monitoring apparatus 350 is configured to detect the presence of bacterial contaminants distributed on the surface or in the bulk of meat and agricultural samples. In an exemplary embodiment, a meat or agricultural sample is illuminated by excitation radiation passing through first filter 365, which is configured to transmit light in the violet and blue-violet range from about 380 nm to about 440 nm. Emission from fecal and ingest a contamination in the meat or agricultural sample is generated and passes through second filter 370, which is configured to pass red and purple light from about 640 nm to about 780. The light passing through second filter 370 is detected by a detector, which generates an image or pattern of emission indicating the presence and extent of bacterial contamination. The present invention may also be configured to detect the presence and extent of fungal contaminants.

In another preferred embodiment, the field monitoring apparatus shown in FIG. 24 may be configured to detect trace contaminants in environmental samples. A large number of important environmental pollutants are effectively excited by visible light including but not limited to oil, petrochemicals, pesticides and halogenated organic compounds. Accordingly, the methods and devices of the present invention provide important diagnostics for identifying trace pollutants.

In another preferred embodiment, the present invention provides methods of monitoring genetically modified crops and methods of distinguishing genetically modified crops from non-genetically modified crops. Genes encoding fluorescent and phosphorescent proteins, such as green fluorescent proteins, are easily engineered into many species of crops. Indeed, genes may be engineered into crops in a manner providing probes that express fluorescent and phosphorescent proteins under various internal or external conditions, such as low water or phosphate levels. Accordingly, the present invention provides methods for inspecting and managing genetically modified crops. The present invention is ideally suited for detection of fluorescent proteins, particularly green fluorescent proteins, in genetically modified crops because it is capable of generating measurable fluorescence without the use of ultraviolet light which harms plants. Further, the low power consumption requirements of the excitation sources of the present invention allows for battery-powered units that are easily operated in the field environment and other remote locations.

In another preferred embodiment, the field monitoring apparatus 350 of the present invention is configured to detect fluorophors in an underwater environment and generate radiant images and patterns corresponding to emission from fluorophors. In an exemplary embodiment comprising an underwater photoluminescent imaging system, excitation source 355 is capable of generating excitation radiation in an underwater environment and second filter 375 is integrated into a diving mask. In a preferred embodiment, first filter 365 is a blue filter and second filter 370 is amber. Excitation source 355 may be hand held, mounted on a helmet or may be integrated into a ship or underwater vessel. As is known to one of skill in the art, underwater systems are made substantially water tight. The underwater photoluminescent imaging system of the present invention may be used for viewing fluorescent or phosphorescent sea-life including fish, crustaceans, corals, anemones and genetically modified organisms which express a fluorescent or phosphorescent protein. Alternatively, the under water photoluminescent imaging system of the present invention may be used with a tracer liquid containing fluorophors to provide a method of locating leaks and defects in underwater structures, such as a pipeline or the hull of a ship.

The present invention includes methods and devices for detecting the presence of trace compounds and organisms important for medical diagnosis and forensic applications. In an exemplary embodiment, the present invention comprises an instrument for medical testing or forensic analysis. In this embodiment, a medical or forensic sample is illuminated by excitation radiation generated by an excitation source in optical communication with a first filter. In a preferred embodiment, the first filter is configured such that the excitation radiation impinging on the medical or forensic sample is substantially free of ultraviolet light. A portion of the emission from fluorescent or phosphorescent materials in the sample passes through a second filter, which is configured to substantially prevent transmission of the excitation radiation, and is detected by a suitable detector. Therefore, the second filter provides a means of separating light emitted from the fluorophors from reflected and scattered excitation radiation. In an exemplary embodiment, the methods and devices for detecting the presence of trace compounds and organisms in medical and forensic samples comprise portable diagnostic kits which may be used in a physician's office, at a patient's home or at the scene of a forensic analysis.

In a preferred embodiment, the present invention provides a method of selective detection of a pre-selected fluorophor-containing material in medical or forensic samples with minimized interferences from other fluorophors present in the sample. In this embodiment, the transmission properties of the first and second filters are selected such that only light emitted from a selected fluorophor is detected. For example, the transmission characteristics of the first filter may be selected such that only excitation radiation having a wavelength corresponding to the absorption spectrum of a pre-selected fluorophor impinges on the sample. In a preferred embodiment, the fluorophor of interest is excited and undergoes radiative emission, while other fluorophors present in the sample do not substantially absorb the excitation radiation. Alternatively, the transmission characteristics of the second filter may be selected such that emission from a pre-selected fluorophor is transmitted and subsequently detected, while emission from other fluorophors is substantially prevented from transmitting and is not detected. Accordingly, the present invention provides methods and devices for selectively detecting the presence of a pre-selected fluorophor with minimized interference from other light-emitting species in a sample. Further, the present invention may be configured to simultaneously and individually monitor selected fluorophors in a sample containing several light-emitting species with minimized interference.

The methods and devices of medical and forensic analysis of the present invention may be used on a variety of samples including but not limited to blood samples, tissue samples, bacterial cultures and samples containing bodily fluids. Particularly, the present invention may be use to detect naturally fluorescent or phosphorescent compounds in medical or forensic samples. Alternatively, the present invention may be used to detect fluorescently-labeled compounds in chemically modified medical or forensic samples, such as samples chemically modified by immunoassay techniques. Examples of fluorescent materials in medical or forensic samples that are detectable by the methods and devices of the present invention include but are not limited to semen, head-lice and *Staphylococcus aureus* bacteria.

The present invention includes methods and devices for authenticating materials having at least one fluorophor incorporated therein. Preferred embodiments include methods of authenticating legal documents, bank notes, tickets and official documents. In these embodiments, the methods and devices of the present invention are used to excite a fluorophor incorporated into a selected material and observe the resulting radiant image or pattern. Importantly, the methods and devices of the present invention provide a nondestructive means of authenticating materials because they do not employ damaging ultraviolet light.

The methods and devices of the present invention may also be used to generate and view patterns of fluorophors too small to be resolved by the human eye. In a preferred embodiment, the present invention comprises a method of visualizing small-scale structures such as biological cells. In one embodiment, fluorophors are incorporated into cells as probes, tags or markers and are imaged using the present methods and devices of generating patterns of emission from fluorophor-containing materials. Accordingly, the present invention includes methods, devices and device components for fluorescence microscopy that avoid the use of halogen and mercury vapor lamp light sources having high powers (e.g. powers greater than 50 W). In an exemplary embodiment comprising a device for imaging fluorescent patterns less than about 100 micrometer, a blue light emitting diode, excitation filter and emission filter was incorporated into a conventional stereo microscope with a magnification setting of 45×. The exemplary device provided sensitive detection of fluorescein down to about a concentration of 1 micromoles per liter.

The methods and devices of the present invention may also be used for generating patterns corresponding to fluorophors in microfluidic and micro-array instrumentation. Typically, microfluidic and micro-array devices have millimeter or submillimeter sized channels and detection regions. The ability of the present invention to generate and view patterns of emission from fluorophors confined to and distributed across very small areas makes the present invention ideally suited for microfluidic and micro-array applications. Further, the low power consumption, low heat output and small size of the light sources of the present invention also make the present methods, devices and device components highly compatible to such applications.

The present methods and devices for generating emission from fluorophors without the use of ultraviolet radiation make the present invention well suited for a variety of recreational applications.

Figure 25:
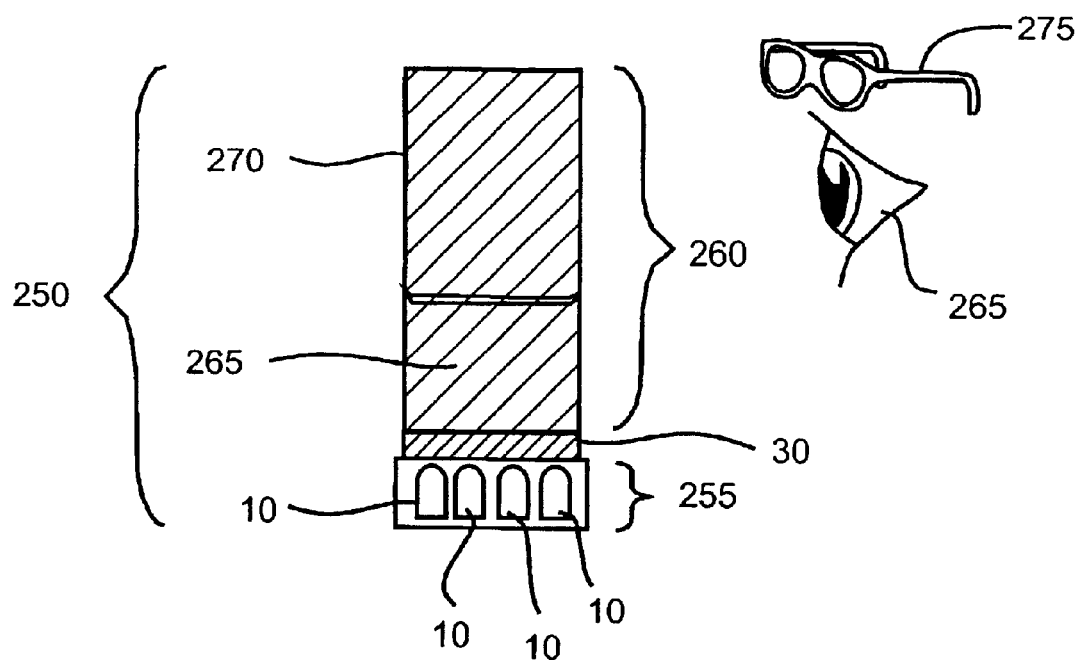
FIG. 25 shows a schematic drawing of a vessel of the present invention.

FIG. 25 shows a schematic diagram of vessel of the present invention capable of exciting a fluorophor-containing material and generating radiant images and patterns corresponding to emission from fluorophors. In the exemplary embodiment shown in FIG. 25, vessel 250 comprises base 255 in optical communication with bowl 260. Base 255 houses at least one light source 10 configured to produce excitation radiation, a portion of which propagates through excitation filter 30 into bowl 260. Fluorophor-containing material 265 is contained in bowl 260, which is configured to ensure that fluorophor-containing material 265 is in optical communication with light sources 10.

In an exemplary embodiment, vessel 250 is a drinking glass and bowl 260 contains a liquid having fluorophors dispersed therein. This embodiment of the present invention provides a means of generating radiant emission in a fluorescent beverage for recreational purposes. Alternatively, this embodiment may comprise methods and devices for detecting trace compounds, such as pharmaceuticals or contaminants in beverages or food. In the exemplary embodiment shown in FIG. 25, light sources 10 generate excitation radiation, preferably radiation substantially free of ultraviolet light, which is directed through excitation filter 30 and excites fluorophors dispersed in the liquid contained in bowl 260. In a preferred embodiment, excitation filter 30 efficiently transmits light capable of exciting the fluorophors dispersed in the liquid present in bowl 260 and substantially prevents transmittance of light having a wavelength corresponding to the emission of the fluorophors. Fluorescence generated by the fluorophors passes through bowl 260 and is detected by light detector 265, preferably the human eye. In an exemplary embodiment, the walls of bowl 260 comprise emission filter 270, which is capable of transmitting fluorescence from the fluorophors in the liquid and capable of substantially transmitting excitation radiation from light source(s) 10. In an alternative embodiment, emission filter is integrated into eyeglasses or contact lens 275 that are placed in front of detector 265. Accordingly, the present invention comprises vessels capable generating one or more patterns of radiant emission by a fluorophor-containing sample.

The present invention also includes embodiments wherein vessel 250 is a dish or food display cabinet. In these embodiments, fluorophors are dispersed in a material contained in or supported by the dish or display cabinet. In an exemplary embodiment, the present invention provides means of detecting the presence of contaminants in food contained in a dish or display cabinet, particularly bacterial or fungal contaminants. Alternatively, the present invention may provide a means of generating fluorescence or phosphorescence from foods for recreation purposes, such as enhancing the visual appeal of food on display or for sale.

Fluorophors useable in this aspect of the invention are described in Table 3 and include naturally fluorescent foods and beverages and genetically modified foods and beverages. In addition, the present invention may be used to generate emission from generically modified foods, which express a fluorescent or phosphorescent protein, such as green fluorescent protein.

TABLE 3

Fluorescent properties of various foodstuffs

| FOOD | FLUORESCENT | COLOR OF FLUORESCENCE |
| --- | --- | --- |
| canola oil | Y | yellow |
| apple juice | Y | yellow |
| thyme (dried) | N | — |
| sage (dried) | N | — |
| turmeric (dried) | Y | yellow |
| cayenne (dried) | Y | yellow |
| ginger (dried) | Y | bright yellow |
| tarragon (dried) | Y | orange |
| white pepper | Y | yellow |
| riced cooked in turmeric | Y | yellow |
| green chili (fresh) | Y | red |
| white wine | Y | yellow |
| syrup (diluted) | Y | yellow |
| honey (diluted) | Y | yellow |
| soy sauce (diluted) | Y | yellow |
| peanut butter | Y | yellow |
| black pepper | Y | orange |
| FD&C red 40 | N | — |
| FD&C yellow 5 | N | — |
| FD&C blue 1 | N | — |
| cherries (preserved) | Y | bright orange |
| white chocolate | Y | bright yellow |
| Danish pastries | Y | yellow |

Figure 26:
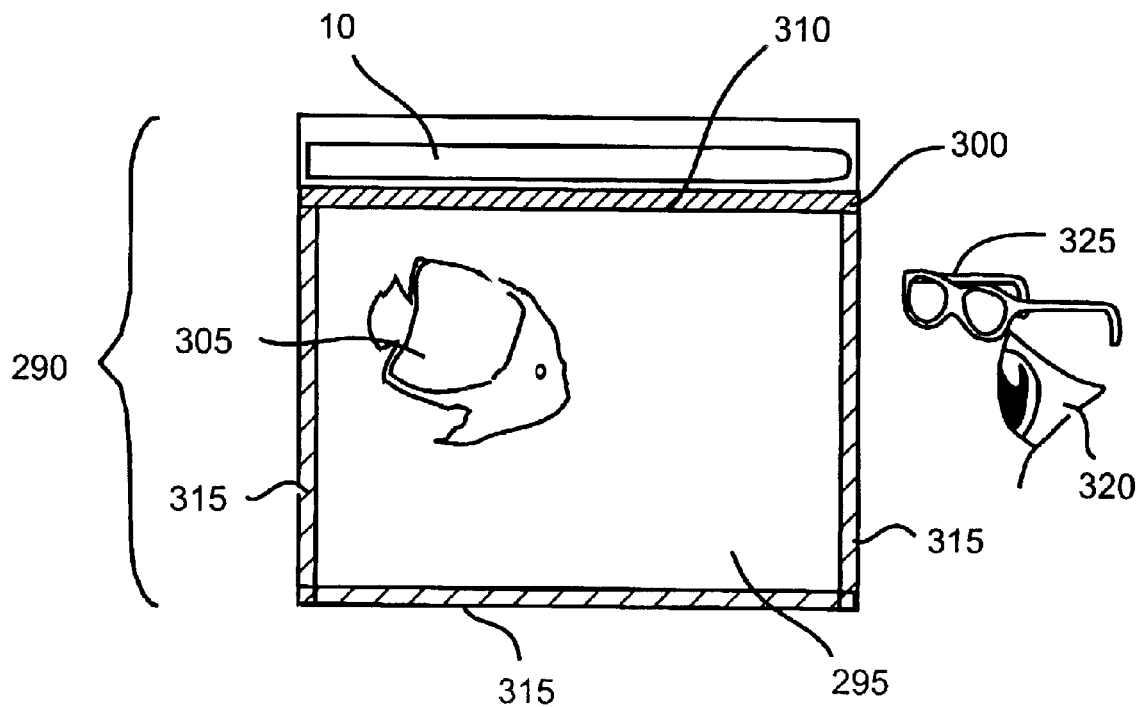
FIG. 26 shows a schematic drawing of a cross-section of a photoluminescent aquarium of the present invention.

FIG. 26 shows a schematic diagram of a cross-section of a photoluminescent aquarium of the present invention capable of generating radiant images and patterns corresponding to emission from fluorophors. In the exemplary embodiment shown in FIG. 26, aquarium 290 comprises at least one light source 10 in optical communication with tank 295 containing materials, organisms, or both, containing fluorophors. In the exemplary embodiment shown in FIG. 26, a fluorescent fish 305 is present in tank 295. Light source 10 generates excitation radiation, preferably radiation substantially free of ultraviolet light and having a wavelength selected from the range of about 380 nm to about 800 nm. Use of excitation radiation substantially free of ultraviolet light is beneficial because avoids damage to organisms and materials in tank 290 and reduces the extent of scattered ultraviolet light to the surroundings. As ultraviolet light is a known mutagen, use of excitation radiation substantially free of ultraviolet light is particularly important for the use of the present invention with organisms, such as intrinsically fluorescent fish, crustaceans, and corals.

First filter 300 is positioned between light source 10 and a first side 310 of tank 295. In a preferred embodiment, first filter 300 efficiently transmits light capable of exciting the fluorophors in tank 295 and substantially prevents transmission of light having a wavelength corresponding to the emission of the fluorophors in tank 295. In an exemplary embodiment, second filter 315 is positioned in optical communication with at least one of the sides of tank 255 other than first side 310. Second filter efficiently transmits emission from the fluorophors to detector 320, preferably the human eye. In a preferred embodiment, second filter substantially prevents transmission of excitation light from light source 10 to detector 320. In an alternative embodiment, second filter is integrated into eyeglasses or contact lenses 325 that are placed in front of detector 320.

In the exemplary embodiment shown in FIG. 26, tank 295 is a rectangular prism, first filter 300 is positioned in optical communication with first side 310 and second filters 315 are positioned in optical communication with the remaining 5 sides of the rectangular prism. As will be evident to anyone skilled in the art, the present invention includes tanks 295 having a variety of other shapes including substantially spherical, cubic, cylindrical and conical shapes. The present invention may be used with any organism or material which generates emission upon absorption of excitation radiation including but not limited to fish, crustaceans, corals, anemones, materials coated with a fluorescent or phosphorescent coating, and genetically modified organisms that express at least one fluorescent or phosphorescent protein, such as green fluorescent proteins.

Figure 27:
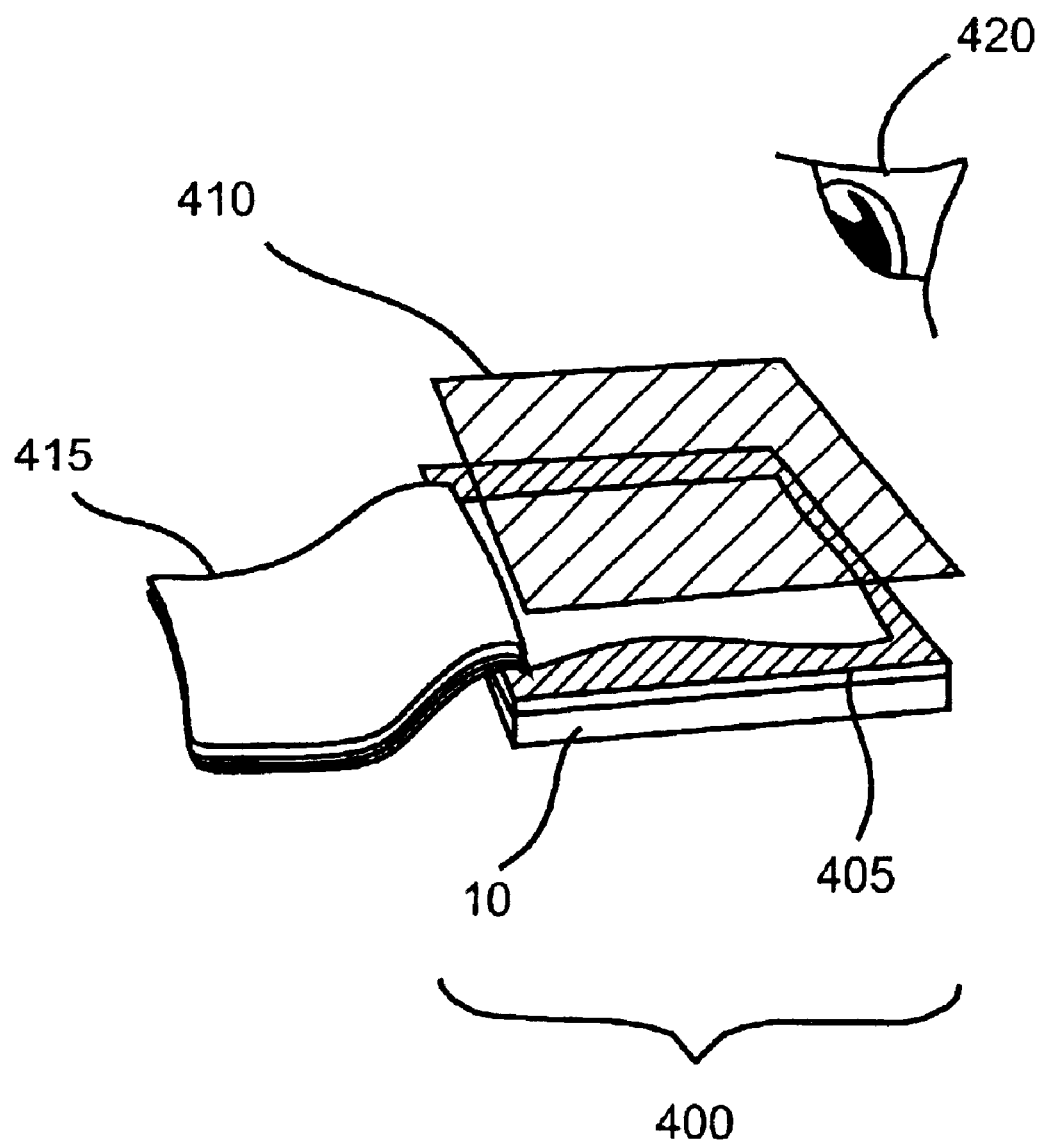
FIG. 27 shows a schematic diagram of a photoluminescent book reader of the present invention capable of generating radiant images corresponding to images printed with fluorescent or phosphorescent ink.

FIG. 27 shows a schematic diagram of a photoluminescent book reader of the present invention capable of generating and viewing radiant images corresponding to images printed with fluorescent or phosphorescent ink. The exemplary photoluminescent book reader 400 shown in FIG. 27, comprises light source 10, first filter 405 and second filter 410. Pages of photoluminescent book 415 having images printed thereon with fluorescent or phosphorescent ink are placed between first filter 405 and second filter 410 and are held in optical communication with light source 10. In the exemplary embodiment shown in FIG. 27, first filter 405 acts as a support for the pages of photoluminescent book 415. Light generated by light source 10 passes through first filter 405 and excites fluorophors in the fluorescent or phosphorescent ink of photoluminescent book 415. A portion of the resulting emission passes through second filter 410 and is detected by human eye 420. The optical properties of the first and second filter are selected according to the method of the present invention to generate patterns of radiant emission without the use of ultraviolet radiation that would damage photoluminescent book 415 and potentially harm the reader. Accordingly, the present invention comprises methods of generating patterns of radiant emission corresponding to the images print in photoluminescent book 415. This aspect of the present invention is beneficial as the images of the photoluminescent book are clearly visible to the reader while the surroundings are dark, which may be of benefit to others in the environment.

Figure 28:
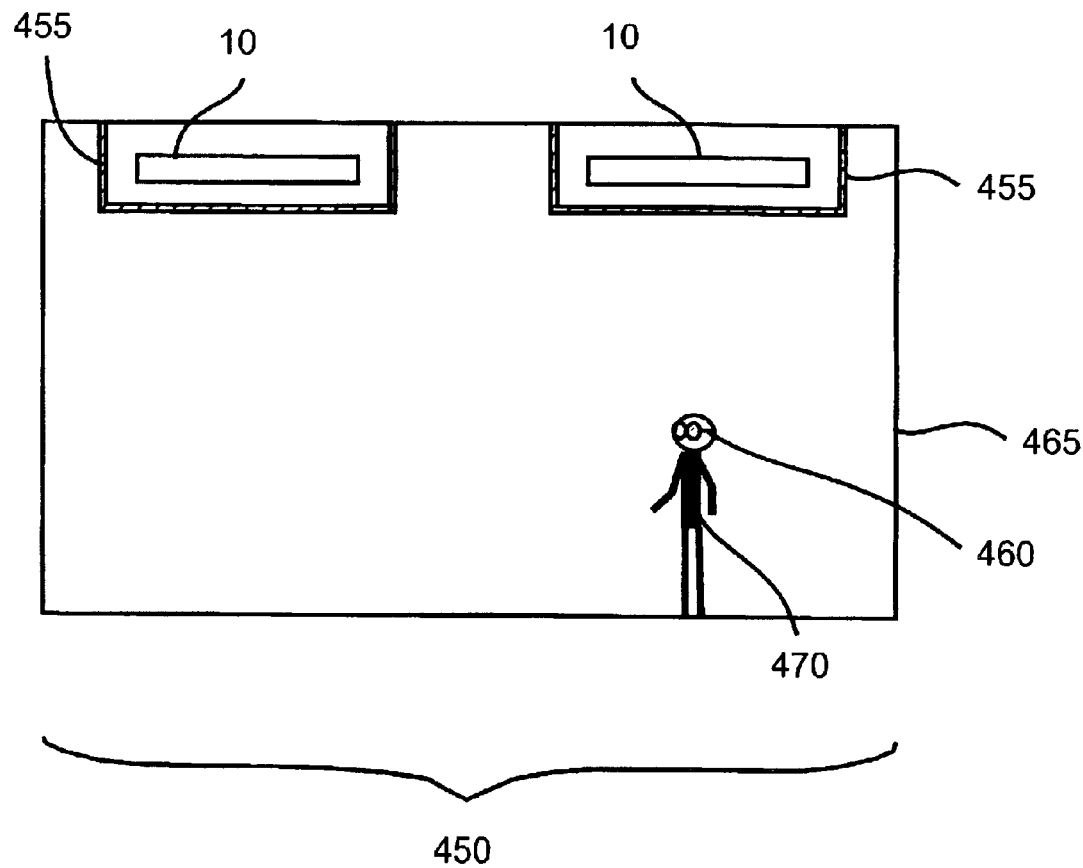
FIG. 28 shows a schematic diagram of a room installation for viewing radiant images and patterns generated from fluorophor-containing materials.

In another aspect of the present invention, the present methods and devices are configured to provide room installations for generating and viewing radiant images and patterns generated from fluorophors. FIG. 28 shows a schematic diagram of room installation 450 comprising at least one light source 10 and first filter 455, each integrated into room 465. Light from light source 10, passes through first filter and excites fluorophors present in room 465. A portion of the resulting emission passes through second filter 460 and is detected by the eye of viewer 470. As shown in FIG. 28, light source 10 and first filter 455 may be configured to be an integral part of room 465 and second filter 460 may be integrated into eyeglasses, contact lens or a mask. Alternatively, light source 10 and first filter may comprise a hand-held or portable unit.

The transmission properties of the first and second filters are selected to generate radiant images and patterns from fluorophors 465 without the exposure of ultraviolet light to room 465 and viewer 470. In an exemplary embodiment, first filter 455 is a blue filter capable of transmitting light having wavelengths selected over the range of about 440 nm to about 500 nm and second filter 460 is an amber filter capable of transmitting light having wavelengths selected over the range of about 550 nm to about 800 nm. In a preferred embodiment, light source 10 and first filter 455 are configured to substantially prevent exposure of ultraviolet light to room 465 and second filter 460 is configured to substantially prevent transmission of light generated from light source 10.

The room installation of the present invention may be used in a wide variety of recreational applications. In one embodiment, room installation 450 is used in a game wherein room 465 is dark and viewer 470 plays with a fluorescent ball. In another embodiment, viewer 470 views a fluorescent art exhibit. In another embodiment, viewer plays a game involving water-pistols filled with fluorescent solutions. In another embodiment, viewer 470 interacts with a naturally fluorescent or phosphorescent organism or a genetically modified organism that expresses a fluorescent or phosphorescent protein. In another, embodiment, viewer 470 consumes photoluminescent beverages or food in a nightclub or theme restaurant.

The room installation of the present invention may be used in a wide variety of non-recreational applications. In one embodiment, viewer 470 examines an organism that is genetically modified to express a fluorescent or phosphorescent protein, such as a crop expressing green fluorescent proteins or a patient undergoing gene therapy treatment. In another embodiment, viewer 470 examines a machines or devices for leaks using a liquid having fluorophors dispersed therein. In another embodiment, viewer 470 performs surgery using photoluminescent surgical devices.

As will be appreciated by those of skill in the art, the second filter shown in any of the above-described embodiments may be provided in the form of lenses for glasses or as attachments to mechanical light detectors rather than as a filter sheet or plate as shown. Further the devices can be configured with interchangeable filters or side-by-side filters to allow different fluorophors to be detected with maximum sensitivity. Lamps may be constructed to provide wavelengths optimized for each system, all as may be readily understood by those of skill in the art following the teachings provided herein.

EXAMPLES

Example 1

Sensitivity

The sensitivity of an optimized device of this invention was measured by detection of known quantities of DNA on gels stained with SYBR® Green I and ethidium bromide, both by eye and by photography. What is seen by the eye and what is recorded on photographic film are not necessarily one and the same, especially when using black-and-white photography. For example, photographic film is able to accumulate an image over many seconds and, after processing, the image can be quantitated. On the other hand, the interpretative skill of the human eye when directly viewing an image is unparalleled. Though scientists use photographs of DNA gels for their laboratory records and for detailed analysis such as calculation of the sizes of DNA fragments, much of the analysis of a DNA band pattern on a gel is achieved using the naked eye. Furthermore, the excision of gel slices containing DNA is always done by eye. Therefore, it is important that the sensitivity of any apparatus for visualization of DNA in gels be documented and optimized for human eye and photographic detection methods separately.

The light-box used was an Apollo 100 obtained from OfficeMax, Denver, Colo. It came equipped with an F15T8DRWG fluorescent tube. This box was convenient for testing 45.7 cm (18 in.) fluorescent tubes such as the Osram F15T8D and Osram F15T8BLK. Other lamps were accommodated in makeshift housings.

Fluorescent tubes were obtained from Environmental Lighting, Denver, Colo. (Osram F15T8D, Osram F15T8BLK, Phillips F40B and Sylvania CF9DS/blue lamps), U.S. Aquarium, Denver, Colo. (Panasonic FPL28EB lamps) and Custom Sea Life Carlsbad, Calif. (No. 05301).

The gelatin filters used were obtained from Mike's Camera, Boulder, Colo., or from Wasatch Photographic, Denver, Colo., and included Kodak Wratten gelatin filters #12 (yellow), #21 (amber), #98 (blue) and #47 (blue) and Lee gelatin filters #15 (amber) and #21 (amber).

The acrylic filters used were obtained from either SS Plastics, Englewood, Colo., Fantastic Plastic, Englewood, Colo., or Colorado Plastic, Boulder, Colo., and included Acrylite#408-5GP (amber), Acrylite#668-0GP (blue), RAM #UM 2119 (amber), Dupont Lucite L #AM2422 (amber) and Dupont Lucite L #AM2424 (blue). In addition, amber filter Perspex® #300 was obtained from Amari Plastics, Bristol, U.K. All American acrylic filters were used in a 0.32 cm (⅛ in.) inch thick sheets except the 668-0GP blue which was used in both 0.32 cm (⅛ in.) and 0.635 cm (¼ in.) thicknesses. The British materials were 3 and 6 mm. Emission filters from Optical Polymer Laboratory, Pawtucket, R.I. were also employed (No. 1152636).

The fluorescent dyes ethidium bromide, SYBR® Green I and SYBR® Gold were obtained from Molecular Probes Inc., Eugene, Oreg. All other chemicals were obtained from Boehringer Mannheim Corporation, Ind., Ind. or Sigma Corporation, St. Louis, Mo.

Three samples of λ DNA (1 µg, 0.1 µg and 0.01 µg) cut with the restriction enzyme EcoRI were electrophoresed in duplicate on a 0.7% agarose gel in 40 mmol/L tris acetate buffer (TAE), pH 7.8; 1 mmol/L ethylene diamine tetraacetic acid (EDTA) at 85 V for 90 minutes. The gel was then cut in half. One half of the gel was stained in a 1:10,000 dilution of SYBR® Green I in TAE for 30 minutes at room temperature, and the other half was stained in 0.5 µg/mL solution of ethidium bromide in TAE under the same conditions. The gels were stored at 4° C.

For reference purposes, the gels were photographed on a UVP model #C-63 UV transilluminator (302 nm illumination) (Ultraviolet Products, Inc., Upland, Calif.) using Polaroid 667 film. The exposure time was 0.5 seconds and the f-stop was 5.5. A Kodak Wratten #12 filter was placed on top of the gel. The camera was an oscilloscope camera C27 (Tektronix Inc., Portland, Oreg.).

In order to determine the optimal configuration of filters and lamps, a prototype visible light transilluminator was constructed according to the scheme illustrated in FIG. 1 and described above. The gelatin filters were enclosed in clear, transparent acrylic sheets to protect them. All filters were enclosed in cardboard frames to prevent light leakage around the edges. A black-out cloth was also used to eliminate stray light from the lamp.

A variety of lamps and filters were placed in the apparatus and the DNA bands in the gels were visualized and photographed in a dimly lit room. No additional filter was used with the camera.

In order to compare the new transilluminator with the conventional UV model, from the known sizes of the fragments generated by EcoRI digestion of the A DNA, the amount of DNA in each band on the agarose gel was calculated. The amounts ranged from 410 ng to 0.7 ng per band. A complete listing is given in Table 4.

To provide a standard measure of detectability, the stained gel was first placed on a standard 302 nm UV transilluminator. The DNA bands were visible using the naked eye down to the 0.9 ng level when stained with SYBR® Green I, and 1.4 ng when stained with ethidium bromide (Table 5). In a photograph, the sensitivity was marginally lower: 1.4 ng for SYBR® Green I and 4.4 ng for ethidium bromide. The slightly greater visibility of the SYBR® Green-stained DNA is probably due to a lower background light level from the gel itself. The ability to detect as little as 0.9 ng of DNA serves as a reference point for the sensitivity of the constructed visible light transilluminator.

The gels were then placed on the new transilluminator and various combinations of blue filters underneath the gel and amber filters above the gel were tried together with different lamps. Both naked-eye and photographic film results are given in Tables 6 and 7.

Of the blue filters, #2424 transmits excessive amounts of red light and its use was not pursued any further. The #98 transmits blue light of significantly shorter wavelengths than either #668-0GP or #47, both of which appear to have very similar transmission characteristics. The shorter wavelength transmission characteristics of #98 mean that it can be used with the yellow emission filers (e.g., #12), whereas #668-0GP and #47 are optimal with the orange emission filters.

With either #668-0GP or #47 as excitation filter, it was found in general that the use of a single orange filter on the emission side was insufficient, either because too much background light was transmitted to allow detection of the fluorescent DNA, or because the filter possessed intrinsic fluorescence which obscured the DNA fluorescence. This latter problem was particularly noticeable with filters #408 and #2422.

The filter fluorescence could be overcome by using two emission filters in-line. Thus, by placing a #2119 or Lee #21 before a #408 or #2422 relative to the lamp, it was possible to significantly reduce the fluorescence of the second emission filter.

Filter Perspex® #300 did not possess any intrinsic fluorescence and, in combination with #668-0GP as the excitation filter, yielded the best overall results.

The photography involved significantly different exposure times: typically, 0.5 seconds for UV, 5 seconds for the F40B, and 15 seconds for the F15T8D. Using the F15T8D, the detectability of SYBR® Green-stained DNA in photographs was approximately the same using either a five second or a 15 second exposure time. However, using a five second exposure, the ethidium bromide-stained DNA was essentially undetectable in photographs.

A useful arrangement involves excitation filter#668-0GP and emission filter#300 (Table 8). Either lamp F15T8D or F40B yields similar levels of DNA detectability to the naked eye. For photographic purposes, the F15T8D requires a 15 second exposure to adequately reveal EB-stained DNA whereas the F40B requires five seconds. This difference is unlikely to be of any practical significance. A lamp readily available in a size that fits the light-box is preferred.

The smallest amount of DNA visible to the naked eye using an F15T8D lamp and #668-0GP and #300 filters is 0.7 ng if stained with SYBR® Green I. This is comparable to the detection level of the UV transilluminator (0.9 ng). With ethidium-stained DNA the white light (WL) transilluminator is somewhat less sensitive with a 4.1 ng detection level, compared to the UV transilluminator's ability to detect 1.4 ng.

By photography, the situation is reversed: the detection level of 0.7 ng for SYBR® Green-stained DNA using the WL transilluminator is somewhat better than the UV transilluminator (1.5 ng). With ethidium bromide-stained DNA, both transilluminators are of comparable sensitivity and can detect 4.1 ng of DNA.

TABLE 4

Amounts of DNA present in the gel after electrophoresis.

| Band No. | Size (base pair) | ng of DNA per band | | |
|---|---|---|---|---|
| | | 1 μg load | 0.1 μg load | 0.01 μg load |
| 1 | 21220 | 410 | 41 | 4.1 |
| 2 | 7420 | 140 | 14 | 1.4 |
| 3 + 4[1] | 5800 + 5640 | 220 | 22 | 2.2 |
| 5 | 4880 | 90 | 9 | 0.9 |
| 6 | 3530 | 70 | 7 | 0.7 |

[1]Bands #3 and #4 were not resolved on the gel.

TABLE 5

Detectable levels of DNA using a UV transilluminator

| | Amount of DNA detectable (ng) | |
|---|---|---|
| Method of Detection | SYBR ® Green I | Ethidium bromide |
| Eye | 0.9 | 1.4 |
| Photo[1] | 1.5 | 4.1 |

[1]The exposure time for the photographs was 0.5 second.

TABLE 6

Naked Eye Detection of Fluorescent DNA[1]

| | Blue Filter | | | | | |
|---|---|---|---|---|---|---|
| | 47 | | 98 | | 668-0GP | |
| | WL | BL | WL | BL | WL | BL |
| Amber Filter | SG EB | SG EB | SG EB | SG EB | SG EB | SG EB |
| 12 + 15 | | | | | 0.9 41 | |
| 2119 + 408 | 0.9 9 | 0.9 9 | | | 0.9 22 | 0.9 9 0.7 4.1 |
| 2119 + 2422 | 0.9 9 | 0.7 4.1 | | | 0.9 22 | 0.9 9 0.7 4.1 |
| 21 + 408 | 0.9 22 | 0.7 9 | | | 0.7 9 | 0.7 4.1 |
| 300 | 0.7 9 | 0.7 9 | | | 0.9 22 | 0.7 4.1 0.7 4.1 |

[1]This table documents the minimum amount of DNA (in nanograms) visible on the gel using various filter combinations.
WL, white fluorescent lamp F15T8D;
BL, blue fluorescent lamp F40B;
SG, SYBR ® Green I;
EB, ethidium bromide. Blank entries were not measured.

TABLE 7

Photographic Detection of Fluorescent DNA[1]

| | Blue Filter | | | | | |
|---|---|---|---|---|---|---|
| | 47 | | 98 | | 668-0GP | |
| | WL | BL | WL | BL | WL | BL |
| Amber Filter | SG EB | SG EB | SG EB | SG EB | SG EB | SG EB |
| 12 + 15 | | | | | | |
| 2119 + 408 | | | | | 0.7 9 | |
| 2119 + 2422 | | | | | 0.9 9 | 0.9 4.1 |

TABLE 7-continued

Photographic Detection of Fluorescent DNA[1]

| | Blue Filter | | | | | |
|---|---|---|---|---|---|---|
| | 47 | | 98 | | 668-0GP | |
| | WL | BL | WL | BL | WL | BL |
| Amber Filter | SG EB | SG EB | SG EB | SG EB | SG EB | SG EB |
| 21 + 408 | | | 1.0 9 | | 0.7 9 | 0.9 9 |
| 300 | 1.0 9 | 1.0 9 | | | 0.7 4.1 | 0.7 4.1 |

[1]This table documents the minimum amount of DNA (in nanograms) detectable in photographs of the gel.
WL, white fluorescent lamp F15T8D;
BL, blue fluorescent lamp F40B;
SG, SYBR ® Green I;
EB, ethidium bromide.
The exposure times for the WL and BL photographs were 15 seconds and five seconds, respectively.

TABLE 8

Detectable Levels of DNA Using the Transilluminator[1]

| Method of Detection | Amount of DNA detectable (ng) | |
|---|---|---|
| | SYBR ® Green I stained gel | Ethidium Bromide stained gel |
| Eye | 0.7 (0.9) | 4.1 (1.4) |
| Photo | 0.7 (1.5) | 4.1 (4.1) |

[1]The transilluminator was equipped with an F15T8D lamp and #668-0GP (blue) and #300 (amber) filters. For the photographic detection the exposure time was 15 seconds. The amounts of DNA detectable using a UV transilluminator are in parentheses. (See Table 4.)

The sensitivity of an alternative optimized device of this invention was also determined by detection of known quantities of DNA on gels stained with SYBR® Green stain (Molecular Probes, Eugene, Oreg.), SYBR® Gold stain (Molecular Probes, Eugene, Oreg.), GelStar stain (BioWhittaker) and ethidium bromide. Specifically, the detection sensitivities of an alternative exemplary embodiment comprising two blue 28 W fluorescent lamps, a Cryo a #668-0GP excitation filter, and a Perspex® #300 emission filter were determined by eye and by photography using a Polaroid camera, a C3000 digital camera (Olympus) and a Doc-It digital camera (Ultraviolet Products, Upland, Calif.). Experiments evaluating the detection sensitivity of DNA stained with ethidium bromide also employed an additional emission filter comprising a Wratten #21 filter.

DNA molecular weight standard IV (Roche Molecular, Indianapolis, Ind.) was used to prepare the DNA samples analyzed. A 2-fold dilution series of the DNA was prepared in 40 mM Tris-acetate, 1 mM EDTA, 5 mM mercaptoethanol, pH 8.4. The DNA samples were loaded onto 1% agarose gels (BioWhittaker Molecular, Rockland, Me.) in 40 mM Tris-acetate, 1 mM EDTA, pH 8.4 (TAE buffer). The total amount of DNA loaded onto the gels ranged from 12.5 ng down to 0.39 ng. The gels were run for 50 minutes at 110 V using TAE buffer as the running buffer. The gels were then stained with: (1) a 1:10,000 dilution of SYBR® Green stain in TAE buffer for 30 minutes, (2) a 1:10,000 dilution of SYBR® Gold stain in TAE buffer for 30 minutes, (3) a 1:10,000 dilution of Gelstar stain in TAE buffer for 30 minutes or (4) a 0.1 microgram/mL ethidium bromide solution in TAE buffer for 45 minutes.

Fluorescent images of the DNA samples were generated using the exemplary embodiment and detection sensitivities were obtained by identifying the lowest concentration of stained DNA which generated a detectable level of fluorescence. Camera settings were adjusted to achieve the maximum sensitivity of DNA detection above background. The maximum aperture settings on the cameras and exposure times of 1–10 seconds were employed. The gels were also examined by eye in a darkened room. Table 9 summarizes the detection sensitivities determined for each stain evaluated. For comparison, sensitivities determined using a conventional ultraviolet light transilluminator are also shown in Table 9. As shown in Table 9 the present invention is capable of very sensitive detection of DNA stained with a wide variety of stains and is a substantial improvement over conventional ultraviolet light transilluminators.

ment of the present invention equipped with a CF9DS/blue lamp, a #668-0GP first filter, and a #300 second filter (no additional filter over the camera, f-stop=5.6, exposure time=1 second).

The photographs are shown in FIG. 20. Table 10 shows the amount of DNA in each band.

TABLE 10

The Amount of λ DNA cut with HindIII on the Gel.
The amounts of DNA listed are in ng.

| | Lane # | | | | | | | | | |
|---|---|---|---|---|---|---|---|---|---|---|
| | 1 | 2 | 3 | 4 | 5 | 6 | 7 | 8 | 9 | 10 |
| | | | | | DNA Load | | | | | |
| | 428 | 214 | 107 | 54 | 27 | 13 | 6.7 | 3.3 | 1.7 | 0.85 |
| Band 1 | 204 | 102 | 51 | 26 | 13 | 6.4 | 3.2 | 1.6 | 0.80 | 0.40 |
| Band 2 | 83 | 42 | 21 | 10 | 5.2 | 2.6 | 1.3 | 0.65 | 0.32 | 0.16 |
| Band 3 | 58 | 29 | 14 | 7.2 | 3.6 | 1.8 | 0.90 | 0.45 | 0.22 | 0.11 |
| Band 4 | 38 | 19 | 10 | 4.8 | 2.4 | 1.2 | 0.60 | 0.30 | 0.15 | 0.075 |
| Band 5 | 20 | 10 | 5.1 | 2.6 | 1.3 | 0.64 | 0.32 | 0.16 | 0.080 | 0.040 |
| Band 6 | 18 | 8.9 | 4.5 | 2.2 | 1.1 | 0.56 | 0.27 | 0.13 | 0.070 | 0.035 |

In the photograph taken using the embodiment of this invention, it is possible to visualize band 3 in lane 10. This corresponds to 110 pg of DNA. In the photograph taken using the UV transilluminator it is possible to see band 2 in lane 10. This corresponds to 160 pg of DNA.

By eye, lane 10, band 4 (75 pg) was just at the limit of visibility for both devices.

TABLE 9

| | Amount of DNA Detected (pg) | | | | | |
|---|---|---|---|---|---|---|
| | CCD | | Polaroid | | Eye | |
| Stain | UV | DR | UV | DR | UV | DR |
| SYBR ® Green | 15 | 9 | 44 | 19 | 119 | 60 |
| SYBR ® Gold | 15 | 9 | 34 | 15 | 73 | 35 |
| GelStar | 15 | 9 | 31 | 15 | 120 | 44 |
| EtBr | 89 | 623 | 125 | 500 | 500 | 2560 |

Example 2

Blue Compact Fluorescent Lamps and SYBR® Gold

Various dilutions of a DNA cut with HindIII (Boehringer Mannheim) in 10 mmol/L Tris-Cl, 1 mmol/L EDTA were incubated at 60° C. for three minutes. The samples were placed on ice and sample loading buffer (0.25% bromophenol blue, 0.25% xylene cyanol, 15% Ficoll type 400 in 10 mM Tris-Cl, 1 mmol/L EDTA, pH 7.5) was added to each mix. Various amounts of the DNA samples (from 428 ng to 0.85 ng) were loaded onto a 1% agarose gel 7.6×12.7 cm (3"×5" in.) in 89 nmol/L Tris borate, pH 7.82, and 2 mmol/L EDTA (TBE). The gel was run at 80 V for two hours and then placed in 100 mL of 1:10000 dilution (in TAE) of SYBR® Gold for 30 minutes. The gel was photographed using a Polaroid® camera (Polaroid Corporation, Cambridge, Mass. with Polaroid 667 film on either a Fisher UV 312 nm variable intensity transilluminator (Fischer Scientific, Pittsburgh, Pa., Model No. FBTTV-816), set to maximum intensity in all cases, a Wratten #12 on the camera, f-stop=5.6, exposure time=⅛ second) or an embodi- Example 3

Ethidium Bromide Gel

DNA cut with HindIII (Boehringer Mannheim) in 10 mmol/L Tris-Cl, 1 mM EDTA was mixed with sample loading buffer and various amounts of DNA (from 125 ng to 15.6 ng) were loaded onto a 0.7% agarose gel (3"×5") in TAE. Ethidium bromide was added to both the gel and running buffer to a final concentration of 0.25 µg/mL. The gel was run at 110 V for two hours and then examined by eye and photographed using a Polaroid camera with Polaroid 667 film on either a UV 312 nm transilluminator (Fisher Scientific) set to maximum lamp intensity using a red Tiffen 40.5 mm 23A filter (Tiffen Manufacturing Corp., Hauppauge, N.Y.) on the camera (f-stop=5.6, exposure time=2 seconds) or an embodiment of the present invention as depicted in FIG. 9 equipped with a CF9DS/blue lamp, a #668-0GP first filter, and a Perspex® #300 second filter. A Wratten #21 (Kodak) was used as an additional second filter for photography (f-stop=5.6, exposure time=30 seconds). The gel was also observed and photographed (f-stop=5.6, exposure time=10 seconds) on an embodiment identical to the above except that it contained two CF9DS/blue lamps.

The photographs of the gel are shown in FIG. 23. Table 11 shows the amount of DNA in each band.

TABLE 11

The amount of λ DNA cut with HindIII on the Gel.
The amounts of DNA listed are in ng.

| | Lane # | | | |
|---|---|---|---|---|
| | 1 | 2 | 3 | 4 |
| | | DNA load | | |
| | 125 | 63 | 31 | 16 |
| Band 1 | 60 | 30 | 15 | 7.5 |
| Band 2 | 24 | 12 | 6.1 | 3.0 |
| Band 3 | 17 | 8.5 | 4.2 | 2.1 |
| Band 4 | 11 | 5.6 | 2.8 | 1.4 |
| Band 5 | 6.0 | 3.0 | 1.5 | 0.75 |
| Band 6 | 5.2 | 2.6 | 1.3 | 0.64 |

By eye, using the UV transilluminator, it was possible to see 0.65 ng of DNA. Using the single lamp embodiment it was possible to see 2.4 ng of DNA, and using the twin lamp embodiment it was possible to see 1.2 ng of DNA. Overall, the viewability of the DNA bands in the twin lamp embodiment was better than in the single lamp version in that the eye did not take as long to adjust as it did to the lower light levels emanating from the single lamp version.

In the Polaroid photograph taken using the 312 nm UV transilluminator it is possible to see band 6 in lane 4. This corresponds to 0.65 ng of DNA. In the photograph taken using the single lamp embodiment it is possible to see the same band if the Polaroid film is exposed for 30 seconds. The twin lamp embodiment gave very similar DNA detectability results in the photograph but the exposure time required was only one third as long.

Example 4

Gel Scanning

The SYBR® Gold-stained gel used in Example 2 was placed on an Astra 600S scanner (Umax Technologies, Inc., Fremont, Calif.) linked to a Power CenterPro™ 180 computer (PowerComputing, Round Rock, Tex.) running VistaScan V2.3.7 software (Umax Data Systems, Inc.). The amber filter Perspex® #300 was placed on top of the scanner bed, the gel placed on top of the Perspex and, on top of that, a #668-0GP first filter and a CF9DS/blue lamp. The gel was scanned in color at 600 dpi using "transmissive mode" with VistaScan settings of 97, 9, 34 and 53 for highlight, shadow, brightness and contrast respectively.

FIG. 21 shows the resultant image enhanced using image manipulation software as found in Canvas 5.0 (Deneba Systems, Inc., Miami, Fla.). It is possible to see band I in lane 6. This corresponds to 6.4 ng of DNA.

Example 5

DNA Integrity

Supercoiled plasmid pBR322 was placed on either a transilluminator of this invention or a 312 nm UV transilluminator for various periods of time. The DNA was then digested with T4 endonuclease V which excises T:T dimers and run on a 0.7% agarose gel to allow quantitation of the amount of relaxed plasmid formed.

1 µg of supercoiled pBR322 in 100 µL of 50 mmol/L Tris, pH 7.5, 5 mmol/L EDTA was incubated with 1 µL of a 100-fold dilution of SYBR® Green I (diluted in 50 mmol/L Tris, pH 7.5, 5 mmol/L EDTA) on ice. This mixture was placed directly onto the surface of either an embodiment composed of an F40T12/BBY lamp (Interelectric Inc., Warren, N.J.) and a Cyro #668-0GP filter, or a 312 nm UV transilluminator. A "zero-time" aliquot of 10 µL was removed from the surface before turning on the transilluminator and stored in the dark on ice. Further 10 µL samples were removed at 5, 15, 30, 60 and 300 seconds after the device was turned on.

1 µL of a 20-fold dilution (using 50 mmol/L Tris, pH 7.5, 5 mmol/L EDTA) of T4 endonuclease V (Epicentre, Madison, Wis.) was added to each 10 µL time-point and allowed to react for two hours, 37° C. This enzyme excises T:T dimers. The samples were then run on a 0.7% agarose gel in TAE and the band pattern photographed.

The results are shown in FIG. 22. UV light is shown to be extremely damaging to DNA; after a mere five second exposure the supercoiled DNA is almost completely converted to the relaxed form, and after five minutes almost all the DNA has been converted into a low molecular smear. Using the transilluminator of this invention, however, essentially no DNA damage was detectable over the entire duration of the exposure (five minutes). Specifically, a quantitative analysis of the band intensities shown in FIG. 22 establishes that less than about 8% of the DNA in the sample was damaged over the 5-minute illumination period using the methods of the present invention. In contrast, 100% of the DNA in the sample was damaged in less than 5 seconds using the ultraviolet light transilluminator. The present invention, therefore, comprises improved methods and devices for generating patterns of emission from samples containing fluorophors, which are at least 750 times less damaging to polynucleotide containing samples, oligonucleotide containing samples or both than methods using an ultraviolet light transilluminator. Accordingly, the present invention comprises methods and devices for generating patterns of emission from oligonucleotide samples, polynucleotide samples or both containing fluorophors wherein the oligonucleotide sample, polynucleotide sample or both undergoes no substantial damage for illuminations periods less than about 5 minutes. "Substantial damage" is intended to be interpreted consistent with the meaning of this term by persons or ordinary skill in the art and refers to an amount of damage that is not tolerated for a given application.

The invention maintains the integrity of the DNA samples. This feature of the invention provides for enhanced efficiencies in procedures where the integrity and information content of the DNA samples is important such as gene cloning and sequencing.

Example 6

Polarization

To test the ability of a pair of polarization filters to select for fluorescent light and to remove lamp light, an agarose gel containing various amounts of λ DNA restricted with HindIII and stained with SYBR® Gold stain (the same gel used in Example 2) was viewed using several filter combinations. The light source was a CF9DS/blue lamp. The polarizing filters were from Visual Pursuits, Inc., Vernon Hills, Ill.

TABLE 12

| First filter | Second filter | ng DNA |
|---|---|---|
| none | none | 26 |
| P* | P (parallel) | 83 |
| P | P (orthogonal) | 5.2 |

*P indicates a polarization filter from Visual Pursuits.

For photography using Polaroid 667 film it was found to be necessary to include a Wratten #21 filter to reduce the lamp light to levels at which the fluorescent DNA bands could be captured.

The lamp light was not completely eliminated by the two orthogonal polarizing filters, making the sensitivity of this embodiment relatively poor. The absorption spectrum of two orthogonal polarizing filters together revealed that a significant amount of blue light was transmitted (% $T_{460\,nm}$=0.23%). This indicates that these particular polarizing filters are not polarizing the light in this wavelength range efficiently enough to be of much practical use. Filters which, in combination, have a % T of around 0.02% or less are required. Polarization of fluorescence may be used to distinguish between large and small fluorophor molecules, immobilized or free fluorophor molecules, or oriented/non-oriented molecules.

Example 7

Photoluminescent Imaging with Liquid Crystal Display Light Sources

Light sources of the present invention include materials than are induced to emit light by a wide range of processes including but not limited photoluminescence, chemiluminescence, and electroluminescence. In particular, electroluminescent materials, such as those found in liquid crystal display (LCD) panels, comprise a class of materials that exhibit low power consumption and low luminous fluxes that are desirable for certain applications of the present invention. In the present invention, the term "electroluminescence" refers to the emission of light by a material, such as a phosphor or semiconductor, that is excited by an electromagnetic field. The compatibility of the present invention with electro-luminescent materials was directly evaluated by exciting fluorescent materials with a liquid crystal display panel light source comprising a computer monitoring screen and detecting the resulting fluorescence using the methods and devices of the present invention.

Figure 29:
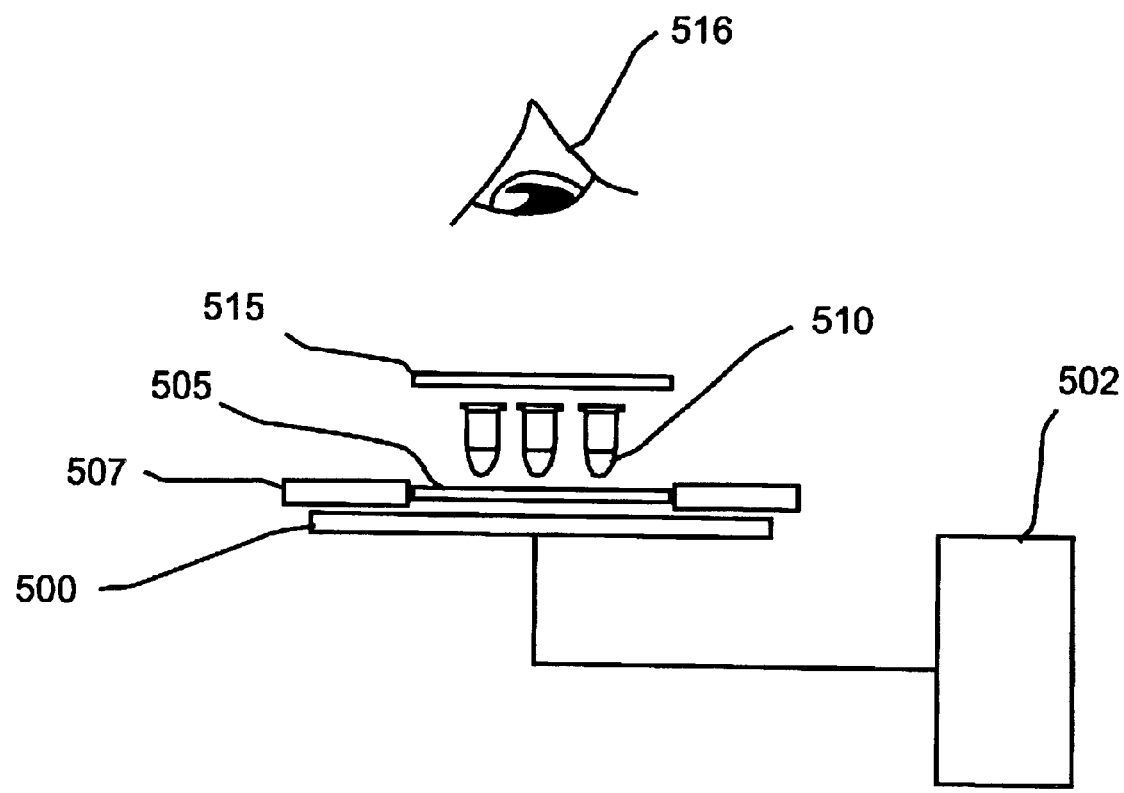
FIG. 29 is a schematic drawing of a photoluminescent imaging system of the present invention having an electroluminescent light source comprising a liquid crystal display panel.

A 15-inch LCD screen of a computer monitor (model # RAD-5 from Korea Data Systems, Garden Grove, Calif.) was used as the light source in a photoluminescent imaging system of the present invention. Specifically, LCD light source 500, excitation filter 505, sample containing fluorophors 510 and emission filter 515 were arranged as shown in FIG. 29. Optionally, the optical arrangement in FIG. 29 may include opaque frame 507 to further minimize detection of light from light source 500. As illustrated in the optical arrangement shown in FIG. 29, the illumination surface of the LCD screen was oriented horizontally and the first excitation filter placed directly on the screen surface. Human eye 516 is also shown in FIG. 29 to illustrate one manner of viewing the radiant images generated.

Viewing emission filter from angles of incidence other than normal incidence is also within the scope of the invention and is preferred in some applications because it reduces background light from the LCD light source. Optionally, the photoluminescent imaging system of the present invention may further comprise computer controller (502) for controlling the emission of the LCD light source. The nominal power consumption of the LCD screen light source was 24 W. In circumstances where the filter was not large enough to cover the entire LCD screen, a black-out cloth was used to cover the extra surface area, thereby, minimizing the generation and subsequent detection of extraneous excitation light. Sample tubes were placed directly on top of the excitation filter and the emission filter was positioned between the samples and the viewer or a camera. The photoluminescent imaging system was operated in a darkroom to minimize interference from scattered room light.

Adjustments to the color of the light emitted by the LCD panel were made by two methods: (1) adjustment of the computer monitor "master controls" that allow variation of the intensities of the red (R), green (G) and blue (B) channels and (2) selection of a color using a software package (OOIBase32 from Ocean Optics, Dunedin, Fla.) that provides a display of a large colored panel (about 295×265 mm) within the monitor window. The color was quantified as an RGB value within the software. The various RGB settings for the screen and software used for the tests are summarized in Table 13.

The term "color setting" refers to a characteristic of a liquid crystal electroluminescent light source classifying the wavelengths of light generated by the light source. When used to describe the optical properties of a liquid crystal display panel, color setting may be defined in terms of a summation of red, green and blue monitor channels. The color settings shown in Table 13 are intended to be examples and are not intended to comprise a complete list of the various color settings achievable using liquid crystal display panel light sources.

TABLE 13

Monitor settings and software settings used to generate the various colors of the LCD screen

| | Monitor Channels | | | Software Channels | | |
|---|---|---|---|---|---|---|
| Screen Color | R | G | B | R | G | B |
| white | 41 | 16 | 14 | 255 | 255 | 255 |
| blue | 0 | 100 | 100 | 0 | 0 | 255 |
| blue-green | 0 | 100 | 100 | 0 | 255 | 255 |
| green | 0 | 100 | 100 | 0 | 255 | 0 |

The fluorescent samples employed in this study were fluorescein maleimide (FL) and tetramethylrhodamine maleimide (TMR). Each fluorophor was dissolved in 40 mM Tris acetate, 1 mM EDTA, pH 8.4 (TAE) and a 2-fold dilution series was made into a set of small plastic tubes. The FL concentrations ranged from 6.0 down to 0.19 micromoles/L. The TMR concentrations ranged from 2.9 down to 0.09 micromoles/L.

Excitation filters used included a 5 mm thick blue acrylic sheet (Cyro 668-0GP) and a blue-green gelatin film (Kodak Wratten #44). Emission filters included a 3 mm thick amber sheet (ICI 300) and an amber gelatin film (Kodak Wratten #22). The 668/300 filter set was used to detect the fluorescein samples and the 44/22 filter set used to detect the tetramethylrhodamine samples.

Patterns of fluorescence generated by the photoluminescent imaging system of the present invention were viewed by eye and also recorded using an Olympus C3000 digital camera. Image analysis was performed in Canvas 8 (Deneba, Miami, Fla.) and/or IGOR 4 (Wavemetrics, Lake Oswego, Oreg.).

Spectra were recorded using a S2000 spectrometer (Ocean Optics, Dunedin, Fla.) equipped with a #2 grating (200–850 nm), 200 micrometer width entrance slit, variable long-pass (200–850 nm) longpass detector filter, UV2 upgrade and L2 detector collection lens. Light was collected through a 600 micrometer optical fiber (UV/VIS) fitted with a collimator lens (UV/VIS). When necessary, the light was attenuated using a fiber optic variable attenuator and then passed to the spectrometer unit through a 200 micrometer optical fiber (UV/VIS).

Figure 30:
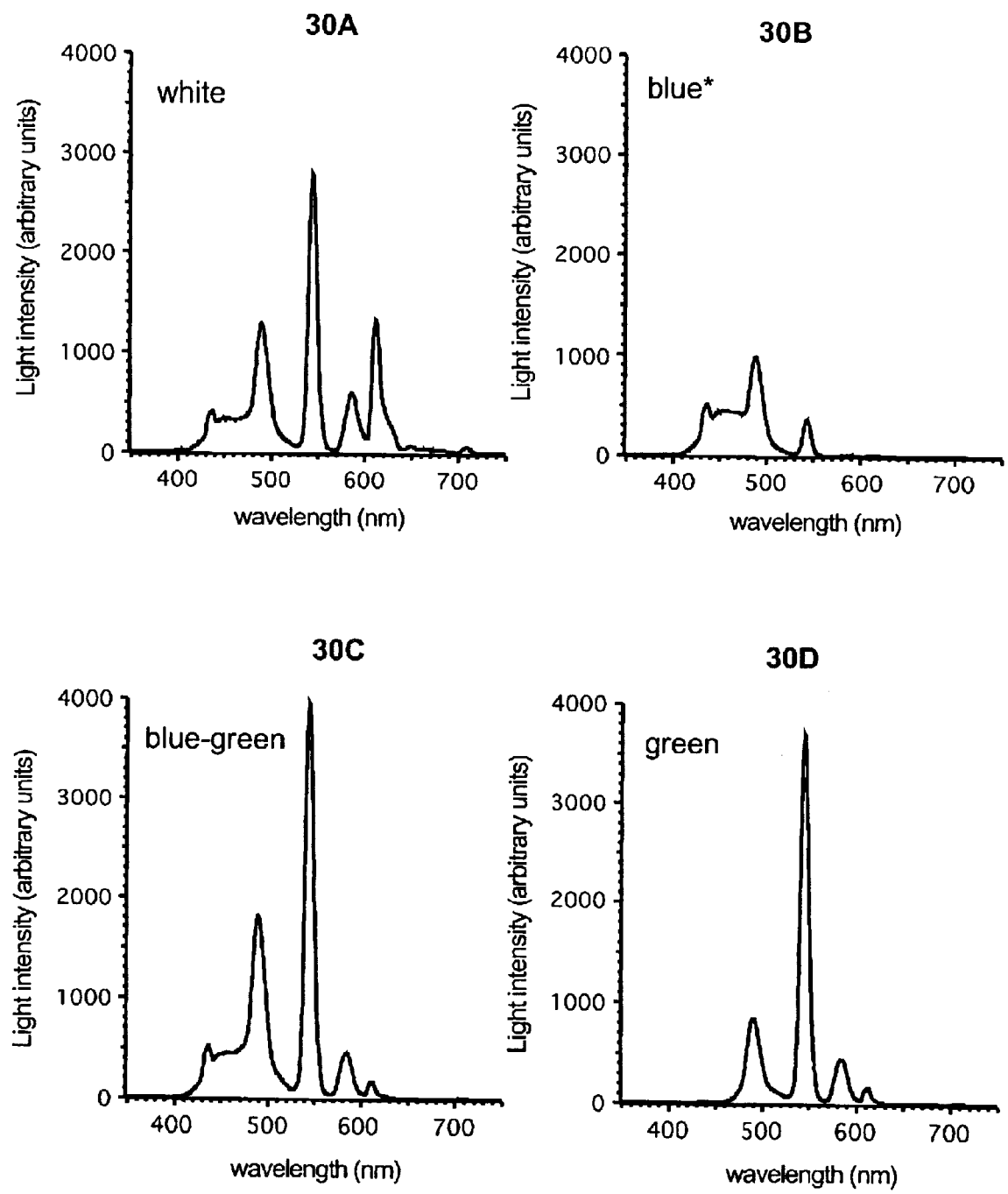
FIGS. 30A–D show spectra of light emitted by a LCD light source for various color settings.

White, blue, blue-green and green LCD panel colors were evaluated as light sources for the methods and devices of the present invention. As shown in Table 13, these colors may be quantified as a combination of monitor and software RGB values. In addition these colors may be quantified as light intensity spectra, as shown in FIG. 30.

Figure 31:
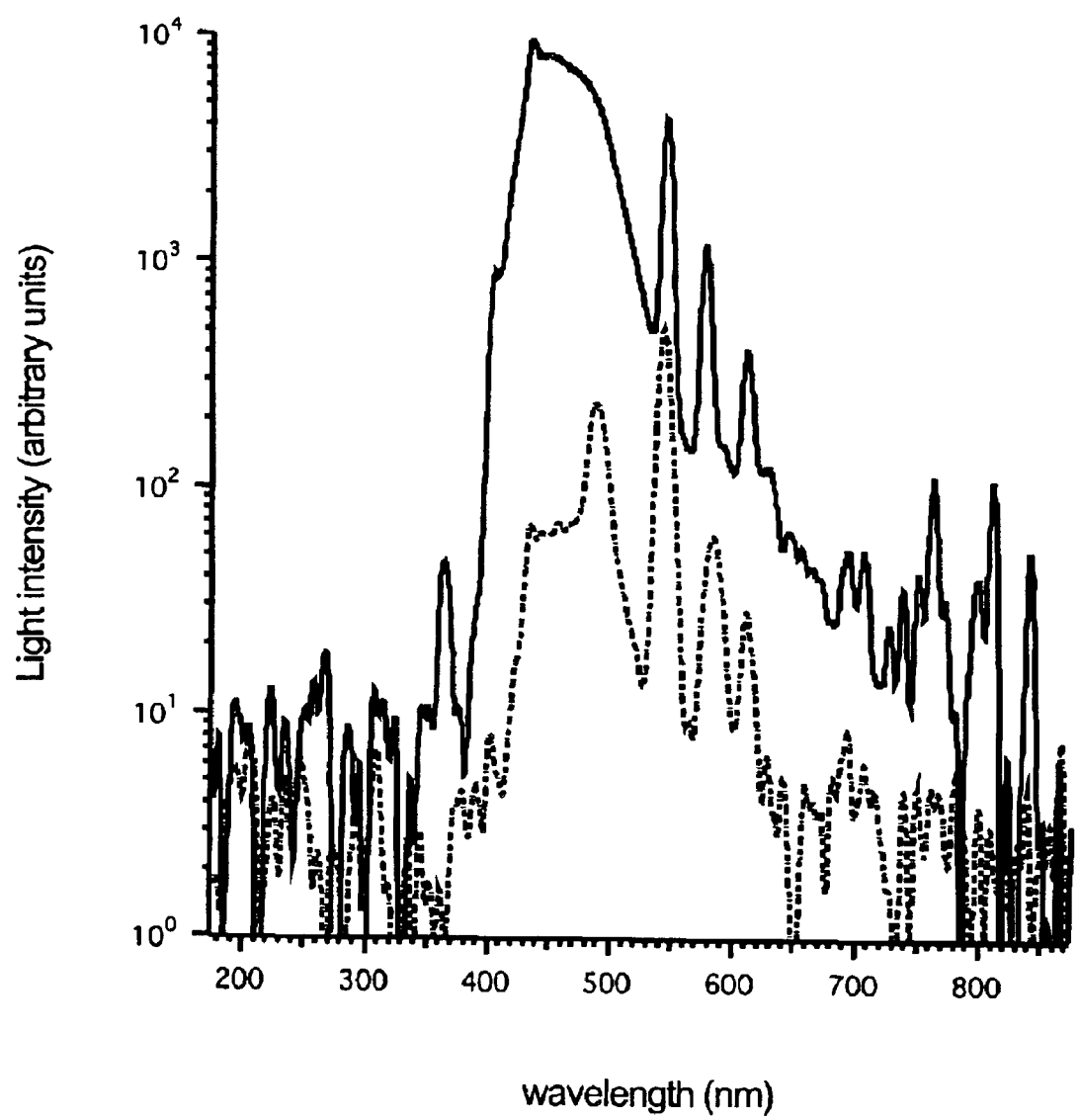
FIG. 31 shows spectra corresponding to the spectral output of a LCD light source having a blue-green color setting (the dotted line) and a 9 W blue fluorescent lamp (solid line).

To evaluate the effectiveness of LCD panels as electroluminescent light sources of the present invention, a comparison was made of the light output by the LCD panel and a 9 W blue fluorescent lamp. The light intensities of both light sources are shown in FIG. 31. As shown in FIG. 31, the fluorescent lamp produced 40 times more light having wavelengths between about 400 nm to about 750 nm than the blue-green LCD panel (monitor settings RGB= 0:100:100) and about 260 times more than the blue LCD panel (monitor settings RGB=0:0:100).

In spite of the relatively low light output from the LCD panel, fluorescence from FL and TMR samples was clearly visible to the naked eye. Sensitivities of the photoluminescent imaging system for TMR and FL using a variety of LCD colors are reported in Tables 14 and 15, respectively. The detection sensitivity using LCD light sources, however, was not as good as the sensitivity obtained with a 9 W blue fluorescent lamp. For example, a sensitivity below 2 nanomoles per liter is routinely observed for FL using a 9 W blue fluorescent lamp. The lower sensitivity observed for embodiments using LCD optical sources most likely arises from the lower luminous fluxes exhibited by these detectors.

TABLE 14

Summary of tetramethylrhodamine (TMR) detection levels

| | Detectable amount of TMR ($\mu$/L) | |
|---|---|---|
| LCD color | Eye | CCD |
| white | 0.73 | 0.36 |
| blue | 0.73 | 0.73 |
| blue-green | 0.36 | 0.09 |
| green | 0.73 | 0.09 |

TABLE 15

Summary of fluorescein (FL) detection levels

| | Detectable amount of FL ($\mu$/L) | |
|---|---|---|
| LCD color | Eye | CCD |
| white | 0.19 | 0.19 |
| blue | 0.19 | 0.19 |
| blue-green | 0.36 | nd |
| green | 0.75 | nd |

For embodiments employing LCD light sources, detection of background light from the excitation source was substantially reduced by changing the angle of the viewer to about 45° or more "off-axis." In the present invention "off-axis" refers to a deviation of the viewing or detection angle from normal incidence to the LCD surface. Thus, "off axis" viewing geometries were observed to substantially enhance the sensitivities of embodiments using LCD light sources. The directional propagation of the LCD light sources is beneficial in a fluorescence-viewing device because background light levels may be reduced substantially using "off axis" detection, which results in more sensitive detection.

The distribution of light across the illumination surface of the LCD panel was substantially uniform. In contrast, some fluorescent lamps exhibited non-uniform light distribution, which necessitates use of a diffuser screen, reflector to efficiently distribute the excitation light across the entire illumination surface. However, the LCD panel light sources of the present invention are capable of providing substantially non-uniform distribution of light across the illumination surface, particularly distributions that reflect illumination only in areas corresponding to a given fluorophor.

Based on the sensitivities shown in Tables 14 and 15, the use of an LCD panel or other luminescent material with 10–30 times the light intensity of the panel used in the current study is sufficient to allow construction of a device that enables the visualization of the low levels of fluorescence typically encountered in many practical applications. Such LCD optical sources are likely to be commercially available in the near future.

A CCD camera does not have the same limitations with regard to the detection of a low photon flux as the human eye and, therefore, is able to detect lower levels of emission. FIGS. 32 and 33 show images of TMR and FL fluorophors, respectively, obtained using a basic "consumer grade" CCD camera. An exposure time of 16 seconds was needed to acquire the images shown in FIGS. 32 and 33. CCD cameras are available with much better sensitivity, lower noise and unlimited exposure times. In combination with such a camera, LCD light sources provide the sensitivity need for a wide range of applications.

Figure 34:
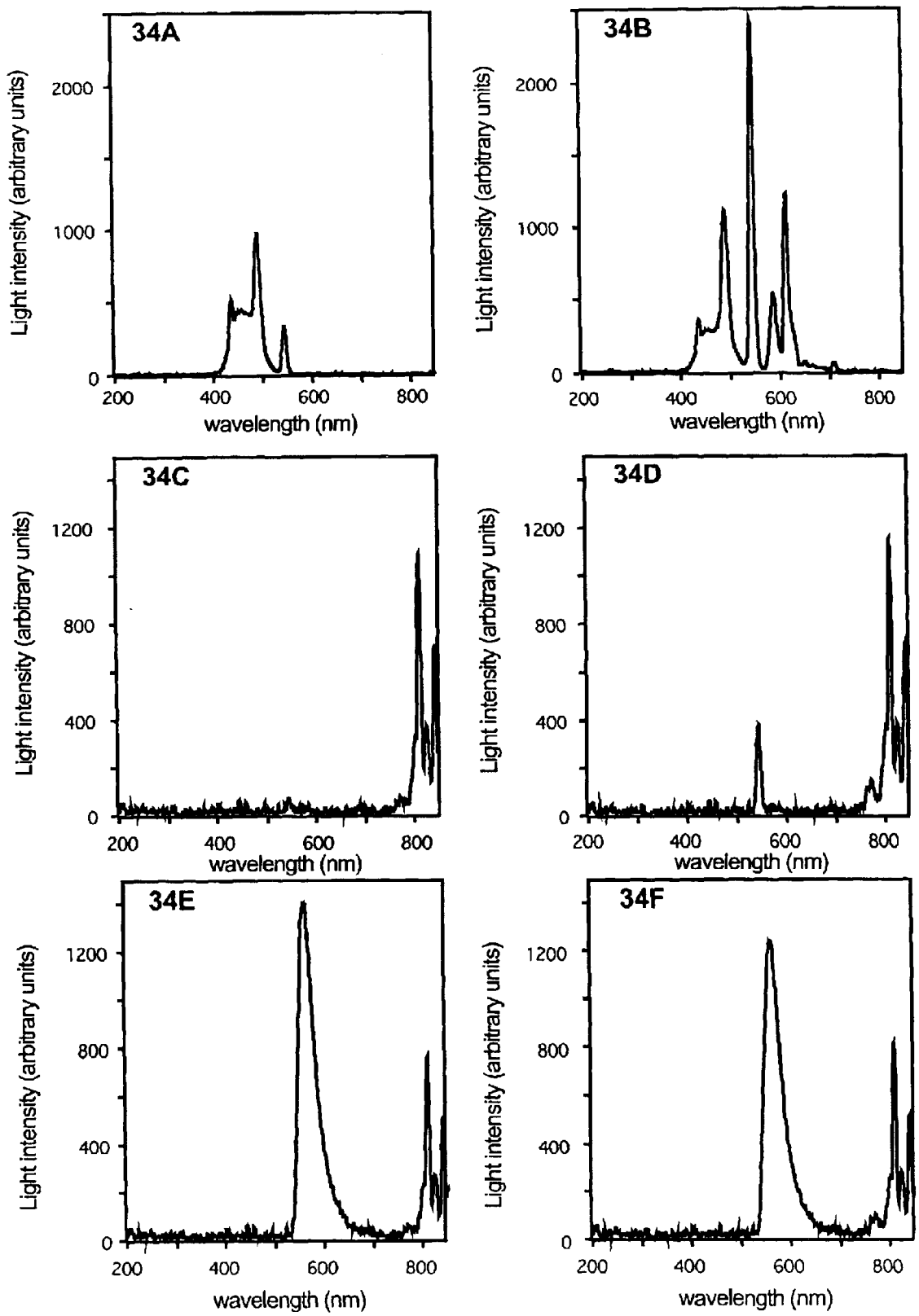
FIGS. 34A–F show spectra obtained in the detection of a 6 micromole/L fluorescein sample.

When choosing the components for an optical system that provides the best sensitivity of fluorescence detection, it is common to select components that match the excitation and emission wavelength maxima of the fluorophor under investigation. To illustrate the insufficiency of this approach, spectra were recorded to allow an analysis of the various wavelength components that contribute to excitation light, background light and fluorescence. These spectra are shown in FIG. 34.

The LCD panel light output is characterized by a peak at 488 nm, which is very close to the excitation maximum of fluorescein (about 490 nm). The intensity of this excitation peak generated by the white LCD panel is about 15% greater than when using the blue LCD panel. However, the fluorescence intensity of the fluorescein sample illuminated with the white LCD panel is about 8% lower than when illuminated with the blue LCD panel. This behavior is explained by considering the total light input and excitation response of the fluorophor under investigation. Over the wavelength range where fluorescein is appreciably excited (between about 410 nm and 525 nm) the white LCD panel emits about 6% less light than the blue LCD panel. This observation explains the reduced fluorescence observed with the white LCD panel.

In addition, spectra recorded with the white LCD light source show a higher transmission of excitation light through the filter set than when using the blue panel. This is primarily a result of the intense green component of the white light source. A higher transmission of excitation light substantially reduces the ability to detect the low levels of fluorescence.

To achieve the best fluorescence detection from a pattern of samples it is important to choose excitation and emission filters that provide the greatest possible light transmission across the greatest possible extent of the excitation and emission spectra of the fluorophor without significantly increasing the transmission of excitation light through the optical filter set.

FIG. 34 shows spectra of blue and white LCD light sources and the background and sample spectra associate with each for a 6 micromole/L fluorescein sample. The collection time of the spectra of the Blue and white LCD light sources was 5 milliseconds and the collection time for the background and sample spectra was 5000 milliseconds. The background and sample spectra shown in FIG. 34 show an appreciable level of infrared (IR) radiation is emitted by the LCD optical sources of the present invention. The IR emission from these sources was observed to be irrespective of selected color and was transmitted through both the excitation and emission filters. The intensity of the IR light is comparable to that of the fluorescence from the fluorescein sample. This radiation is not detectable by the human eye and so does not interfere with viewing the fluorescence. When using a CCD camera that is not equipped with an internal IR filter, however, this radiation can substantially interfere with the detection of fluorescence.

IR radiation is effectively blocked by a separate IR-blocking filter in combination with the excitation filter, emission filter or both. Alternatively, IR-blocking pigments may be added to either filter in combination with the appropriate visible light-blocking pigment(s) to effectively prevent transmission of the IR light generated from the light source to the detector.

The present invention includes embodiments in which excitation radiation from a LCD electroluminescent source is directly conducted onto fluorophors. In such embodiments, an excitation filter is not employed. The ability of LCD light sources to generate light of selected wavelengths is important to this aspect of the invention. Particularly, in embodiments not having an excitation filter, the LCD light source should be configured to provide a light source substantially free of light corresponding to the emission spectrum of the fluorophors to minimize interference with the separation and detection of emission.

There is no need for the LCD panel to be linked to a computer in a practical fluorescence viewing device. However, the use of an LCD panel in combination with a computer comprises an "intelligent fluorescence viewing unit" having several important benefits. The term "intelligent fluorescence viewing unit" refers to embodiments wherein a computer provides precise control of the illumination characteristics of the LCD light source. First, use of an integrated LCD light source and computer allows for selection of different colored screens to optimize detection of a selected fluorophor or selected combination of fluorophors. This feature may be combined with a selectable set of excitation and emission filters or tunable liquid crystal color filters. Second, this embodiment allows superimposing the image of a pattern of fluorophors, recorded with a camera, onto the panel while actually viewing the pattern and manipulating the samples. Software may be used to enhance the fluorescent image in a variety of ways enabling a human or robotic handler to better select appropriate regions from the fluorescent object(s) under study. Third, an integrated LCD light source and computer allows different colored excitation light to illuminate different areas of the surface of the light source depending on the precise location of fluorophors with particular excitation properties. Fourth, this embodiment permits rapidly alternation of several colors in a given area for the selective detection of multiple fluorophors in a sample. Finally, integration of a computer processor to the LCD optical sources of the present invention provides a feedback circuit which limits the spatial distribution of excitation light to those regions of the panel where fluorescence is generated. The remainder of the screen may be made black to reduce interference from background light and enhance sensitivity.

The present investigation has revealed several advantages of LCD light sources over conventional fluorescent lamps. First, LCD light sources provide greater flexibility with respect to the wavelength range of excitation radiation generated. Second, LCD light sources provide a highly uniform spatial distribution of light across the surface of the light source. Third, LCD light sources provide enhanced viewing sensitivity when the viewer or detector is positioned "off-axis." Finally, LCDs can be used with "intelligent viewing devices" having a large number of benefits.

Example 8

Ultraviolet Light Production from Various Light Sources

Ultraviolet light is a known mutagen and has been conclusively shown to severely damage fluorophors and fluorophor-containing materials, particularly samples containing oligonucleotides, polynucleotides, or both. For example, exposure of DNA-containing samples to radiation having a wavelength less than about 380 nm has been shown to cause DNA damage. In addition, studies indicate that the mutagenic properties of ultraviolet radiation is strongly dependent on wavelength, wherein light corresponding to the far-UV wavelength region (around 254 nm ) is substantially more damaging to DNA-containing samples than light corresponding to the near-UV wavelength region (around 365 nm). The mutagenic properties of ultraviolet light are reviewed and discussed by De Flora et al. in "Potent genotoxicity of halogen lamps, compared to fluorescent light and sunlight" , *Carcinogenesis,* 11(12):2171–2177, (1990).

As a result of the mutagenic nature of ultraviolet light, it is a goal of the present invention to provide methods, devices and device components for generating patterns of emission that do not expose a fluorophor or fluorophor-containing sample to substantial ultraviolet light levels. The ability of the present invention to generate patterns of emission without using ultraviolet light was evaluated by comparing the ultraviolet light intensities generated by the present methods and devices to the those generated by a variety of conventional light sources. Specifically, ultraviolet light intensities were measured for a number of light sources and compared to exemplary excitation sources used in the present invention. The light sources evaluated include a bare halogen lamp (300 W/120 V ELH lamp #31219 from Apollo (Ronkonkoma, N.Y.), a halogen lamp assembled in a slide projector housing (750H slide projector from Kodak, Rochester, N.Y., equipped with a Sylvania 300 W/120 V ELH lamp;"assembled halogen lamp"), and ultraviolet lamps (4×15 W UV fluorescent lamps, the lamps were contained in a standard UV transilluminator housing with the UV filter plate removed). In addition, a blue fluorescent lamp light source (9 W, Sylvania Dulux S #CF9DS/blue) and an office lamp (15 W cool white fluorescent lamp, GE, #F15T8CW) were evaluated.

To directly measure light intensities in the ultraviolet, selected light sources were positioned approximately 50 cm from an Ocean Optics S2000 Fiber Optic Spectrometer (Dunedin, Fla.). The spectrometer was equipped with a #2 grating (200 nm–800 nm), 200 micrometer width entrance slit, variable long pass (200 nm–850 nm) detector filter, UV2 upgrade and L2 detector collection lens. Light from the various light sources was collected through a 200 micrometer optical fiber (UV/VIS) fitted with a cosine corrector (UV/VIS). Prior to detection, the light was attenuated using a fiber optic variable attenuator and then transmitted to the spectrometer unit through a 600 micrometer optical fiber (UV/VIS).

The optical sources were positioned such that the maximum integrated intensity over the UV and visible spectrum was observed. The attenuator was adjusted such that the most intense source evaluated did not saturate the detector. Specifically, the attenuator was adjusted such that the intensity measured by the spectrometer for the bare halogen lamp was around 3000 counts using a 3-millisecond collection time. This attenuator setting, referred to as attenuation setting #1, was used for all the light sources to ensure that the spectrometer signals for the various light sources could be quantitatively compared to each other.

Collection times for the various light sources were selected to ensure that a measurable signal was attained for each light source evaluated. Specifically, a 30 millisecond collection time was used for low-intensity light sources and a 3-millisecond collection time was used for high intensity light sources. All intensities reported here are corrected to reflect the collection times employed. There was no "wavelength response" calibration of the spectrometer.

All measurements were performed in a dark room to minimize interference from room lights. A background signal was also recorded in the absence of the light sources evaluated and subtracted from the spectra obtained.

Figure 35:
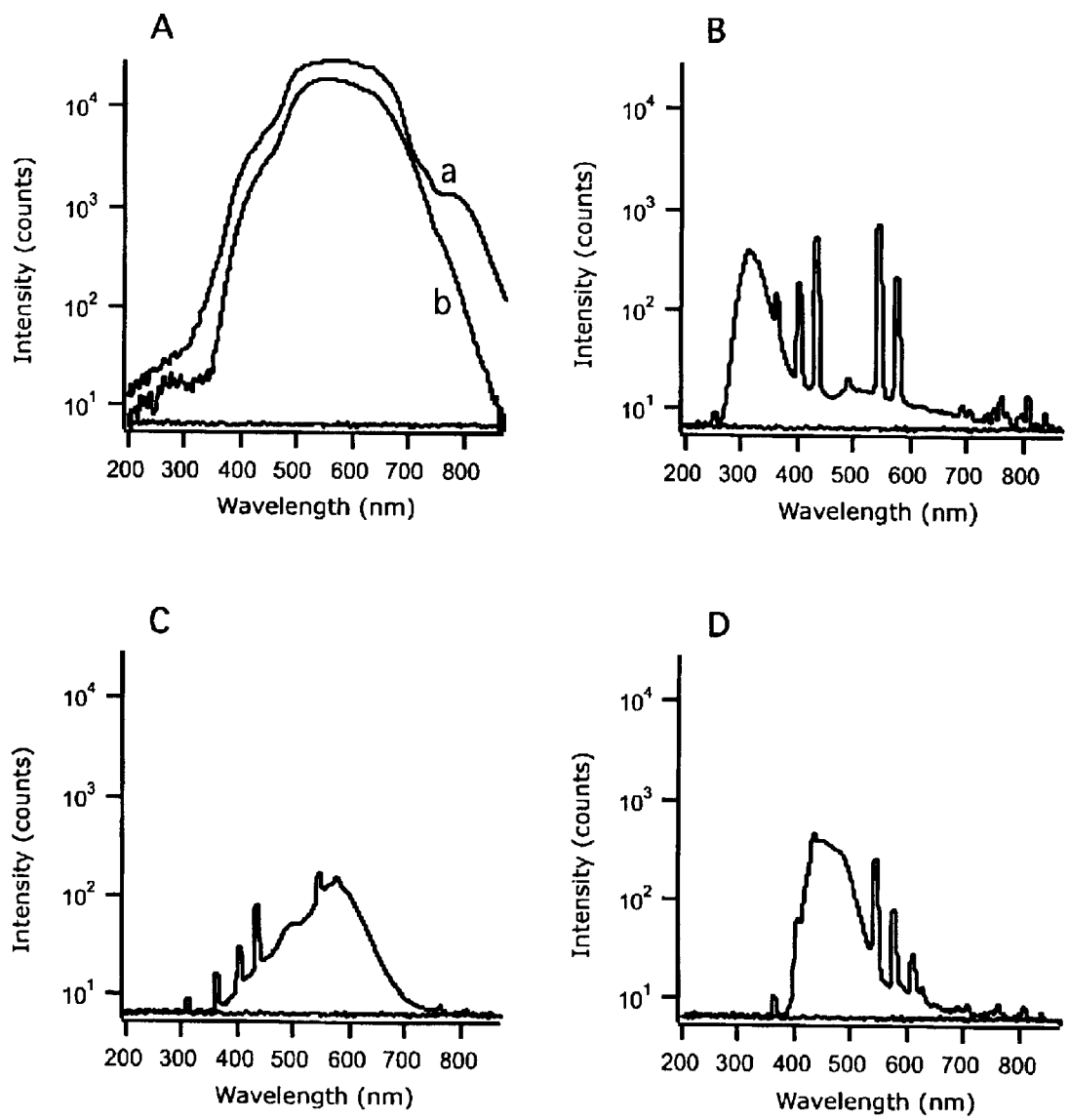
FIGS. 35A–D show spectra of variety of light sources in the visible and ultraviolet regions.
Figure 36:
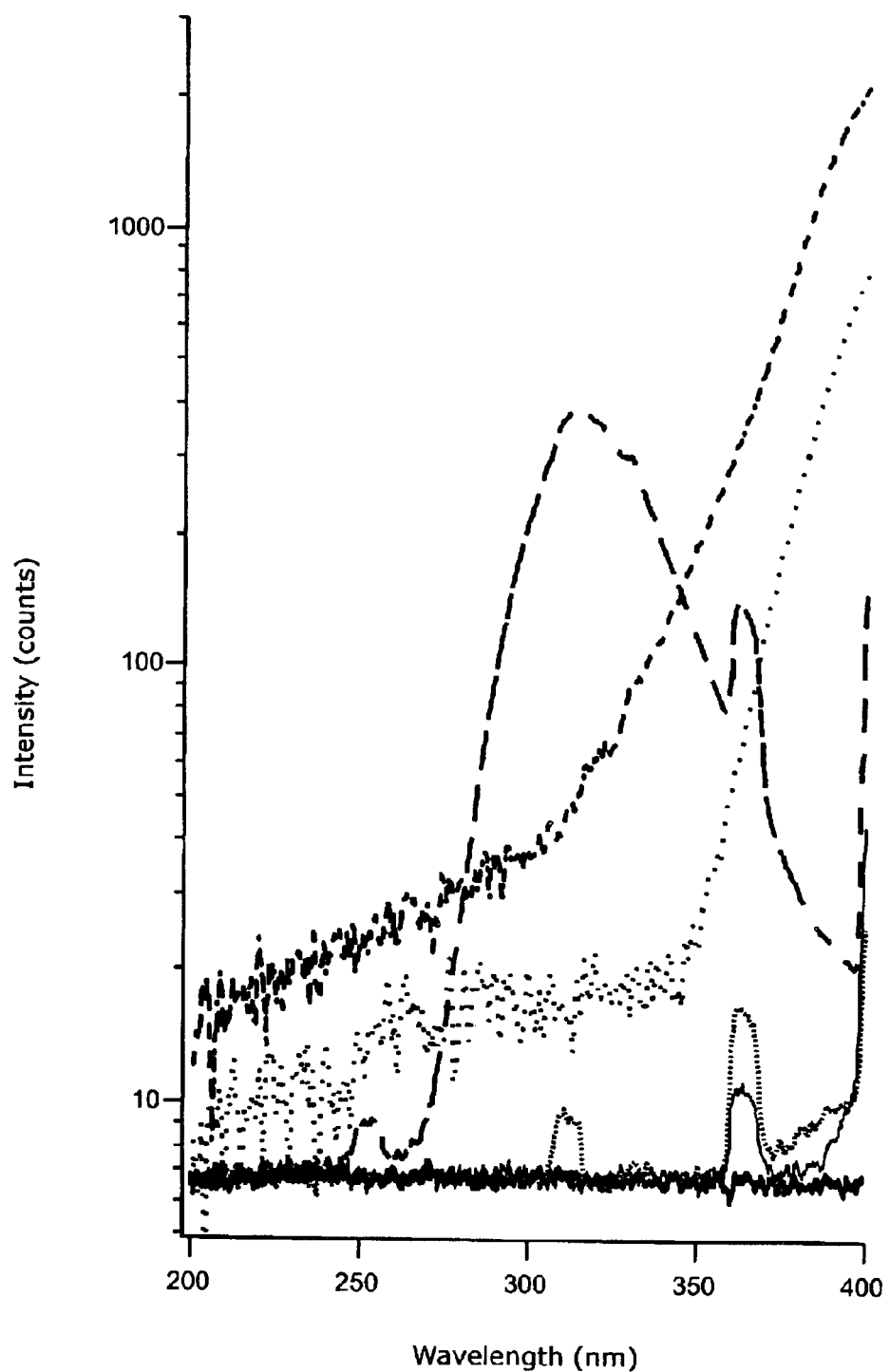
FIG. 36 shows an expanded scale view of the spectra of a variety of light sources in the ultraviolet. Spectra corresponding to a bare halogen lamp (short dashed line), assembled halogen lamp (widely spaced dotted line), an ultraviolet lamp (long dashed line), an office lamp (closely spaced dotted line) and a blue fluorescent lamp (thin solid line). In addition, the background is displayed as a thick solid line.

FIGS. 35A–D shows spectra of the various light source obtained. Intensities in the ultraviolet and visible regions are shown in FIG. 35. FIG. 35A shows spectra of a bare halogen lamp (A) and an assembled halogen lamp (B). FIG. 35B shows the spectrum of a ultraviolet lamp. FIG. 35C shows the spectrum of an office lamp. FIG. 35D shows the spectrum of a blue fluorescent lamp light. Also shown in FIGS. 35A–D are the background spectra corresponding to each measurement. FIG. 36 shows an expanded scale view of the various spectra from about 200 nm to about 400 nm. The various spectra in FIG. 36 are identified as follows: background signal—thick solid line; blue fluorescent lamp—thin solid line; office lamp—closely spaced dotted line; assembled halogen lamp—widely spaced dotted line; bare halogen lamp—short dashed line; UV lamp—long dashed line. A logarithmic scale on the y-axis (intensity) was used to accommodate the widely varying radiation intensities of the various light sources over the ultraviolet region. Table 16 provides a comparison of the integrated intensities of the various light sources over the ultraviolet and ultraviolet and visible wavelength regions.

As shown in FIG. 36 and in Table 16, the bare halogen lamp and the assembled halogen lamp emit over 290 and 78 times more ultraviolet light, respectively, than the exemplary blue fluorescent light source of the present invention. Reference to UV intensity refers to light having wavelengths ranging from 200 nm to 380 nm. In addition, the ultraviolet light source emits over 260 times more ultraviolet light than the exemplary blue fluorescent light source of the present invention. In addition, as shown in FIG. 36 the office light generated much less ultraviolet light than the halogen and UV light sources. The office light source was observed, however, to emit more ultraviolet light than the exemplary blue fluorescent light source. These measurements illustrate that the light sources of the present invention are capable of generating exceptionally low ultraviolet light intensities.

An analysis of the UV spectra of the various light sources evaluated also showed that the halogen lamps and ultraviolet lamps emit substantially more short wavelength UV light (less than 250 nm) than the blue fluorescent lamp of the present invention. The ability of the present invention to generate and view patterns of fluorophor emission without significant amounts of short wavelength radiation is beneficial because short wavelength ultraviolet light has been demonstrated to be very damaging to fluorophor-containing materials.

As also shown in FIG. 35 and in Table 16, halogen lamp light sources emit approximately two orders of magnitude more visible light than the exemplary blue fluorescent light source and office light sources of the present invention. The massive amount of visible light generated by the halogen light sources limits the sensitivity achievable for the detection of fluorophors and fluorophor-containing materials. First, the extremely high visible light intensities corresponding to the excitation wavelengths of the fluorophors generated by halogen light sources make it difficult to effectively prevent this radiation from passing through the emission filter and interfering with the detection and visualization of the emission. Second, the extremely high visible light intensities make it difficult to substantially prevent visible light from the excitation light source having wavelengths corresponding to the emission of fluorophors from passing through the excitation filter and interfering with the detection and visualization of the emission. Indeed, the visible light generated by halogen light sources is so intense that unwanted detection of light from the excitation light source is difficult if not impossible to avoid. The detection of this light interferes with the isolation and selective detection of light originating from the fluorophors and, therefore, undermines the sensitivities achievable.

The halogen lamps evaluated were also observed to generate substantially more infrared radiation than the exemplary blue fluorescent light and office lamp light sources of the present invention. Generation of infrared radiation is undesirable because it passes through most excitation and emission filters and is efficiently detected by many detectors such as CCD detectors. Accordingly, use of halogen lamps as excitation sources necessitates the use of additional filters or a bandpass filter to substantially prevent transmission of infrared light.

TABLE 16

Summary of total light intensity and ultraviolet light intensity for a variety of light sources. All data is normalized to 30 milliseconds collection time and was all collected using attenuator setting 1.

| Lamp | Total Intensity | UV Intensity |
| --- | --- | --- |
| Bare Halogen Lamp | 16,700,00 | 53,915 |
| Assembled Halogen Lamp | 9,860,000 | 14,520 |
| Ultraviolet Lamp | 96,500 | 48,675 |
| Office Lamp | 46,200 | 379 |
| Blue Fluorescent lamp | 94,300 | 185 |

Spectra were also obtained for a variety of light source and filter combinations to determine the ultraviolet light intensities exposed to a fluorophor-containing material during analysis. These experiments were performed as described above with the exception that an Acrylite #668-0GP blue excitation filter was positioned between the light source and the spectrometer. In addition, the collection times for these measurements varied from 5 milliseconds to 500 milliseconds, depending on the intensities generated by the various light source and filter combinations. The longer collection times were required in order to collect sufficient light when the blue filter was in place. Finally, the attenuator setting employed for these measurements, referred to as attenuator setting #2, was selected to prevent detector saturation and to provide a measurable signal from all light source-filter combinations evaluated. All measurements were normalized with respect to collection time and attenuator setting to permit a quantitative comparison.

Table 17 shows the measured integrated light intensities for three different wavelength regions: (1) 230 nm to 335 nm; (2) 335 nm to 420 nm; and (3) 420 nm to 830 nm. Integrated intensities for various light sources with and without the presence of the blue excitation filter are provided in Table 17. The halogen lamp equipped with an excitation filter was observed to generate more than 80 times more light having wavelengths between 230 nm and 335 nm and more than 50 time more light having wavelengths between 335 nm and 420 nm than the blue light source and excitation filter combination of the present invention. Table 17 demonstrates that fluorophor-containing samples analyzed by the methods of the present invention are exposed to very low levels of ultraviolet light, particularly low levels of light having wavelengths between 230 nm and 335 nm.

The high intensities of light having wavelengths between 230 nm and 335 run generated by the halogen lamp equipped with a blue excitation filter are particularly important because such light has been directly correlated with the incidence of DNA damage in samples exposed to ultraviolet radiation. Indeed, studies suggest that light having wavelengths less than 335 nm is several orders of magnitude more mutagenic than light having wavelengths greater than 335 nm. Assuming that the 230 nm to 335 band is primarily responsible for the DNA damage caused to samples exposed to ultraviolet radiation, a DNA damage index may be calculated for the various light sources and light source-excitation filter combinations evaluated. "DNA damage index" in this context refers to the potential for a light source to cause damage to a DNA sample upon illumination. Table 18 summarizes the DNA damage indexes obtained from the present measurements. The DNA damage indexes shown in Table 18 are normalized with the blue fluorescent light source and blue 668 excitation combination having an arbitrary value of 1. Table 18 demonstrates that the methods of the present invention are capable of analyzing DNA-containing materials with minimized damage caused by exposure to ultraviolet light. To achieve a DNA damage index comparable in magnitude to the blue fluorescent light and blue excitation filter combination evaluated in the present study, the halogen light sources of the present invention must be combined with an excitation filter having percentage transmission ranging from about 0.05 to about 0.2% over a wavelength range of about 230 nm to 335 nm.

TABLE 17

Integrated light intensities for a number of light source and light source-excitation filter combinations. All data is normalized to 50 milliseconds collection time and attenuator setting 2.

| Lamp - Filter Combinations | 230 nm–335 nm | 335 nm–420 nm | 420 nm–830 nm |
|---|---|---|---|
| Blue fluorescent lamp (9 W) | 73 | 4790 | 91400 |
| Blue fluorescent lamp (9 W) + 668 filter | 34 | 724 | 38500 |
| Halogen lamp (300 W) | 14800 | 399000 | $2 \times 10^7$ |
| Halogen lamp (300 W) + 668 filter | 2840 | 38900 | $2 \times 10^6$ |
| Ultraviolet lamp (4 × 15 W) | 48400 | 24700 | 58100 |

TABLE 18

DNA damage indexes for a number of light source and light source-excitation filter combinations.

| Lamp-Filter Combinations | DNA Damage Index |
|---|---|
| Blue fluorescent lamp (9 W) | 2.1 |
| Blue fluorescent lamp (9 W) + 668 filter | 1.0 |
| Halogen lamp (300 W) | 434 |
| Halogen lamp (300 W) + 668 filter | 84 |
| Ultraviolet lamp (4 × 15 W) | 1423 |

It should be understood that the visible light fluorometric detection system as specifically described herein could be altered without deviating from its fundamental nature. For example, different light sources, sets and types of filters could be substituted for those exemplified and described herein, so long as the light reaching the light detector, i.e., the viewer's eye or detection device, contains sufficient information about the light emitted from the fluorophors whose fluorescence is being visualized to allow viewing of an image of the pattern of fluorescence and so long as sufficient interfering light has been filtered out such that visualization is possible. It is therefore to be understood that within the scope of the appended claims, the invention may be practiced in ways other than as specifically described herein.

Example 9

Photo-Bleaching

Photo-bleaching is a significant problem associated with generating patterns of radiant emission from fluorophors. The occurrence of photo-bleaching is particularly problematic for applications involving long illumination periods, such as when proteins are being isolated from a 2-D electrophoresis gel for subsequent use or analysis. In the present context, "photo-bleaching" refers to the degradation of fluorophors caused by exposure to radiant energy. Minimizing the extent of photo-bleaching is beneficial because it results in greater fluorophor lifetimes, thereby eliminating the need to re-stain a sample prior to analysis. Accordingly, it is a goal of the present invention to provide methods and devices for generating patterns of radiant emission from fluorophors without substantial photo-bleaching.

The ability of the present invention to generate patterns of radiant emission with minimized photo-bleaching was directly evaluated by comparing the decrease in fluorescence intensity from samples exposed to exciting radiation generated by the present methods and prior art methods employing an ultraviolet light transilluminator. A SDS (sodium dodecyl sulfate) polyacrylamide gel was loaded with 3 identical aliquots of protein molecular weight standards (15 ng per band), subjected to electrophoresis and subsequently stained with SYPRO Orange (1:5,000). Two complete protein lanes were cut out from the gel and exposed to exciting radiation for eight minutes generated by the methods of the present invention and by a 312 nm UV transilluminator. The third protein lane was not exposed to illuminating radiation and, thereby provided a control for the experiment. Fluorescent images were generated for each of the three protein lanes using the methods of generating patterns of radiant emission of the present invention and photographed using a digital camera.

Figure 37:
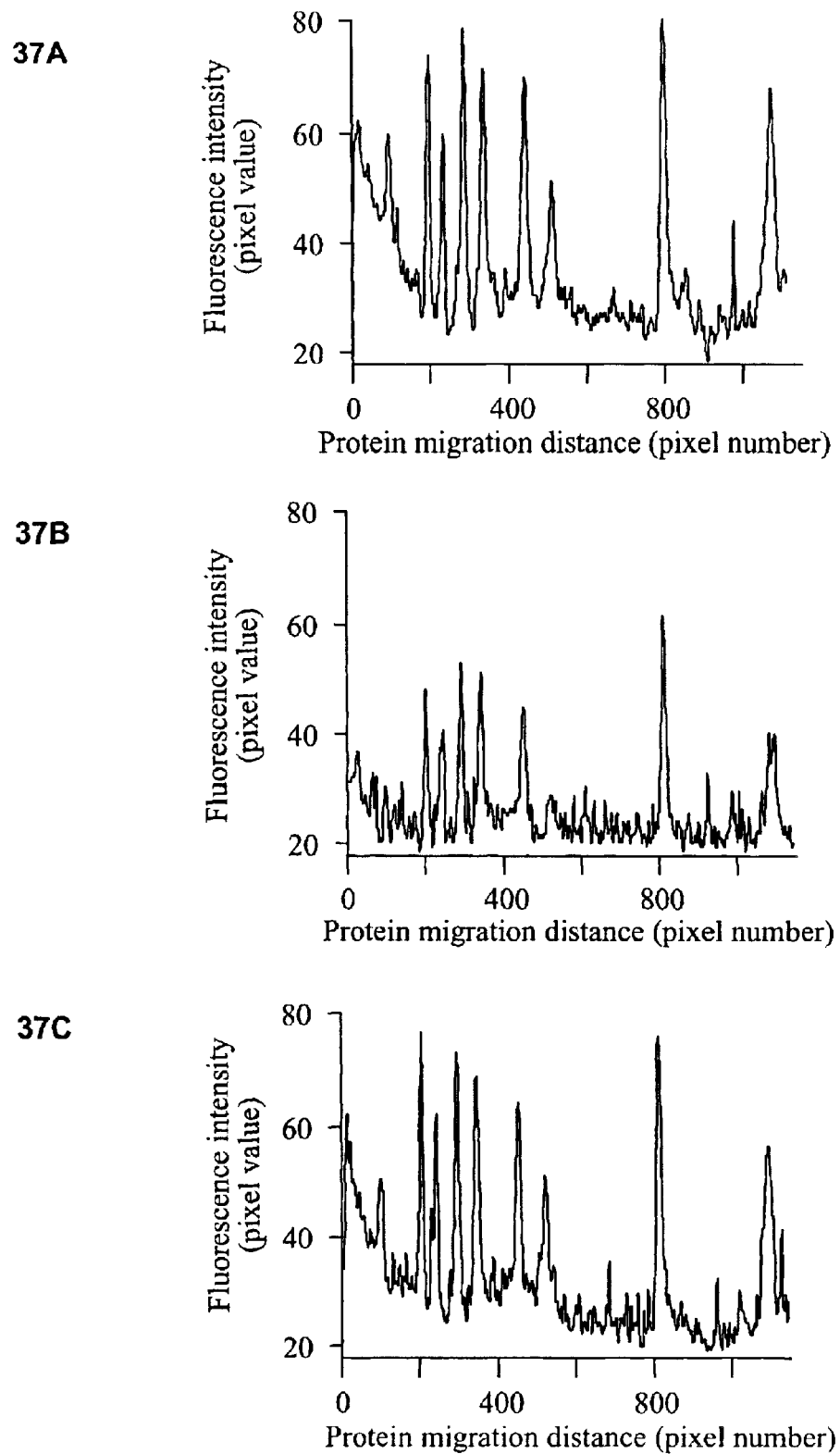
FIGS. 37A–C show the effect of exciting radiation on observed fluorescence intensities.

FIG. 37 shows patterns of fluorescence observed for each of the three protein channels analyzed. FIG. 37A shows the fluorescence intensities of the protein lane not exposed to exciting radiation prior to analysis. FIG. 37B shows the fluorescence intensities of the protein lane exposed to exciting radiation generated by the methods of the present invention. FIG. 37C shows the fluorescence intensities of the protein lane exposed to exciting radiation generated by the 312 nm ultraviolet light transilluminator.

A comparison of the fluorescence intensities in FIGS. 37A and 37C reveals that illumination with exciting radiation from the 312 nm ultraviolet light transilluminator for 8 minutes resulted in an approximately 40% decrease in integrated fluorescence intensity of the protein bands. The observed decrease in fluorescence intensities correlates to a degradation of the fluorophors in the sample. Interestingly, fluorophors associated with some proteins appeared to be more affected than others and were almost completely degraded after the eight minute illumination period. In contrast, a comparison of the fluorescence intensities in FIGS. 37A and 37B reveals that illumination with exciting radiation from the methods of the present invention resulted in an approximately 10% decrease in integrated fluorescence intensity of the protein bands.

The fluorescent images in FIGS. 34A–34C show that the present methods and devices for generating patterns of radiant emission from fluorophors result in significantly less photo-bleaching than prior art methods using UV transilluminators. Specifically, the intensities and wavelengths of light used for fluorophor excitation taught by the present invention allow excitation sources to be configured and arranged such that fluorophors do not undergo substantial photobleaching over an illumination period of about eight minutes. "Substantial photo-bleaching" is intended to be interpreted consistent with the meaning of this term by persons or ordinary skill in the art and refers to an amount of photobleaching that is not tolerated for a given application. Therefore, the methods and devices of the present invention are especially well suited to applications that require prolonged exposure of fluorophor containing samples to exciting radiation.

I claim:

1. A visible light photoluminescent imaging system for viewing one or more patterns of fluorescence emitted by fluorophors capable of being excited by light of an excitation type and capable of emitting light of an emitted type, said system comprising:
   a) an electroluminescent light-producing element having a luminous surface that produces light;
   b) a first optical filter positioned between said the luminous surface of the electroluminescent light-producing element and said fluorophors, wherein the first optical filter is capable of transmitting light of said excitation type and of substantially preventing transmission of light of said emitted type; and
   c) a second optical filter positioned in optical communication with said fluorophors, wherein said second optical filter is capable of transmitting light of said emitted type from said fluorophors and of substantially preventing transmission of said excitation light;

said system being constructed and arranged such that patterns of emission from the fluorophors are viewable.

2. The visible light photoluminescent imaging system of claim 1 wherein the electroluminescent light-producing element comprises one or more liquid crystals.

3. The visible light photoluminescent imaging system of claim 2 wherein the electroluminescent light-producing element comprises a liquid crystal display panel.

4. The visible light photoluminescent imaging system of claim 3 wherein the electroluminescent light-producing element comprises a computer monitor.

5. The visible light photoluminescent imaging system of claim 3 wherein the liquid crystal display panel has a white color setting.

6. The visible light photoluminescent imaging system of claim 3 wherein the liquid crystal display panel has a blue color setting.

7. The visible light photoluminescent imaging system of claim 3 wherein the liquid crystal display panel has a blue-green color setting.

8. The visible light photoluminescent imaging system of claim 3 wherein the liquid crystal display panel has a green color setting.

9. The visible light photoluminescent imaging system of claim 1 wherein the electroluminescent light-producing element has a power consumption of less than or equal to about 24 W.

10. The visible light photoluminescent imaging system of claim 1 comprising at least one additional optical filter positioned in optical communication with said second optical filter, wherein the additional optical filter is capable of transmitting light of said emitted type form said fluorophors and of substantially preventing transmission of infrared light.

11. The visible light photoluminescent imaging system of claim 1 comprising a detector in optical communication with the second optical filter.

12. The visible light photoluminescent imaging system of claim 11 wherein the detector is positioned at an angle 45° or more from normal incidence with respect to a plane containing the second filter.

13. The visible light photoluminescent imaging system of claim 1 wherein the electroluminescent light-producing element has an illumination surface that has a non-uniform luminous flux across the illumination surface.

14. The visible light photoluminescent imaging system of claim 1 wherein the electroluminescent light-producing element has an illumination surface that has a substantially uniform luminous flux across the illumination surface.

15. The visible light photoluminescent imaging system of claim 1 wherein the wavelength of light produced by the electroluminescent imaging system is uniform across the illumination surface.

16. The visible light photoluminescent imaging system of claim 1 wherein the wavelength of light produced by the electroluminescent imaging system is non-uniform across the illumination surface.

17. The visible light photoluminescent imaging system of claim 1 comprising a computer operationally connected to the electroluminescent light-producing element, wherein the computer controls the light produced by the electroluminescent light-producing element.

18. The visible light photoluminescent imaging system of claim 17 wherein the computer selects the wavelengths of the light produced by the electroluminescent light-producing element.

19. The visible light photoluminescent imaging system of claim 17 wherein the computer selects the spatial distribution of light across the illumination surface.

20. The visible light photoluminescent imaging system of claim 17 wherein the computer controls the intensity of the light produced by the electroluminescent light-producing element.

21. The visible light photoluminescent imaging system of claim 1 wherein the electroluminescent light-producing element comprises one or more light emitting diodes.

22. The visible light photoluminescent imaging system of claim 1 wherein said first optical filter and said second optical filter are integrated into a gel cassette.

23. The visible light photoluminescent imaging system of claim 1 wherein said fluorophors are provided in a gel cassette.

24. A field monitoring device for viewing one or more patterns of emission from fluorophors capable of being excited by light of an excitation type and capable of emitting light of an emitted type, said system comprising:
  a) an excitation source comprising at least one light-producing element that produces light, at least a portion of which is capable of exciting said fluorophors, and a first optical filter, positioned between said light-producing element and said fluorophors that is capable of transmitting light of said excitation type and of substantially preventing transmission of light of said emitted type, wherein the excitation source produces light substantially free of light in the ultraviolet region; and
  b) a second filter positioned in optical communication with said fluorophors, wherein said second optical filter is capable of transmitting light of said emitted type from said fluorophors and of substantially preventing transmission of light from said excitation source;
said system being constructed and arranged such that patterns of emission from said fluorophors are viewable.

25. The photoluminescent field monitoring device of claim 24 comprising a detector.

26. The photoluminescent field monitoring device of claim 24 wherein the excitation source is handheld.

27. The photoluminescent field monitoring device of claim 24 wherein the excitation source is stationary.

28. The photoluminescent field monitoring device of claim 24 comprising an underwater photoluminescent imaging system.

29. The photoluminescent field monitoring device of claim 24 wherein the excitation source has a power consumption less than about 9 W.

30. The photoluminescent field monitoring device of claim 24 operationally coupled to a microfluidic or microarray device.

31. A method of generating a pattern of radiant emission from fluorophors capable of being excited by light of an excitation type and capable of emitting light of an emitted type, said method comprising the steps:
  a) passing light of said excitation type and substantially free of ultraviolet light from an excitation source on to the fluorophors whereby the fluorophors emit light of the emitted type, wherein the excitation source comprises a light-producing element and a first optical filter positioned between said light-producing element and the fluorophors, wherein the first filter is capable of transmitting light of said excitation type and of substantially preventing transmission of light of said emitted type; and
  b) passing said emitted light through a second optical filter, which is capable of transmitting light of said emitted type from said fluorophors and capable of substantially prevent transmission of light of said excitation type.

32. The method of claim 31 wherein the fluorophors are trace contaminants in a field sample.

33. The method of claim 31 wherein the fluorophors are comprised in a genetically modified organism.

34. The method of claim 33 comprising a method wherein said fluorophors are contained in genetically-modified plants.

35. The method of claim 31 wherein the fluorophors are comprised in a tissue sample or sample of bodily fluid.

36. A method of viewing a pattern of radiant emission from fluorophors capable of being excited by light of an excitation type and capable of emitting light of an emitted type, said method comprising the steps:
  a) passing light of said excitation type and substantially free of ultraviolet light from an excitation source on to the fluorophors, whereby the fluorophors emit light of the emitted type, wherein the excitation source comprises a light-producing element and a first optical filter positioned between said light-producing element and the fluorophors, wherein the first filter is capable of transmitting light of said excitation type and of substantially preventing transmission of light of said emitted type;
  b) passing said emitted light through a second optical filter, which is capable of transmitting light of said emitted type from said fluorophors and capable of substantially prevent transmission of light of said excitation type; and
  c) detecting said emitted light with a detector.

37. The method of claim 36 wherein the detector is a human eye.

38. The method of claim 36 wherein the detector is a charged coupled device.

39. The method of claim 36 wherein the detector is a CMOS detector.

40. The method of claim 36 wherein the detector is a camera.

41. A vessel for viewing one or more patterns of fluorescence emitted by fluorophors capable of being excited by light of an excitation type and capable of emitting light of an emitted type, said vessel comprising:
  a) an excitation source comprising at least one light-producing element that produces light, at least a portion of which is capable of exciting said fluorophors, and a excitation filter positioned between said light-producing element and said fluorophors, wherein the first filter is capable of transmitting light of said excitation type and of substantially preventing transmission of light of said emitted type;
  b) a bowl capable of positioning the fluorophors in optical communication with the light source; and
  c) at least one emission filter positioned in optical communication with said fluorophors, wherein said second optical filter is capable of transmitting light of said emitted type from said fluorophors and of substantially preventing transmission of light from said excitation source;

said vessel being constructed and arranged such that patterns of emission from said fluorophors are viewable.

42. The vessel of claim 41 which is a photoluminescent fish tank.

43. The vessel of claim 41 which is a photoluminescent drinking glass.

44. The vessel of claim 41 which is a photoluminescent display cabinet.

45. A method of generating one or more radiant images corresponding to images printed with ink containing fluorophors capable of being excited by light of an excitation type and capable of emitting light of an emitted type, comprising the steps of:

a) passing light of said excitation type from an excitation source on to the fluorophors, whereby ink containing fluorophors emits light of the emitted type, wherein the excitation source comprises at least one light-producing element and a first optical filter positioned between said light-producing element and the images printed with ink containing fluorophors, wherein the first filter is capable of transmitting light of said excitation type and of substantially preventing transmission of light of said emitted type, wherein the excitation source produces light substantially free of light in the ultraviolet region;

b) passing said emitted light through a second optical filter in optical communication with the images printed with ink containing fluorophors, wherein the second filter is capable of transmitting light of said emitted type from said fluorophors and capable of substantially preventing transmission of light of said excitation type; whereby one or more radiant images corresponding to images printed with the ink containing fluorophors are viewable.

46. A room installation for generating radiant images, patterns, or both from fluorophors capable of being excited by light of an excitation type and capable of emitting light of an emitted type, said room installation comprising:

a) an excitation source comprising at least one light-producing element that produces light and a first optical filter positioned between said light-producing element and said fluorophors, wherein the first optical filter is capable of transmitting light of said excitation type and of substantially preventing transmission of light of said emitted type, wherein the excitation source produces light substantially free of light in the ultraviolet region; and b) a second filter positioned in optical communication with said fluorophors, wherein said second optical filter is capable of transmitting light of said emitted type from said fluorophors and of substantially preventing transmission of said excitation light.

47. The photoluminescent room installation of claim 46 wherein said excitation source is stationary.

48. The photoluminescent room installation of claim 46 wherein said excitation source is mobile.

49. The photoluminescent room installation of claim 46 wherein said second filter is incorporated into eye glasses or contact lenses.

50. A method of generating a pattern of radiant emission from an oligonucleotide sample, polynucleotide sample, or both containing fluorophors capable of being excited by light of an excitation type and capable of emitting light of an emitted type, said method comprising the steps:

a) passing light of said excitation type generated by an excitation source onto the oligonucleotide sample, polynucleotide sample, or bpth, whereby the fluorophors emit light of the emitted type, wherein the excitation source comprises a light-producing element and a first optical filter positioned between said light-producing element and the oligonucleotide sample, polynucleotide sample, or both, wherein the first filter is capable of transmitting light of said excitation type and of substantially preventing transmission of light of said emitted type; and b) passing said emitted light through a second optical filter, which is capable of transmitting light of said emitted type from said fluorophors and capable of substantially prevent transmission of light of said excitation type;

wherein the excitation source is configured and arranged such that the oligonucleotide sample, polynucleotide sample, or both, undergo no substantial damage over an illumination period of about five minutes.

51. The method of claim 50 wherein the oligonucleotide sample, polynucleotide sample or both contain DNA.

52. The method of claim 50 wherein said first optical filter and said second optical filter are integrated into a gel cassette.

53. A method of generating a pattern of radiant emission from fluorophors capable of being excited by light of an excitation type and capable of emitting light of an emitted type, said method comprising the steps:

a) passing light of said excitation type generated by an excitation source onto the fluorophors, whereby the fluorophors emit light of the emitted type, wherein the excitation source comprises a light-producing element and a first optical filter positioned between said light-producing element and the fluorophors, wherein the first filter is capable of transmitting light of said excitation type and of substantially preventing transmission of light of said emitted type; and b) passing said emitted light through a second optical filter, which is capable of transmitting light of said emitted type from said fluorophors and capable of substantially prevent transmission of light of said excitation type;

wherein the excitation source is configured and arranged such that the fluorophors do not undergo substantial photobleaching over an illumination period of about eight minutes.

54. The method of claim 35 wherein said first optical filter and said second optical filter are integrated into a gel cassette.

* * * * *

UNITED STATES PATENT AND TRADEMARK OFFICE
CERTIFICATE OF CORRECTION

PATENT NO. : 6,914,250 B2
DATED : July 5, 2005
INVENTOR(S) : Seville

It is certified that error appears in the above-identified patent and that said Letters Patent is hereby corrected as shown below:

Column 51,
Line 66, delete "the" after "between said".

Column 52,
Line 40, replace "form" with -- from --.

Column 54,
Lines 10 and 38, replace "prevent" with -- preventing --.
Lines 15 and 20, delete "comprised" after "fluorophors are."

Column 56,
Line 8, replace "bpth" with -- both --.
Lines 20 and 47, replace "prevent" with -- preventing --.
Line 53, replace "35" with -- 53 --.

Signed and Sealed this

Twentieth Day of December, 2005

JON W. DUDAS
*Director of the United States Patent and Trademark Office*